United States Patent
Shin et al.

(10) Patent No.: US 12,421,297 B2
(45) Date of Patent: Sep. 23, 2025

(54) TYPE 1 INTERFERON NEUTRALIZING FC-FUSION PROTEIN AND USE THEREOF

(71) Applicants: SEOUL NATIONAL UNIVERSITY R&DB FOUNDATION, Seoul (KR); LOGONE BIO CONVERGENCE RESEARCH FOUNDATION, Seoul (KR)

(72) Inventors: Young Kee Shin, Seoul (KR); Sae Hyung Lee, Seoul (KR); Sung Su Kim, Seoul (KR)

(73) Assignees: SEOUL NATIONAL UNIVERSITY R&DB FOUNDATION, Seoul (KR); LOGONE BIO CONVERGENCE RESEARCH FOUNDATION, Seoul (KR)

( * ) Notice: Subject to any disclaimer, the term of this patent is extended or adjusted under 35 U.S.C. 154(b) by 1127 days.

(21) Appl. No.: 17/417,896

(22) PCT Filed: Dec. 20, 2019

(86) PCT No.: PCT/KR2019/018233
§ 371 (c)(1),
(2) Date: Jun. 24, 2021

(87) PCT Pub. No.: WO2020/138868
PCT Pub. Date: Jul. 2, 2020

(65) Prior Publication Data
US 2022/0089684 A1    Mar. 24, 2022

(30) Foreign Application Priority Data
Dec. 24, 2018  (KR) .................. 10-2018-0168801

(51) Int. Cl.
| C07K 14/715 | (2006.01) |
| A61K 38/00  | (2006.01) |
| C07K 16/24  | (2006.01) |
| C12N 5/071  | (2010.01) |

(52) U.S. Cl.
CPC ........ *C07K 14/7156* (2013.01); *C07K 16/249* (2013.01); *C12N 5/0686* (2013.01); *A61K 38/00* (2013.01); *C07K 2317/76* (2013.01); *C07K 2319/30* (2013.01)

(58) Field of Classification Search
None
See application file for complete search history.

(56) References Cited

U.S. PATENT DOCUMENTS

| 2006/0286641 A1* | 12/2006 | Smith ............... C07K 14/7156 |
| | | 435/325 |
| 2017/0058045 A1* | 3/2017 | Gromada ........... C07K 16/2866 |
| 2018/0237541 A1 | 8/2018 | Kim et al. |

FOREIGN PATENT DOCUMENTS

| JP | 2008536477 A | 9/2008 |
| JP | 2012531439 A | 12/2012 |
| JP | 2016506377 A | 3/2016 |
| WO | 2006084337 A1 | 8/2006 |
| WO | 2006138610 A2 | 12/2006 |
| WO | 2010151792 A1 | 12/2010 |
| WO | 2019040674 A1 | 2/2019 |

OTHER PUBLICATIONS

Deshpande, Ashlesha et al. Kinetic analysis of cytokine-mediated receptor assembly using engineered FC heterodimers. Protein Science. 2013, vol. 22. pp. 1100-1108.
GenBank: AAH21825.1: Interferon (alpha, beta and omega) receptor 1 [*Homo sapiens*] (Jul. 15, 2006).
GenBank: AAU21038.1: interferon (alpha. beta and omega) receptor 2 [*Homo sapiens*] (Sep. 8, 2004).
Kuruganti, Snlahtila et al. Cytokine activation by antibody fragments targeted to cytokine-receptor signaling complexes. The Journal of Biological Chemistry. 2016, vol. 291, No. 1, pp. 447-461.
PDB: 5VH5_A: Chain A Infliximab Fc (Dec. 13, 2018).
International Search Report issued by the Korean Intellectual Property Office in connection with International Application No. PCT/KR2019/018233 dated Apr. 2, 2020.
English Translation of Japanese Office Action for application No. 2021-537211, Nov. 28, 2023, 13 pages.

* cited by examiner

*Primary Examiner* — Daniel E Kolker
*Assistant Examiner* — Peter Johansen
(74) *Attorney, Agent, or Firm* — George Likourezos; Carter, DeLuca & Farrell LLP

(57) ABSTRACT

The present invention relates to a type 1 interferon neutralizing FC-fusion protein and a use thereof and, more specifically, to: a dimer-type polypeptide to which a monomer comprising an interferon receptor fragment or an antibody Fc fragment is bound; a preparation method there for; and a pharmaceutical composition comprising same. The type 1 interferon neutralizing FC-fusion protein of the present invention blocks binding between type 1 interferon and an interferon receptor, and has an excellent ability of inhibiting the signaling and biological activities of interferon, thereby enabling diseases mediated by a type 1 interferon to be effectively treated.

13 Claims, 9 Drawing Sheets
Specification includes a Sequence Listing.

SEQUENCE LISTING

```
<160> NUMBER OF SEQ ID NOS: 76

<210> SEQ ID NO 1
<211> LENGTH: 69
<212> TYPE: DNA
<213> ORGANISM: Artificial Sequence
<220> FEATURE:
<223> OTHER INFORMATION: Kozak-Signal sequence

<400> SEQUENCE: 1
gccaccatgt ggtggcgtct gtggtggctg ctgcttctgc tgttgctgct gtggcctatg      60
gtctgggcc                                                              69

<210> SEQ ID NO 2
<211> LENGTH: 23
<212> TYPE: PRT
<213> ORGANISM: Artificial Sequence
<220> FEATURE:
<223> OTHER INFORMATION: Kozak-Signal sequence

<400> SEQUENCE: 2

Ala Thr Met Trp Trp Arg Leu Trp Trp Leu Leu Leu Leu Leu Leu Leu
1               5                   10                  15

Leu Trp Pro Met Val Trp Ala
            20

<210> SEQ ID NO 3
<211> LENGTH: 1227
<212> TYPE: DNA
<213> ORGANISM: Artificial Sequence
<220> FEATURE:
<223> OTHER INFORMATION: IFNAR1 ExtraCellular Domain

<400> SEQUENCE: 3
aagaacctga agtcccctca gaaagtggaa gtggacatca tcgacgacaa cttcatcctg       60
cggtggaaca gatccgacga gtccgtgggc aacgtgacct tcagcttcga ctaccagaaa      120
accggcatgg acaactggat caagctgtcc ggctgccaga acatcacctc taccaagtgc      180
aacttctcca gcctgaagct gaacgtgtac gaggaaatca gctgcggat ccgggccgag       240 aaagagaaca ccagcagttg gtacgaggtg gacagcttca cccctttcag aaaggcccag      300
atcggccctc ctgaagtgca cctggaagcc gaggataagg ccatcgtgat ccacatcagc      360
cccggcacca aggactctgt gatgtgggct ctcgacggcc tgtccttcac ctacagcctg      420
gtcatctgga agaactcctc cggcgtggaa gagagaatcg agaacatcta ctcccggcac      480
aagatctaca gctgagccc cgagacaacc tactgcctga agtgaaggc cgctctgctg       540 acctcctgga agatcggcgt gtactctccc gtgcactgca tcaagaccac cgtggaaaac      600
gagctgcctc ctccagagaa catcgaggtg tccgtgcaga accagaacta cgtgctgaag      660
tgggactaca ccctacgccaa catgacccttt caggtgcagt ggctgcacgc ttttctgaag      720
cggaaccctg gcaaccacct gtacaagtgg aagcagattc ccgactgcga gaacgtgaaa      780
```

-continued

```
accacacagt gcgtgttccc tcagaacgtg ttccagaagg gcatctacct gctgagagtg    840
caggcctccg acggcaacaa caccagcttt tggagcgaag agatcaagtt cgataccgag    900
atccaggcct tcctgctgcc tccagtgttc aacatcagat ccctgtccga ctccttccac    960
atctacatcg gcgctcctaa gcagtccggc aacacccctg tgatccagga ctaccctctg   1020
atctacgaga tcatcttctg ggagaacacc tccaacgccg agcggaagat catcgagaag   1080
aaaaccgacg tgaccgtgcc taacctgaag cctctgaccg tgtactgcgt gaaggctagg   1140
gcccacacca tggacgaaaa gctgaacaag tcctccgtgt ctccgacgc cgtgtgcgaa    1200 aagaccaagc caggcaacac ctctaaa                                       1227
```

<210> SEQ ID NO 4
<211> LENGTH: 409
<212> TYPE: PRT
<213> ORGANISM: Artificial Sequence
<220> FEATURE:
<223> OTHER INFORMATION: IFNAR1 ExtraCellular Domain

<400> SEQUENCE: 4

```
Lys Asn Leu Lys Ser Pro Gln Lys Val Glu Val Asp Ile Ile Asp Asp
1               5                   10                  15

Asn Phe Ile Leu Arg Trp Asn Arg Ser Asp Glu Ser Val Gly Asn Val
            20                  25                  30

Thr Phe Ser Phe Asp Tyr Gln Lys Thr Gly Met Asp Asn Trp Ile Lys
        35                  40                  45

Leu Ser Gly Cys Gln Asn Ile Thr Ser Thr Lys Cys Asn Phe Ser Ser
    50                  55                  60

Leu Lys Leu Asn Val Tyr Glu Glu Ile Lys Leu Arg Ile Arg Ala Glu
65                  70                  75                  80

Lys Glu Asn Thr Ser Ser Trp Tyr Glu Val Asp Ser Phe Thr Pro Phe
                85                  90                  95

Arg Lys Ala Gln Ile Gly Pro Pro Glu Val His Leu Glu Ala Glu Asp
            100                 105                 110

Lys Ala Ile Val Ile His Ile Ser Pro Gly Thr Lys Asp Ser Val Met
        115                 120                 125

Trp Ala Leu Asp Gly Leu Ser Phe Thr Tyr Ser Leu Val Ile Trp Lys
    130                 135                 140

Asn Ser Ser Gly Val Glu Glu Arg Ile Glu Asn Ile Tyr Ser Arg His
145                 150                 155                 160

Lys Ile Tyr Lys Leu Ser Pro Glu Thr Thr Tyr Cys Leu Lys Val Lys
                165                 170                 175

Ala Ala Leu Leu Thr Ser Trp Lys Ile Gly Val Tyr Ser Pro Val His
            180                 185                 190

Cys Ile Lys Thr Thr Val Glu Asn Glu Leu Pro Pro Pro Glu Asn Ile
        195                 200                 205

Glu Val Ser Val Gln Asn Gln Asn Tyr Val Leu Lys Trp Asp Tyr Thr
    210                 215                 220

Tyr Ala Asn Met Thr Phe Gln Val Gln Trp Leu His Ala Phe Leu Lys
225                 230                 235                 240

Arg Asn Pro Gly Asn His Leu Tyr Lys Trp Lys Gln Ile Pro Asp Cys
                245                 250                 255

Glu Asn Val Lys Thr Thr Gln Cys Val Phe Pro Gln Asn Val Phe Gln
            260                 265                 270

Lys Gly Ile Tyr Leu Leu Arg Val Gln Ala Ser Asp Gly Asn Asn Thr
```

```
                275                 280                 285
Ser Phe Trp Ser Glu Glu Ile Lys Phe Asp Thr Glu Ile Gln Ala Phe
    290                 295                 300

Leu Leu Pro Pro Val Phe Asn Ile Arg Ser Leu Ser Asp Ser Phe His
305                 310                 315                 320

Ile Tyr Ile Gly Ala Pro Lys Gln Ser Gly Asn Thr Pro Val Ile Gln
                325                 330                 335

Asp Tyr Pro Leu Ile Tyr Glu Ile Ile Phe Trp Glu Asn Thr Ser Asn
                340                 345                 350

Ala Glu Arg Lys Ile Ile Glu Lys Lys Thr Asp Val Thr Val Pro Asn
            355                 360                 365

Leu Lys Pro Leu Thr Val Tyr Cys Val Lys Ala Arg Ala His Thr Met
    370                 375                 380

Asp Glu Lys Leu Asn Lys Ser Ser Val Phe Ser Asp Ala Val Cys Glu
385                 390                 395                 400

Lys Thr Lys Pro Gly Asn Thr Ser Lys
                405
```

<210> SEQ ID NO 5
<211> LENGTH: 651
<212> TYPE: DNA
<213> ORGANISM: Artificial Sequence
<220> FEATURE:
<223> OTHER INFORMATION: IFNAR2 ExtraCellular Domain

<400> SEQUENCE: 5

```
atctcctacg acagccctga ctacaccgac gagtcctgca ccttcaagat ctccctgcgg    60
aacttccggt ccatcctgtc ctgggagctg aagaaccact ccatcgtgcc cacacactac   120
accctgctgt acaccatcat gtccaagcct gaggacctga aggtggtcaa gaactgcgcc   180
aacaccacca gatctttctg cgacctgacc gatgagtggc ggtctaccca cgaggcttac   240
gtgacagtgc tggaaggctt ctccggcaat accacactgt tcagctgctc ccacaacttc   300
tggctggcca tcgacatgtc cttcgagcct ccagagttcg agatcgtggg cttcaccaac   360
cacatcaacg tgatggtcaa gttccccagc atcgtggaag aggaactcca gttcgacctg   420
agcctggtca tcgaggaaca gtccgagggc atcgtgaaga gcacaagcc cgagatcaag   480
ggcaacatgt ccggcaactt cacctacatc atcgacaagc tgatccccaa caccaactac   540
tgcgtgtccg tgtacctgga acactccgat gagcaggccg tgatcaagtc ccctctgaag   600
tgtaccctgc tgcctcctgg ccaagagtct gagtctgccg agtctgctaa a            651
```

<210> SEQ ID NO 6
<211> LENGTH: 217
<212> TYPE: PRT
<213> ORGANISM: Artificial Sequence
<220> FEATURE:
<223> OTHER INFORMATION: IFNAR2 ExtraCellular Domain

<400> SEQUENCE: 6

```
Ile Ser Tyr Asp Ser Pro Asp Tyr Thr Asp Glu Ser Cys Thr Phe Lys
1               5                   10                  15

Ile Ser Leu Arg Asn Phe Arg Ser Ile Leu Ser Trp Glu Leu Lys Asn
            20                  25                  30

His Ser Ile Val Pro Thr His Tyr Thr Leu Leu Tyr Thr Ile Met Ser
        35                  40                  45

Lys Pro Glu Asp Leu Lys Val Val Lys Asn Cys Ala Asn Thr Thr Arg
    50                  55                  60
```

Ser Phe Cys Asp Leu Thr Asp Glu Trp Arg Ser Thr His Glu Ala Tyr
65                  70                  75                  80

Val Thr Val Leu Glu Gly Phe Ser Gly Asn Thr Thr Leu Phe Ser Cys
                85                  90                  95

Ser His Asn Phe Trp Leu Ala Ile Asp Met Ser Phe Glu Pro Pro Glu
            100                 105                 110

Phe Glu Ile Val Gly Phe Thr Asn His Ile Asn Val Met Val Lys Phe
            115                 120                 125

Pro Ser Ile Val Glu Glu Leu Gln Phe Asp Leu Ser Leu Val Ile
            130                 135             140

Glu Glu Gln Ser Glu Gly Ile Val Lys Lys His Lys Pro Glu Ile Lys
145                 150                 155                 160

Gly Asn Met Ser Gly Asn Phe Thr Tyr Ile Ile Asp Lys Leu Ile Pro
                165                 170                 175

Asn Thr Asn Tyr Cys Val Ser Val Tyr Leu Glu His Ser Asp Glu Gln
            180                 185                 190

Ala Val Ile Lys Ser Pro Leu Lys Cys Thr Leu Leu Pro Pro Gly Gln
            195                 200                 205

Glu Ser Glu Ser Ala Glu Ser Ala Lys
    210                 215

<210> SEQ ID NO 7
<211> LENGTH: 696
<212> TYPE: DNA
<213> ORGANISM: Artificial Sequence
<220> FEATURE:
<223> OTHER INFORMATION: Synthetic: FC-WT

<400> SEQUENCE: 7
cccaagagct gcgacaagac ccacacctgt ccccctgcc ctgcccctga actgctgggc      60
ggacccagcg tgttcctgtt cccccaaag cccaaggaca ccctgatgat cagccggacc     120
cccgaagtga cctgcgtggt ggtggacgtg tcccacgagg accctgaagt gaagttcaat    180
tggtacgtgg acggcgtgga agtgcacaac gccaagacca gcccagaga ggaacagtac    240 aacagcacct accgggtggt gtccgtgctg accgtgctgc accaggactg gctgaacggc    300
aaagagtaca gtgcaaggt gtccaacaag gccctgcctg ccccatcga gaaaaccatc     360 agcaaggcca agggccagcc ccgcgagccc caggtgtaca cactgccccc cagccgggac    420
gagctgacca gaaccaggt gtccctgacc tgcctggtga aaggcttcta ccccagcgat    480
atcgccgtgg aatgggagag caacggccag ccgagaaca actacaagac cacccccct    540 gtgctggaca gcgacggctc attcttcctg tacagcaagc tgaccgtgga caagagccgg    600
tggcagcagg gcaacgtgtt cagctgcagc gtgatgcacg aggccctgca caaccactac    660
acccagaagt ccctgagcct gagccccggc aagtag                              696

<210> SEQ ID NO 8
<211> LENGTH: 231
<212> TYPE: PRT
<213> ORGANISM: Artificial Sequence
<220> FEATURE:
<223> OTHER INFORMATION: Synthetic: FC-WT

<400> SEQUENCE: 8

Pro Lys Ser Cys Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys

```
                    20                  25                  30

Asp Thr Leu Met Ile Ser Arg Thr Pro Glu Val Thr Cys Val Val Val
            35                  40                  45

Asp Val Ser His Glu Asp Pro Glu Val Lys Phe Asn Trp Tyr Val Asp
        50                  55                  60

Gly Val Glu Val His Asn Ala Lys Thr Lys Pro Arg Glu Glu Gln Tyr
 65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 9
<211> LENGTH: 18
<212> TYPE: DNA
<213> ORGANISM: Artificial Sequence
<220> FEATURE:
<223> OTHER INFORMATION: Synthetic: Linker

<400> SEQUENCE: 9
atcgagggcc ggatggac                                                  18

<210> SEQ ID NO 10
<211> LENGTH: 6
<212> TYPE: PRT
<213> ORGANISM: Artificial Sequence
<220> FEATURE:
<223> OTHER INFORMATION: Synthetic: Linker

<400> SEQUENCE: 10

Ile Glu Gly Arg Met Asp
1               5

<210> SEQ ID NO 11
<211> LENGTH: 696
<212> TYPE: DNA
<213> ORGANISM: Artificial Sequence
<220> FEATURE:
<223> OTHER INFORMATION: Synthetic: FC-EW

<400> SEQUENCE: 11
cccaagagct gcgacaagac ccacacctgt cccccctgcc ctgcccctga actgctgggc    60
ggacccagcg tgttcctgtt ccccccaaag cccaaggaca ccctgatgat cagccggacc   120
```

```
cccgaagtga cctgcgtggt ggtggacgtg tcccacgagg accctgaagt gaagttcaat    180
tggtacgtgg acggcgtgga agtgcacaac gccaagacca agcccagaga ggaacagtac    240
aacagcacct accgggtggt gtccgtgctg accgtgctgc accaggactg gctgaacggc    300
aaagagtaca agtgcaaggt gtccaacaag gccctgcctg cccccatcga aaaaccatc     360 agcaaggcca agggccagcc ccgcgagccc caggtgtaca cactgccccc cagccgggac    420
gagctgaccg agaaccaggt gtccctgacc tgcctggtga aaggcttcta ccccagcgat    480
atcgccgtgg aatgggagag caacggccag cccgagaaca actacaagac caccccccct    540
gtgctggaca gcgacggctc attcttcctg tacagctggc tgaccgtgga caagagccgg    600
tggcagcagg gcaacgtgtt cagctgcagc gtgatgcacg aggccctgca caaccactac    660
acccagaagt ccctgagcct gagccccggc aagtag                              696
```

<210> SEQ ID NO 12
<211> LENGTH: 231
<212> TYPE: PRT
<213> ORGANISM: Artificial Sequence
<220> FEATURE:
<223> OTHER INFORMATION: Synthetic: FC-EW

<400> SEQUENCE: 12

```
Pro Lys Ser Cys Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Glu
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Trp Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230
```

<210> SEQ ID NO 13
<211> LENGTH: 696

<212> TYPE: DNA
<213> ORGANISM: Artificial Sequence
<220> FEATURE:
<223> OTHER INFORMATION: Synthetic: FC-RVT

<400> SEQUENCE: 13

```
cccaagagct gcgacaagac ccacacctgt ccccccctgcc ctgcccctga actgctgggc      60
ggacccagcg tgttcctgtt ccccccaaag cccaaggaca ccctgatgat cagccggacc     120
cccgaagtga cctgcgtggt ggtggacgtg tcccacgagg accctgaagt gaagttcaat     180
tggtacgtgg acggcgtgga agtgcacaac gccaagacca gcccagaga ggaacagtac      240
aacagcaccT accgggtggt gtccgtgctg accgtgctgc accaggactg gctgaacggc     300
aaagagtaca agtgcaaggt gtccaacaag gccctgcctg ccccatcga gaaaaccatc      360
agcaaggcca agggccagcc ccgcgagccc cgggtgtaca cactgccccc cagccgggac     420
gagctgacca agaaccaggt gtccctgacc tgcctggtga aaggcttcta ccccagcgat     480
atcgccgtgg aatgggagag caacggccag cccgagaaca actacaagac cacccccct      540
gtgctggtca gcgacggctc attcaccctg tacagcaagc tgaccgtgga caagagccgg     600
tggcagcagg gcaacgtgtt cagctgcagc gtgatgcacg aggccctgca caaccactac     660
acccagaagt ccctgagcct gagccccggc aagtag                               696
```

<210> SEQ ID NO 14
<211> LENGTH: 231
<212> TYPE: PRT
<213> ORGANISM: Artificial Sequence
<220> FEATURE:
<223> OTHER INFORMATION: Synthetic: FC-RVT

<400> SEQUENCE: 14

```
Pro Lys Ser Cys Asp Lys Thr His Thr Cys Pro Pro Cys Pro Ala Pro
1               5                   10                  15
Glu Leu Leu Gly Gly Pro Ser Val Phe Leu Phe Pro Pro Lys Pro Lys
            20                  25                  30
Asp Thr Leu Met Ile Ser Arg Thr Pro Glu Val Thr Cys Val Val Val
        35                  40                  45
Asp Val Ser His Glu Asp Pro Glu Val Lys Phe Asn Trp Tyr Val Asp
    50                  55                  60
Gly Val Glu Val His Asn Ala Lys Thr Lys Pro Arg Glu Glu Gln Tyr
65                  70                  75                  80
Asn Ser Thr Tyr Arg Val Val Ser Val Leu Thr Val Leu His Gln Asp
                85                  90                  95
Trp Leu Asn Gly Lys Glu Tyr Lys Cys Lys Val Ser Asn Lys Ala Leu
            100                 105                 110
Pro Ala Pro Ile Glu Lys Thr Ile Ser Lys Ala Lys Gly Gln Pro Arg
        115                 120                 125
Glu Pro Arg Val Tyr Thr Leu Pro Pro Ser Arg Asp Glu Leu Thr Lys
    130                 135                 140
Asn Gln Val Ser Leu Thr Cys Leu Val Lys Gly Phe Tyr Pro Ser Asp
145                 150                 155                 160
Ile Ala Val Glu Trp Glu Ser Asn Gly Gln Pro Glu Asn Asn Tyr Lys
                165                 170                 175
Thr Thr Pro Pro Val Leu Val Ser Asp Gly Ser Phe Thr Leu Tyr Ser
            180                 185                 190
Lys Leu Thr Val Asp Lys Ser Arg Trp Gln Gln Gly Asn Val Phe Ser
        195                 200                 205
```

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 15
<211> LENGTH: 783
<212> TYPE: DNA
<213> ORGANISM: Artificial Sequence
<220> FEATURE:
<223> OTHER INFORMATION: Synthetic: Linker-FC WT

<400> SEQUENCE: 15
gccaccatgt ggtggcgtct gtggtggctg ctgcttctgc tgttgctgct gtggcctatg      60
gtctgggcca tcgagggccg gatggacccc aagagctgcg acaagaccca cacctgtccc     120
ccctgccctg cccctgaact gctgggcgga cccagcgtgt tcctgttccc cccaaagccc     180
aaggacaccc tgatgatcag ccggaccccc gaagtgacct gcgtggtggt ggacgtgtcc     240
cacgaggacc ctgaagtgaa gttcaattgg tacgtggacg gcgtggaagt gcacaacgcc     300
aagaccaagc ccagagagga acagtacaac agcacctacc gggtggtgtc cgtgctgacc     360
gtgctgcacc aggactggct gaacggcaaa gagtacaagt gcaaggtgtc caacaaggcc     420
ctgcctgccc ccatcgagaa aaccatcagc aaggccaagg gccagccccg cgagccccag     480
gtgtacacac tgcccccag ccgggacgag ctgaccaaga accaggtgtc cctgacctgc     540
ctggtgaaag gcttctaccc cagcgatatc gccgtggaat gggagagcaa cggccagccc     600
gagaacaact acaagaccac ccccctgtg ctggacagcg acggctcatt cttcctgtac     660
agcaagctga ccgtggacaa gagccggtgg cagcagggca acgtgttcag ctgcagcgtg     720
atgcacgagg ccctgcacaa ccactacacc cagaagtccc tgagcctgag ccccggcaag     780
tga                                                                   783

<210> SEQ ID NO 16
<211> LENGTH: 260
<212> TYPE: PRT
<213> ORGANISM: Artificial Sequence
<220> FEATURE:
<223> OTHER INFORMATION: Synthetic: Linker-FC WT

<400> SEQUENCE: 16

Ala Thr Met Trp Trp Arg Leu Trp Trp Leu Leu Leu Leu Leu Leu
1                   5                   10                  15

Leu Trp Pro Met Val Trp Ala Ile Glu Gly Arg Met Asp Pro Lys Ser
                20                  25                  30

Cys Asp Lys Thr His Thr Cys Pro Pro Cys Pro Ala Pro Glu Leu Leu
            35                  40                  45

Gly Gly Pro Ser Val Phe Leu Phe Pro Pro Lys Pro Lys Asp Thr Leu
        50                  55                  60

Met Ile Ser Arg Thr Pro Glu Val Thr Cys Val Val Val Asp Val Ser
65                  70                  75                  80

His Glu Asp Pro Glu Val Lys Phe Asn Trp Tyr Val Asp Gly Val Glu
                85                  90                  95

Val His Asn Ala Lys Thr Lys Pro Arg Glu Glu Gln Tyr Asn Ser Thr
            100                 105                 110

Tyr Arg Val Val Ser Val Leu Thr Val Leu His Gln Asp Trp Leu Asn
        115                 120                 125

Gly Lys Glu Tyr Lys Cys Lys Val Ser Asn Lys Ala Leu Pro Ala Pro
        130                 135                 140

Ile Glu Lys Thr Ile Ser Lys Ala Lys Gly Gln Pro Arg Glu Pro Gln
145                 150                 155                 160

Val Tyr Thr Leu Pro Pro Ser Arg Asp Glu Leu Thr Lys Asn Gln Val
                165                 170                 175

Ser Leu Thr Cys Leu Val Lys Gly Phe Tyr Pro Ser Asp Ile Ala Val
            180                 185                 190

Glu Trp Glu Ser Asn Gly Gln Pro Glu Asn Asn Tyr Lys Thr Thr Pro
        195                 200                 205

Pro Val Leu Asp Ser Asp Gly Ser Phe Phe Leu Tyr Ser Lys Leu Thr
    210                 215                 220

Val Asp Lys Ser Arg Trp Gln Gln Gly Asn Val Phe Ser Cys Ser Val
225                 230                 235                 240

Met His Glu Ala Leu His Asn His Tyr Thr Gln Lys Ser Leu Ser Leu
                245                 250                 255

Ser Pro Gly Lys
        260

<210> SEQ ID NO 17
<211> LENGTH: 783
<212> TYPE: DNA
<213> ORGANISM: Artificial Sequence
<220> FEATURE:
<223> OTHER INFORMATION: Synthetic: Linker-FC EW

<400> SEQUENCE: 17
gccaccatgt ggtggcgtct gtggtggctg ctgcttctgc tgttgctgct gtggcctatg      60
gtctgggcca tcgagggccg gatggacccc aagagctgcg acaagaccca cacctgtccc     120
ccctgccctg cccctgaact gctgggcgga cccagcgtgt tcctgttccc cccaaagccc     180
aaggacaccc tgatgatcag ccggaccccc gaagtgacct gcgtggtggt ggacgtgtcc     240
cacgaggacc ctgaagtgaa gttcaattgg tacgtggacg gcgtggaagt gcacaacgcc     300
aagaccaagc ccagagagga acagtacaac agcacctacc gggtggtgtc cgtgctgacc     360
gtgctgcacc aggactggct gaacggcaaa gagtacaagt gcaaggtgtc caacaaggcc     420
ctgcctgccc ccatcgagaa accatcagc aaggccaagg gccagccccg cgagccccag     480
gtgtacacac tgcccccag ccgggacgag ctgaccgaga accaggtgtc cctgacctgc     540
ctggtgaaag gcttctaccc cagcgatatc gccgtggaat gggagagcaa cggccagccc     600
gagaacaact acaagaccac ccccctgtg ctggacagcg acggctcatt cttcctgtac     660
agctggctga ccgtggacaa gagccggtgg cagcagggca acgtgttcag ctgcagcgtg     720
atgcacgagg ccctgcacaa ccactacacc cagaagtccc tgagcctgag ccccggcaag     780
tag                                                                    783

<210> SEQ ID NO 18
<211> LENGTH: 260
<212> TYPE: PRT
<213> ORGANISM: Artificial Sequence
<220> FEATURE:
<223> OTHER INFORMATION: Synthetic: Linker-FC EW

<400> SEQUENCE: 18

Ala Thr Met Trp Trp Arg Leu Trp Trp Leu Leu Leu Leu Leu Leu Leu
1               5                   10                  15

Leu Trp Pro Met Val Trp Ala Ile Glu Gly Arg Met Asp Pro Lys Ser

```
                20                  25                  30

Cys Asp Lys Thr His Thr Cys Pro Pro Cys Pro Ala Pro Glu Leu Leu
            35                  40                  45

Gly Gly Pro Ser Val Phe Leu Phe Pro Pro Lys Pro Lys Asp Thr Leu
        50                  55                  60

Met Ile Ser Arg Thr Pro Glu Val Thr Cys Val Val Val Asp Val Ser
65                  70                  75                  80

His Glu Asp Pro Glu Val Lys Phe Asn Trp Tyr Val Asp Gly Val Glu
                85                  90                  95

Val His Asn Ala Lys Thr Lys Pro Arg Glu Glu Gln Tyr Asn Ser Thr
            100                 105                 110

Tyr Arg Val Val Ser Val Leu Thr Val Leu His Gln Asp Trp Leu Asn
        115                 120                 125

Gly Lys Glu Tyr Lys Cys Lys Val Ser Asn Lys Ala Leu Pro Ala Pro
    130                 135                 140

Ile Glu Lys Thr Ile Ser Lys Ala Lys Gly Gln Pro Arg Glu Pro Gln
145                 150                 155                 160

Val Tyr Thr Leu Pro Pro Ser Arg Asp Glu Leu Thr Glu Asn Gln Val
                165                 170                 175

Ser Leu Thr Cys Leu Val Lys Gly Phe Tyr Pro Ser Asp Ile Ala Val
            180                 185                 190

Glu Trp Glu Ser Asn Gly Gln Pro Glu Asn Asn Tyr Lys Thr Thr Pro
        195                 200                 205

Pro Val Leu Asp Ser Asp Gly Ser Phe Phe Leu Tyr Ser Trp Leu Thr
    210                 215                 220

Val Asp Lys Ser Arg Trp Gln Gln Gly Asn Val Phe Ser Cys Ser Val
225                 230                 235                 240

Met His Glu Ala Leu His Asn His Tyr Thr Gln Lys Ser Leu Ser Leu
                245                 250                 255

Ser Pro Gly Lys
            260

<210> SEQ ID NO 19
<211> LENGTH: 783
<212> TYPE: DNA
<213> ORGANISM: Artificial Sequence
<220> FEATURE:
<223> OTHER INFORMATION: Synthetic: Linker-FC RVT

<400> SEQUENCE: 19
gccaccatgt ggtggcgtct gtggtggctg ctgcttctgc tgttgctgct gtggcctatg      60
gtctgggcca tcgagggccg gatggacccc aagagctgcg acaagaccca cacctgtccc     120
ccctgccctg cccctgaact gctgggcgga cccagcgtgt tcctgttccc cccaaagccc     180
aaggacaccc tgatgatcag ccggaccccc gaagtgacct gcgtggtggt ggacgtgtcc     240
cacgaggacc ctgaagtgaa gttcaattgg tacgtggacg gcgtggaagt gcacaacgcc     300
aagaccaagc ccagagagga acagtacaac agcacctacc gggtggtgtc cgtgctgacc     360
gtgctgcacc aggactggct gaacggcaaa gagtacaagt gcaaggtgtc caacaaggcc     420
ctgcctgccc ccatcgagaa aaccatcagc aaggccaagg gccagccccg cgagccccag     480
gtgtacacac tgcccccaag ccgggacgag ctgaccaaga accaggtgtc cctgacctgc     540
ctggtgaaag gcttctaccc cagcgatatc gccgtggaat gggagagcaa cggccagccc     600
gagaacaact acaagaccac cccccctgtg ctggtcagcg acggctcatt cacccctgtac    660
```

```
agcaagctga ccgtggacaa gagccggtgg cagcagggca acgtgttcag ctgcagcgtg      720
atgcacgagg ccctgcacaa ccactacacc cagaagtccc tgagcctgag ccccggcaag      780
tag                                                                    783
```

<210> SEQ ID NO 20
<211> LENGTH: 260
<212> TYPE: PRT
<213> ORGANISM: Artificial Sequence
<220> FEATURE:
<223> OTHER INFORMATION: Synthetic: Linker-FC RVT

<400> SEQUENCE: 20

```
Ala Thr Met Trp Trp Arg Leu Trp Trp Leu Leu Leu Leu Leu Leu
1               5                   10                  15

Leu Trp Pro Met Val Trp Ala Ile Glu Gly Arg Met Asp Pro Lys Ser
            20                  25                  30

Cys Asp Lys Thr His Thr Cys Pro Pro Cys Pro Ala Pro Glu Leu Leu
        35                  40                  45

Gly Gly Pro Ser Val Phe Leu Phe Pro Pro Lys Pro Lys Asp Thr Leu
    50                  55                  60

Met Ile Ser Arg Thr Pro Glu Val Thr Cys Val Val Val Asp Val Ser
65                  70                  75                  80

His Glu Asp Pro Glu Val Lys Phe Asn Trp Tyr Val Asp Gly Val Glu
                85                  90                  95

Val His Asn Ala Lys Thr Lys Pro Arg Glu Glu Gln Tyr Asn Ser Thr
            100                 105                 110

Tyr Arg Val Val Ser Val Leu Thr Val Leu His Gln Asp Trp Leu Asn
        115                 120                 125

Gly Lys Glu Tyr Lys Cys Lys Val Ser Asn Lys Ala Leu Pro Ala Pro
    130                 135                 140

Ile Glu Lys Thr Ile Ser Lys Ala Lys Gly Gln Pro Arg Glu Pro Arg
145                 150                 155                 160

Val Tyr Thr Leu Pro Pro Ser Arg Asp Glu Leu Thr Lys Asn Gln Val
                165                 170                 175

Ser Leu Thr Cys Leu Val Lys Gly Phe Tyr Pro Ser Asp Ile Ala Val
            180                 185                 190

Glu Trp Glu Ser Asn Gly Gln Pro Glu Asn Asn Tyr Lys Thr Thr Pro
        195                 200                 205

Pro Val Leu Val Ser Asp Gly Ser Phe Thr Leu Tyr Ser Lys Leu Thr
    210                 215                 220

Val Asp Lys Ser Arg Trp Gln Gln Gly Asn Val Phe Ser Cys Ser Val
225                 230                 235                 240

Met His Glu Ala Leu His Asn His Tyr Thr Gln Lys Ser Leu Ser Leu
                245                 250                 255

Ser Pro Gly Lys
            260
```

<210> SEQ ID NO 21
<211> LENGTH: 2010
<212> TYPE: DNA
<213> ORGANISM: Artificial Sequence
<220> FEATURE:
<223> OTHER INFORMATION: Synthetic: IFNAR1-Linker-FC WT

<400> SEQUENCE: 21

```
gccaccatgt ggtggcgtct gtggtggctg ctgcttctgc tgttgctgct gtggcctatg       60
```

```
gtctgggcca agaacctgaa gtcccctcag aaagtggaag tggacatcat cgacgacaac    120
ttcatcctgc ggtggaacag atccgacgag tccgtgggca acgtgacctt cagcttcgac    180
taccagaaaa ccggcatgga caactggatc aagctgtccg gctgccagaa catcacctct    240
accaagtgca acttctccag cctgaagctg aacgtgtacg aggaaatcaa gctgcggatc    300
cgggccgaga agagaacac cagcagttgg tacgaggtgg acagcttcac ccctttcaga    360
aaggcccaga tcggcctcc tgaagtgcac ctggaagccg aggataaggc catcgtgatc    420
cacatcagcc ccggcaccaa ggactctgtg atgtgggctc tcgacggcct gtccttcacc    480
tacagcctgg tcatctggaa gaactcctcc ggcgtggaag agagaatcga gaacatctac    540
tcccggcaca agatctacaa gctgagcccc gagacaacct actgcctgaa agtgaaggcc    600
gctctgctga cctcctggaa gatcggcgtg tactctcccg tgcactgcat caagaccacc    660
gtggaaaacg agctgcctcc tccagagaac atcgaggtgt ccgtgcagaa ccagaactac    720
gtgctgaagt gggactacac ctacgccaac atgaccttc aggtgcagtg gctgcacgct    780
tttctgaagc ggaaccctgg caaccacctg tacaagtgga agcagattcc cgactgcgag    840
aacgtgaaaa ccacacagtg cgtgttccct cagaacgtgt ccagaaggg catctacctg    900 ctgagagtgc aggcctccga cggcaacaac accagctttt ggagcgaaga gatcaagttc    960
gataccgaga tccaggcctt cctgctgcct ccagtgttca acatcagatc cctgtccgac   1020
tccttccaca tctacatcgg cgctcctaag cagtccggca cacccctgt gatccaggac   1080 taccctctga tctacgagat catcttctgg gagaacacct ccaacgccga gcggaagatc   1140
atcgagaaga aaaccgacgt gaccgtgcct aacctgaagc tctgaccgt gtactgcgtg   1200 aaggctaggg cccacaccat ggacgaaaag ctgaacaagt cctccgtgtt ctccgacgcc   1260
gtgtgcgaaa agaccaagcc aggcaacacc tctaaaatcg agggccggat ggaccccaag   1320
agctgcgaca gacccacac ctgtccccc tgccctgccc ctgaactgct gggcggaccc   1380
agcgtgttcc tgttccccc aaagcccaag gacaccctga tgatcagccg gacccccgaa   1440
gtgacctgcg tggtggtgga cgtgtcccac gaggaccctg aagtgaagtt caattggtac   1500
gtggacggcg tggaagtgca caacgccaag accaagccca gagaggaaca gtacaacagc   1560
acctaccggg tggtgtccgt gctgaccgtg ctgcaccagg actggctgaa cggcaaagag   1620
tacaagtgca aggtgtccaa caaggccctg cctgcccca tcgagaaaac catcagcaag   1680
gccaagggcc agccccgcga gccccaggtg tacacactgc cccccagccg ggacgagctg   1740
accaagaacc aggtgtccct gacctgcctg gtgaaaggct ctaccccag cgatatcgcc   1800 gtggaatggg agagcaacgg ccagcccgag aacaactaca agaccacccc cctgtgctg   1860 gacagcgacg gctcattctt cctgtacagc aagctgaccg tggacaagag ccggtggcag   1920
cagggcaacg tgttcagctg cagcgtgatg cacgaggccc tgcacaacca ctacacccag   1980
aagtccctga gcctgagccc cggcaagtga                                    2010
```

<210> SEQ ID NO 22
<211> LENGTH: 669
<212> TYPE: PRT
<213> ORGANISM: Artificial Sequence
<220> FEATURE:
<223> OTHER INFORMATION: Synthetic: IFNAR1-Linker-FC WT

<400> SEQUENCE: 22

```
Ala Thr Met Trp Trp Arg Leu Trp Trp Leu Leu Leu Leu Leu Leu Leu
1               5                   10                  15
```

-continued

Leu Trp Pro Met Val Trp Ala Lys Asn Leu Lys Ser Pro Gln Lys Val
            20                  25                  30

Glu Val Asp Ile Ile Asp Asn Phe Ile Leu Arg Trp Asn Arg Ser
        35                  40                  45

Asp Glu Ser Val Gly Asn Val Thr Phe Ser Phe Asp Tyr Gln Lys Thr
    50                  55                  60

Gly Met Asp Asn Trp Ile Lys Leu Ser Gly Cys Gln Asn Ile Thr Ser
65                  70                  75                  80

Thr Lys Cys Asn Phe Ser Ser Leu Lys Leu Asn Val Tyr Glu Glu Ile
                85                  90                  95

Lys Leu Arg Ile Arg Ala Glu Lys Glu Asn Thr Ser Ser Trp Tyr Glu
            100                 105                 110

Val Asp Ser Phe Thr Pro Phe Arg Lys Ala Gln Ile Gly Pro Pro Glu
        115                 120                 125

Val His Leu Glu Ala Glu Asp Lys Ala Ile Val Ile His Ile Ser Pro
    130                 135                 140

Gly Thr Lys Asp Ser Val Met Trp Ala Leu Asp Gly Leu Ser Phe Thr
145                 150                 155                 160

Tyr Ser Leu Val Ile Trp Lys Asn Ser Ser Gly Val Glu Glu Arg Ile
                165                 170                 175

Glu Asn Ile Tyr Ser Arg His Lys Ile Tyr Lys Leu Ser Pro Glu Thr
            180                 185                 190

Thr Tyr Cys Leu Lys Val Lys Ala Ala Leu Leu Thr Ser Trp Lys Ile
        195                 200                 205

Gly Val Tyr Ser Pro Val His Cys Ile Lys Thr Thr Val Glu Asn Glu
    210                 215                 220

Leu Pro Pro Pro Glu Asn Ile Glu Val Ser Val Gln Asn Gln Asn Tyr
225                 230                 235                 240

Val Leu Lys Trp Asp Tyr Thr Tyr Ala Asn Met Thr Phe Gln Val Gln
                245                 250                 255

Trp Leu His Ala Phe Leu Lys Arg Asn Pro Gly Asn His Leu Tyr Lys
            260                 265                 270

Trp Lys Gln Ile Pro Asp Cys Glu Asn Val Lys Thr Thr Gln Cys Val
        275                 280                 285

Phe Pro Gln Asn Val Phe Gln Lys Gly Ile Tyr Leu Leu Arg Val Gln
    290                 295                 300

Ala Ser Asp Gly Asn Asn Thr Ser Phe Trp Ser Glu Glu Ile Lys Phe
305                 310                 315                 320

Asp Thr Glu Ile Gln Ala Phe Leu Leu Pro Pro Val Phe Asn Ile Arg
                325                 330                 335

Ser Leu Ser Asp Ser Phe His Ile Tyr Ile Gly Ala Pro Lys Gln Ser
            340                 345                 350

Gly Asn Thr Pro Val Ile Gln Asp Tyr Pro Leu Ile Tyr Glu Ile Ile
        355                 360                 365

Phe Trp Glu Asn Thr Ser Asn Ala Glu Arg Lys Ile Ile Glu Lys Lys
    370                 375                 380

Thr Asp Val Thr Val Pro Asn Leu Lys Pro Leu Thr Val Tyr Cys Val
385                 390                 395                 400

Lys Ala Arg Ala His Thr Met Asp Glu Lys Leu Asn Lys Ser Ser Val
                405                 410                 415

Phe Ser Asp Ala Val Cys Glu Lys Thr Lys Pro Gly Asn Thr Ser Lys
            420                 425                 430

Ile Glu Gly Arg Met Asp Pro Lys Ser Cys Asp Lys Thr His Thr Cys

|   |   |   | 435 |   |   |   | 440 |   |   |   | 445 |   |
|---|---|---|---|---|---|---|---|---|---|---|---|---|

Pro Pro Cys Pro Ala Pro Glu Leu Leu Gly Gly Pro Ser Val Phe Leu
            450                 455                 460

Phe Pro Pro Lys Pro Lys Asp Thr Leu Met Ile Ser Arg Thr Pro Glu
465                 470                 475                 480

Val Thr Cys Val Val Val Asp Val Ser His Glu Asp Pro Glu Val Lys
                    485                 490                 495

Phe Asn Trp Tyr Val Asp Gly Val Glu Val His Asn Ala Lys Thr Lys
                500                 505                 510

Pro Arg Glu Glu Gln Tyr Asn Ser Thr Tyr Arg Val Val Ser Val Leu
            515                 520                 525

Thr Val Leu His Gln Asp Trp Leu Asn Gly Lys Glu Tyr Lys Cys Lys
        530                 535                 540

Val Ser Asn Lys Ala Leu Pro Ala Pro Ile Glu Lys Thr Ile Ser Lys
545                 550                 555                 560

Ala Lys Gly Gln Pro Arg Glu Pro Gln Val Tyr Thr Leu Pro Pro Ser
                565                 570                 575

Arg Asp Glu Leu Thr Lys Asn Gln Val Ser Leu Thr Cys Leu Val Lys
            580                 585                 590

Gly Phe Tyr Pro Ser Asp Ile Ala Val Glu Trp Glu Ser Asn Gly Gln
        595                 600                 605

Pro Glu Asn Asn Tyr Lys Thr Thr Pro Pro Val Leu Asp Ser Asp Gly
    610                 615                 620

Ser Phe Phe Leu Tyr Ser Lys Leu Thr Val Asp Lys Ser Arg Trp Gln
625                 630                 635                 640

Gln Gly Asn Val Phe Ser Cys Ser Val Met His Glu Ala Leu His Asn
                645                 650                 655

His Tyr Thr Gln Lys Ser Leu Ser Leu Ser Pro Gly Lys
            660                 665

<210> SEQ ID NO 23
<211> LENGTH: 2010
<212> TYPE: DNA
<213> ORGANISM: Artificial Sequence
<220> FEATURE:
<223> OTHER INFORMATION: Synthetic: IFNAR1-Linker-FC EW

<400> SEQUENCE: 23

```
gccaccatgt ggtggcgtct gtggtggctg ctgcttctgc tgttgctgct gtggcctatg      60
gtctgggcca agaacctgaa gtcccctcag aaagtggaag tggacatcat cgacgacaac     120
ttcatcctgc ggtggaacag atccgacgag tccgtgggca acgtgacctt cagcttcgac     180
taccagaaaa ccggcatgga caactggatc aagctgtccg ctgccagaa catcaccctct     240
accaagtgca acttctccag cctgaagctg aacgtgtacg aggaaatcaa gctgcggatc     300
cgggccgaga agagaacac cagcagttgg tacgaggtgg acagcttcac cccctttcaga     360
aaggcccaga tcgccctcc tgaagtgcac ctggaagccg aggataaggc catcgtgatc     420
cacatcagcc ccggcaccaa ggactctgtg atgtgggctc tcgacggcct gtccttcacc     480
tacagcctgg tcatctggaa gaactcctcc ggcgtggaag agaatcga aacatctac         540
tcccggcaca agatctacaa gctgagcccc gagacaacct actgcctgaa agtgaaggcc     600
gctctgctga cctcctggaa gatcggcgtg tactctcccg tgcactgcat caagaccacc     660
gtggaaaacg agctgcctcc tcagagaaac atcgaggtgt ccgtgcagaa ccagaactac     720
gtgctgaagt gggactacac ctacgccaac atgaccttc aggtgcagtg gctgcacgct     780
```

```
tttctgaagc ggaaccctgg caaccacctg tacaagtgga agcagattcc cgactgcgag      840
aacgtgaaaa ccacacagtg cgtgttccct cagaacgtgt tccagaaggg catctacctg      900
ctgagagtgc aggcctccga cggcaacaac accagctttt ggagcgaaga gatcaagttc      960
gataccgaga tccaggcctt cctgctgcct ccagtgttca acatcagatc cctgtccgac     1020
tccttccaca tctacatcgg cgctcctaag cagtccggca caccctgt gatccaggac       1080
taccctctga tctacgagat catcttctgg gagaacacct ccaacgccga gcggaagatc     1140
atcgagaaga aaccgacgt gaccgtgcct aacctgaagc tcctgaccgt gtactgcgtg      1200
aaggctaggg cccacaccat ggacgaaaag ctgaacaagt cctccgtgtt ctccgacgcc     1260
gtgtgcgaaa agaccaagcc aggcaacacc tctaaaatcg agggccggat ggaccccaag     1320
agctgcgaca gacccacac ctgtcccccc tgccctgccc ctgaactgct gggcggaccc      1380
agcgtgttcc tgttcccccc aaagcccaag gacaccctga tgatcagccg gacccccgaa     1440
gtgacctgcg tggtggtgga cgtgtcccac gaggaccctg aagtgaagtt caattggtac     1500
gtggacggcg tggaagtgca caacgccaag accaagccca gagaggaaca gtacaacagc     1560
acctaccggg tggtgtccgt gctgaccgtg ctgcaccagg actggctgaa cggcaaagag     1620
tacaagtgca aggtgtccaa caaggccctg cctgcccca tcgagaaaac catcagcaag      1680
gccaagggcc agccccgcga gccccaggtg tacacactgc cccccagccg ggacgagctg     1740
accgagaacc aggtgtccct gacctgcctg gtgaaaggct ctaccccag cgatatcgcc      1800
gtggaatggg agagcaacgg ccagcccgag aacaactaca agaccacccc ccctgtgctg     1860
gacagcgacg gctcattctt cctgtacagc tggctgaccg tggacaagag ccggtggcag     1920
cagggcaacg tgttcagctg cagcgtgatg cacgaggccc tgcacaacca ctacacccag     1980
aagtccctga gcctgagccc cggcaagtag                                      2010
```

<210> SEQ ID NO 24
<211> LENGTH: 669
<212> TYPE: PRT
<213> ORGANISM: Artificial Sequence
<220> FEATURE:
<223> OTHER INFORMATION: Synthetic: IFNAR1-Linker-FC EW

<400> SEQUENCE: 24

```
Ala Thr Met Trp Trp Arg Leu Trp Trp Leu Leu Leu Leu Leu Leu Leu
1               5                   10                  15

Leu Trp Pro Met Val Trp Ala Lys Asn Leu Lys Ser Pro Gln Lys Val
            20                  25                  30

Glu Val Asp Ile Ile Asp Asp Asn Phe Ile Leu Arg Trp Asn Arg Ser
        35                  40                  45

Asp Glu Ser Val Gly Asn Val Thr Phe Ser Phe Asp Tyr Gln Lys Thr
    50                  55                  60

Gly Met Asp Asn Trp Ile Lys Leu Ser Gly Cys Gln Asn Ile Thr Ser
65                  70                  75                  80

Thr Lys Cys Asn Phe Ser Ser Leu Lys Leu Asn Val Tyr Glu Glu Ile
                85                  90                  95

Lys Leu Arg Ile Arg Ala Glu Lys Glu Asn Thr Ser Ser Trp Tyr Glu
            100                 105                 110

Val Asp Ser Phe Thr Pro Phe Arg Lys Ala Gln Ile Gly Pro Pro Glu
        115                 120                 125

Val His Leu Glu Ala Glu Asp Lys Ala Ile Val Ile His Ile Ser Pro
    130                 135                 140
```

```
Gly Thr Lys Asp Ser Val Met Trp Ala Leu Asp Gly Leu Ser Phe Thr
145                 150                 155                 160

Tyr Ser Leu Val Ile Trp Lys Asn Ser Ser Gly Val Glu Glu Arg Ile
                165                 170                 175

Glu Asn Ile Tyr Ser Arg His Lys Ile Tyr Lys Leu Ser Pro Glu Thr
            180                 185                 190

Thr Tyr Cys Leu Lys Val Lys Ala Ala Leu Leu Thr Ser Trp Lys Ile
        195                 200                 205

Gly Val Tyr Ser Pro Val His Cys Ile Lys Thr Thr Val Glu Asn Glu
    210                 215                 220

Leu Pro Pro Glu Asn Ile Glu Val Ser Val Gln Asn Gln Asn Tyr
225                 230                 235                 240

Val Leu Lys Trp Asp Tyr Thr Tyr Ala Asn Met Thr Phe Gln Val Gln
                245                 250                 255

Trp Leu His Ala Phe Leu Lys Arg Asn Pro Gly Asn His Leu Tyr Lys
            260                 265                 270

Trp Lys Gln Ile Pro Asp Cys Glu Asn Val Lys Thr Thr Gln Cys Val
        275                 280                 285

Phe Pro Gln Asn Val Phe Gln Lys Gly Ile Tyr Leu Leu Arg Val Gln
290                 295                 300

Ala Ser Asp Gly Asn Asn Thr Ser Phe Trp Ser Glu Ile Lys Phe
305                 310                 315                 320

Asp Thr Glu Ile Gln Ala Phe Leu Leu Pro Pro Val Phe Asn Ile Arg
            325                 330                 335

Ser Leu Ser Asp Ser Phe His Ile Tyr Ile Gly Ala Pro Lys Gln Ser
            340                 345                 350

Gly Asn Thr Pro Val Ile Gln Asp Tyr Pro Leu Ile Tyr Glu Ile Ile
            355                 360                 365

Phe Trp Glu Asn Thr Ser Asn Ala Glu Arg Lys Ile Ile Glu Lys Lys
        370                 375                 380

Thr Asp Val Thr Val Pro Asn Leu Lys Pro Leu Thr Val Tyr Cys Val
385                 390                 395                 400

Lys Ala Arg Ala His Thr Met Asp Glu Lys Leu Asn Lys Ser Ser Val
                405                 410                 415

Phe Ser Asp Ala Val Cys Glu Lys Thr Lys Pro Gly Asn Thr Ser Lys
            420                 425                 430

Ile Glu Gly Arg Met Asp Pro Lys Ser Cys Asp Lys Thr His Thr Cys
        435                 440                 445

Pro Pro Cys Pro Ala Pro Glu Leu Leu Gly Gly Pro Ser Val Phe Leu
450                 455                 460

Phe Pro Pro Lys Pro Lys Asp Thr Leu Met Ile Ser Arg Thr Pro Glu
465                 470                 475                 480

Val Thr Cys Val Val Val Asp Val Ser His Glu Asp Pro Glu Val Lys
                485                 490                 495

Phe Asn Trp Tyr Val Asp Gly Val Glu Val His Asn Ala Lys Thr Lys
                500                 505                 510

Pro Arg Glu Glu Gln Tyr Asn Ser Thr Tyr Arg Val Val Ser Val Leu
            515                 520                 525

Thr Val Leu His Gln Asp Trp Leu Asn Gly Lys Glu Tyr Lys Cys Lys
        530                 535                 540

Val Ser Asn Lys Ala Leu Pro Ala Pro Ile Glu Lys Thr Ile Ser Lys
545                 550                 555                 560
```

```
Ala Lys Gly Gln Pro Arg Glu Pro Gln Val Tyr Thr Leu Pro Pro Ser
                565                 570                 575

Arg Asp Glu Leu Thr Glu Asn Gln Val Ser Leu Thr Cys Leu Val Lys
            580                 585                 590

Gly Phe Tyr Pro Ser Asp Ile Ala Val Glu Trp Glu Ser Asn Gly Gln
        595                 600                 605

Pro Glu Asn Asn Tyr Lys Thr Thr Pro Pro Val Leu Asp Ser Asp Gly
    610                 615                 620

Ser Phe Phe Leu Tyr Ser Trp Leu Thr Val Asp Lys Ser Arg Trp Gln
625                 630                 635                 640

Gln Gly Asn Val Phe Ser Cys Ser Val Met His Glu Ala Leu His Asn
                645                 650                 655

His Tyr Thr Gln Lys Ser Leu Ser Leu Ser Pro Gly Lys
            660                 665
```

<210> SEQ ID NO 25
<211> LENGTH: 2010
<212> TYPE: DNA
<213> ORGANISM: Artificial Sequence
<220> FEATURE:
<223> OTHER INFORMATION: Synthetic: IFNAR1-Linker-FC RVT

<400> SEQUENCE: 25

```
gccaccatgt ggtggcgtct gtggtggctg ctgcttctgc tgttgctgct gtggcctatg      60
gtctgggcca agaacctgaa gtcccctcag aaagtggaag tggacatcat cgacgacaac     120
ttcatcctgc ggtggaacag atccgacgag tccgtgggca cgtgaccttc cagcttcgac     180
taccagaaaa ccggcatgga caactggatc aagctgtccg gctgccagaa catcacctct     240
accaagtgca acttctccag cctgaagctg aacgtgtacg aggaaatcaa gctgcggatc     300
cgggccgaga agagaaacac cagcagttgg tacgaggtgg acagcttcac cccttttcaga    360
aaggcccaga tcggccctcc tgaagtgcac ctggaagccg aggataaggc catcgtgatc     420
cacatcagcc ccggcaccaa ggactctgtg atgtgggctc tcgacggcct gtccttcacc     480
tacagcctgg tcatctggaa gaactcctcc ggcgtggaag agagaatcga gaacatctac     540
tccccggcaca agatctacaa gctgagcccc gagacaacct actgcctgaa agtgaaggcc     600
gctctgctga cctcctggaa gatcggcgtg tactctcccg tgcactgcat caagaccacc     660
gtggaaaacg agctgcctcc tcagagaaac atcgaggtgt ccgtgcagaa ccagaactac     720
gtgctgaagt gggactacac ctacgccaac atgaccttc aggtgcagtg gctgcacgct      780
tttctgaagc ggaaccctgg caaccacctg tacaagtgga agcagattcc cgactgcgag     840
aacgtgaaaa ccacacagtg cgtgttccct cagaacgtgt ccagaaggg catctacctg     900
ctgagagtgc aggcctccga cggcaacaac accagctttt ggagcgaaga gatcaagttc     960
gataccgaga tccaggcctt cctgctgcct ccagtgttca acatcagatc cctgtccgac    1020
tccttccaca tctacatcgg cgctcctaag cagtccggca caccccctgt gatccaggac    1080
taccctctga tctacgagat catcttctgg agaaacacct ccaacgccga gcggaagatc    1140
atcgagaaga aaaccgacgt gaccgtgcct aacctgaagc ctctgaccgt gtactgcgtg    1200
aaggctaggg cccacaccat ggacgaaaag ctgaacaagt cctccgtgtt ctccgacgcc    1260
gtgtgcgaaa agaccaagcc aggcaacacc tctaaaatcg agggccggat ggaccccaag    1320
agctgcgaca gacccacac ctgtcccccc tgccctgccc ctgaactgct gggcggaccc    1380
agcgtgttcc tgttcccccc aaagcccaag gacaccctga tgatcagccg gaccccccgaa    1440
```

-continued

```
gtgacctgcg tggtggtgga cgtgtcccac gaggaccctg aagtgaagtt caattggtac    1500
gtggacggcg tggaagtgca caacgccaag accaagccca gagaggaaca gtacaacagc    1560
acctaccggg tggtgtccgt gctgaccgtg ctgcaccagg actggctgaa cggcaaagag    1620
tacaagtgca aggtgtccaa caaggccctg cctgccccca tcgagaaaac catcagcaag    1680
gccaagggcc agccccgcga gccccgggtg tacacactgc cccccagccg ggacgagctg    1740
accaagaacc aggtgtccct gacctgcctg gtgaaaggct tctacccag cgatatcgcc     1800 gtggaatggg agagcaacgg ccagcccgag aacaactaca agaccacccc ccctgtgctg    1860
gtcagcgacg gctcattcac cctgtacagc aagctgaccg tggacaagag ccggtggcag    1920
cagggcaacg tgttcagctg cagcgtgatg cacgaggccc tgcacaacca ctacacccag    1980
aagtccctga gcctgagccc cggcaagtag                                     2010
```

<210> SEQ ID NO 26
<211> LENGTH: 669
<212> TYPE: PRT
<213> ORGANISM: Artificial Sequence
<220> FEATURE:
<223> OTHER INFORMATION: Synthetic: IFNAR1-Linker-FC RVT

<400> SEQUENCE: 26

```
Ala Thr Met Trp Trp Arg Leu Trp Trp Leu Leu Leu Leu Leu Leu Leu
1               5                   10                  15

Leu Trp Pro Met Val Trp Ala Lys Asn Leu Lys Ser Pro Gln Lys Val
            20                  25                  30

Glu Val Asp Ile Ile Asp Asp Asn Phe Ile Leu Arg Trp Asn Arg Ser
        35                  40                  45

Asp Glu Ser Val Gly Asn Val Thr Phe Ser Phe Asp Tyr Gln Lys Thr
    50                  55                  60

Gly Met Asp Asn Trp Ile Lys Leu Ser Gly Cys Gln Asn Ile Thr Ser
65                  70                  75                  80

Thr Lys Cys Asn Phe Ser Ser Leu Lys Leu Asn Val Tyr Glu Glu Ile
                85                  90                  95

Lys Leu Arg Ile Arg Ala Glu Lys Glu Asn Thr Ser Ser Trp Tyr Glu
            100                 105                 110

Val Asp Ser Phe Thr Pro Phe Arg Lys Ala Gln Ile Gly Pro Pro Glu
        115                 120                 125

Val His Leu Glu Ala Glu Asp Lys Ala Ile Val Ile His Ile Ser Pro
    130                 135                 140

Gly Thr Lys Asp Ser Val Met Trp Ala Leu Asp Gly Leu Ser Phe Thr
145                 150                 155                 160

Tyr Ser Leu Val Ile Trp Lys Asn Ser Ser Gly Val Glu Glu Arg Ile
                165                 170                 175

Glu Asn Ile Tyr Ser Arg His Lys Ile Tyr Lys Leu Ser Pro Glu Thr
            180                 185                 190

Thr Tyr Cys Leu Lys Val Lys Ala Ala Leu Leu Thr Ser Trp Lys Ile
        195                 200                 205

Gly Val Tyr Ser Pro Val His Cys Ile Lys Thr Thr Val Glu Asn Glu
    210                 215                 220

Leu Pro Pro Pro Glu Asn Ile Glu Val Ser Val Gln Asn Gln Asn Tyr
225                 230                 235                 240

Val Leu Lys Trp Asp Tyr Thr Tyr Ala Asn Met Thr Phe Gln Val Gln
                245                 250                 255

Trp Leu His Ala Phe Leu Lys Arg Asn Pro Gly Asn His Leu Tyr Lys
```

```
            260                 265                 270
Trp Lys Gln Ile Pro Asp Cys Glu Asn Val Lys Thr Thr Gln Cys Val
        275                 280                 285

Phe Pro Gln Asn Val Phe Gln Lys Gly Ile Tyr Leu Leu Arg Val Gln
        290                 295                 300

Ala Ser Asp Gly Asn Asn Thr Ser Phe Trp Ser Glu Ile Lys Phe
305                 310                 315                 320

Asp Thr Glu Ile Gln Ala Phe Leu Leu Pro Pro Val Phe Asn Ile Arg
                325                 330                 335

Ser Leu Ser Asp Ser Phe His Ile Tyr Ile Gly Ala Pro Lys Gln Ser
                340                 345                 350

Gly Asn Thr Pro Val Ile Gln Asp Tyr Pro Leu Ile Tyr Glu Ile Ile
            355                 360                 365

Phe Trp Glu Asn Thr Ser Asn Ala Glu Arg Lys Ile Ile Glu Lys Lys
        370                 375                 380

Thr Asp Val Thr Val Pro Asn Leu Lys Pro Leu Thr Val Tyr Cys Val
385                 390                 395                 400

Lys Ala Arg Ala His Thr Met Asp Glu Lys Leu Asn Lys Ser Ser Val
                405                 410                 415

Phe Ser Asp Ala Val Cys Glu Lys Thr Lys Pro Gly Asn Thr Ser Lys
                420                 425                 430

Ile Glu Gly Arg Met Asp Pro Lys Ser Cys Asp Lys Thr His Thr Cys
            435                 440                 445

Pro Pro Cys Pro Ala Pro Glu Leu Leu Gly Gly Pro Ser Val Phe Leu
        450                 455                 460

Phe Pro Pro Lys Pro Lys Asp Thr Leu Met Ile Ser Arg Thr Pro Glu
465                 470                 475                 480

Val Thr Cys Val Val Val Asp Val Ser His Glu Asp Pro Glu Val Lys
                485                 490                 495

Phe Asn Trp Tyr Val Asp Gly Val Glu Val His Asn Ala Lys Thr Lys
                500                 505                 510

Pro Arg Glu Glu Gln Tyr Asn Ser Thr Tyr Arg Val Val Ser Val Leu
            515                 520                 525

Thr Val Leu His Gln Asp Trp Leu Asn Gly Lys Glu Tyr Lys Cys Lys
        530                 535                 540

Val Ser Asn Lys Ala Leu Pro Ala Pro Ile Glu Lys Thr Ile Ser Lys
545                 550                 555                 560

Ala Lys Gly Gln Pro Arg Glu Pro Arg Val Tyr Thr Leu Pro Pro Ser
                565                 570                 575

Arg Asp Glu Leu Thr Lys Asn Gln Val Ser Leu Thr Cys Leu Val Lys
                580                 585                 590

Gly Phe Tyr Pro Ser Asp Ile Ala Val Glu Trp Glu Ser Asn Gly Gln
            595                 600                 605

Pro Glu Asn Asn Tyr Lys Thr Thr Pro Pro Val Leu Val Ser Asp Gly
        610                 615                 620

Ser Phe Thr Leu Tyr Ser Lys Leu Thr Val Asp Lys Ser Arg Trp Gln
625                 630                 635                 640

Gln Gly Asn Val Phe Ser Cys Ser Val Met His Glu Ala Leu His Asn
                645                 650                 655

His Tyr Thr Gln Lys Ser Leu Ser Leu Ser Pro Gly Lys
            660                 665

<210> SEQ ID NO 27
```

<211> LENGTH: 1434
<212> TYPE: DNA
<213> ORGANISM: Artificial Sequence
<220> FEATURE:
<223> OTHER INFORMATION: Synthetic: IFNAR2-Linker-FC WT

<400> SEQUENCE: 27

```
gccaccatgt ggtggcgtct gtggtggctg ctgcttctgc tgttgctgct gtggcctatg      60
gtctgggcca tctcctacga cagccctgac tacaccgacg agtcctgcac cttcaagatc     120
tccctgcgga acttccggtc catcctgtcc tgggagctga agaaccactc catcgtgccc     180
acacactaca ccctgctgta caccatcatg tccaagcctg aggacctgaa ggtggtcaag     240
aactgcgcca acaccaccag atctttctgc gacctgaccg atgagtggcg gtctacccac     300
gaggcttacg tgacagtgct ggaaggcttc tccggcaata ccacactgtt cagctgctcc     360
cacaacttct ggctggccat cgacatgtcc ttcgagcctc agagttcga gatcgtgggc     420
ttcaccaacc acatcaacgt gatggtcaag ttccccagca tcgtggaaga ggaactccag     480
ttcgacctga gcctggtcat cgaggaacag tccgagggca tcgtgaagaa gcacaagccc     540
gagatcaagg gcaacatgtc cggcaacttc acctacatca tcgacaagct gatccccaac     600
accaactact gcgtgtccgt gtacctggaa cactccgatg agcaggccgt gatcaagtcc     660
cctctgaagt gtaccctgct gcctcctggc caagagtctg agtctgccga gtctgctaaa     720
atcgagggcc ggatggaccc caagagctgc gacaagaccc acacctgtcc ccctgccct     780
gcccctgaac tgctgggcgg acccagcgtg ttcctgttcc ccccaaagcc caaggacacc     840
ctgatgatca gccggacccc cgaagtgacc tgcgtggtgg tggacgtgtc ccacgaggac     900
cctgaagtga agttcaattg gtacgtggac ggcgtggaag tgcacaacgc caagaccaag     960
cccagagagg aacagtacaa cagcacctac cgggtggtgt ccgtgctgac cgtgctgcac    1020
caggactggc tgaacggcaa agagtacaag tgcaaggtgt ccaacaaggc cctgcctgcc    1080
cccatcgaga aaaccatcag caaggccaag ggccagcccc gcgagcccca ggtgtacaca    1140
ctgccccca gccgggacga gctgaccaag aaccaggtgt ccctgacctg cctggtgaaa    1200
ggcttctacc ccagcgatat cgccgtggaa tgggagagca acggccagcc cgagaacaac    1260
tacaagacca cccccctgt gctggacagc gacggctcat tcttcctgta cagcaagctg    1320
accgtggaca gagccggtg gcagcagggc aacgtgttca gctgcagcgt gatgcacgag    1380
gccctgcaca accactacac ccagaagtcc ctgagcctga gccccggcaa gtga            1434
```

<210> SEQ ID NO 28
<211> LENGTH: 477
<212> TYPE: PRT
<213> ORGANISM: Artificial Sequence
<220> FEATURE:
<223> OTHER INFORMATION: Synthetic: IFNAR2-Linker-FC WT

<400> SEQUENCE: 28

```
Ala Thr Met Trp Trp Arg Leu Trp Trp Leu Leu Leu Leu Leu Leu Leu
 1               5                  10                  15

Leu Trp Pro Met Val Trp Ala Ile Ser Tyr Asp Ser Pro Asp Tyr Thr
            20                  25                  30

Asp Glu Ser Cys Thr Phe Lys Ile Ser Leu Arg Asn Phe Arg Ser Ile
        35                  40                  45

Leu Ser Trp Glu Leu Lys Asn His Ser Ile Val Pro Thr His Tyr Thr
    50                  55                  60

Leu Leu Tyr Thr Ile Met Ser Lys Pro Glu Asp Leu Lys Val Val Lys
```

```
                65                  70                  75                  80

Asn Cys Ala Asn Thr Thr Arg Ser Phe Cys Asp Leu Thr Asp Glu Trp
                        85                  90                  95

Arg Ser Thr His Glu Ala Tyr Val Thr Val Leu Glu Gly Phe Ser Gly
                       100                 105                 110

Asn Thr Thr Leu Phe Ser Cys Ser His Asn Phe Trp Leu Ala Ile Asp
                       115                 120                 125

Met Ser Phe Glu Pro Pro Glu Phe Glu Ile Val Gly Phe Thr Asn His
                       130                 135                 140

Ile Asn Val Met Val Lys Phe Pro Ser Ile Val Glu Glu Leu Gln
        145                 150                 155                 160

Phe Asp Leu Ser Leu Val Ile Glu Glu Gln Ser Gly Ile Val Lys
                       165                 170                 175

Lys His Lys Pro Glu Ile Lys Gly Asn Met Ser Gly Asn Phe Thr Tyr
                       180                 185                 190

Ile Ile Asp Lys Leu Ile Pro Asn Thr Asn Tyr Cys Val Ser Val Tyr
                       195                 200                 205

Leu Glu His Ser Asp Glu Gln Ala Val Ile Lys Ser Pro Leu Lys Cys
                       210                 215                 220

Thr Leu Leu Pro Pro Gly Gln Glu Ser Glu Ser Ala Glu Ser Ala Lys
        225                 230                 235                 240

Ile Glu Gly Arg Met Asp Pro Lys Ser Cys Asp Lys Thr His Thr Cys
                       245                 250                 255

Pro Pro Cys Pro Ala Pro Glu Leu Leu Gly Gly Pro Ser Val Phe Leu
                       260                 265                 270

Phe Pro Pro Lys Pro Lys Asp Thr Leu Met Ile Ser Arg Thr Pro Glu
                       275                 280                 285

Val Thr Cys Val Val Val Asp Val Ser His Glu Asp Pro Glu Val Lys
                       290                 295                 300

Phe Asn Trp Tyr Val Asp Gly Val Glu Val His Asn Ala Lys Thr Lys
        305                 310                 315                 320

Pro Arg Glu Glu Gln Tyr Asn Ser Thr Tyr Arg Val Val Ser Val Leu
                       325                 330                 335

Thr Val Leu His Gln Asp Trp Leu Asn Gly Lys Glu Tyr Lys Cys Lys
                       340                 345                 350

Val Ser Asn Lys Ala Leu Pro Ala Pro Ile Glu Lys Thr Ile Ser Lys
                       355                 360                 365

Ala Lys Gly Gln Pro Arg Glu Pro Gln Val Tyr Thr Leu Pro Pro Ser
                       370                 375                 380

Arg Asp Glu Leu Thr Lys Asn Gln Val Ser Leu Thr Cys Leu Val Lys
        385                 390                 395                 400

Gly Phe Tyr Pro Ser Asp Ile Ala Val Glu Trp Glu Ser Asn Gly Gln
                       405                 410                 415

Pro Glu Asn Asn Tyr Lys Thr Thr Pro Pro Val Leu Asp Ser Asp Gly
                       420                 425                 430

Ser Phe Phe Leu Tyr Ser Lys Leu Thr Val Asp Lys Ser Arg Trp Gln
                       435                 440                 445

Gln Gly Asn Val Phe Ser Cys Ser Val Met His Glu Ala Leu His Asn
                       450                 455                 460

His Tyr Thr Gln Lys Ser Leu Ser Leu Ser Pro Gly Lys
        465                 470                 475

<210> SEQ ID NO 29
```

<211> LENGTH: 1434
<212> TYPE: DNA
<213> ORGANISM: Artificial Sequence
<220> FEATURE:
<223> OTHER INFORMATION: Synthetic: IFNAR2-Linker-FC EW

<400> SEQUENCE: 29

```
gccaccatgt ggtggcgtct gtggtggctg ctgcttctgc tgttgctgct gtggcctatg      60
gtctgggcca tctcctacga cagccctgac tacaccgacg agtcctgcac cttcaagatc     120
tccctgcgga acttccggtc catcctgtcc tgggagctga gaaccactc catcgtgccc      180
acacactaca ccctgctgta caccatcatg tccaagcctg aggacctgaa ggtggtcaag     240
aactgcgcca acaccaccag atctttctgc gacctgaccg atgagtggcg gtctacccac     300
gaggcttacg tgacagtgct ggaaggcttc tccggcaata ccacactgtt cagctgctcc     360
cacaacttct ggctggccat cgacatgtcc ttcgagcctc agagttcga gatcgtgggc      420
ttcaccaacc acatcaacgt gatggtcaag ttccccagca tcgtggaaga ggaactccag     480
ttcgacctga gcctggtcat cgaggaacag tccgagggca tcgtgaagaa gcacaagccc     540
gagatcaagg gcaacatgtc cggcaacttc acctacatca tcgacaagct gatccccaac     600
accaactact gcgtgtccgt gtacctggaa cactccgatg agcaggccgt gatcaagtcc     660
cctctgaagt gtaccctgct gcctcctggc caagagtctg agtctgccga gtctgctaaa     720
atcgagggcc ggatggaccc caagagctgc gacaagaccc acacctgtcc ccctgccct      780
gcccctgaac tgctgggcgg acccagcgtg ttcctgttcc ccccaaagcc caaggacacc     840
ctgatgatca gccggacccc cgaagtgacc tgcgtggtgg tggacgtgtc ccacgaggac     900
cctgaagtga agttcaattg gtacgtggac ggcgtggaag tgcacaacgc caagaccaag     960
cccagagagg aacagtacaa cagcacctac cgggtggtgt ccgtgctgac cgtgctgcac    1020
caggactggc tgaacggcaa agagtacaag tgcaaggtgt ccaacaaggc cctgcctgcc    1080
cccatcgaga aaaccatcag caaggccaag ggccagcccc gcgagcccca ggtgtacaca    1140
ctgccccca gccgggacga gctgaccgag aaccaggtgt ccctgacctg cctggtgaaa    1200
ggcttctacc ccagcgatat cgccgtggaa tgggagagca acggccagcc cgagaacaac    1260
tacaagacca cccccctgt gctggacagc gacggctcat tcttcctgta cagctggctg    1320
accgtggaca gagccggtg gcagcaggc aacgtgttca gctgcagcgt gatgcacgag     1380
gccctgcaca accactacac ccagaagtcc ctgagcctga gccccggcaa gtag           1434
```

<210> SEQ ID NO 30
<211> LENGTH: 477
<212> TYPE: PRT
<213> ORGANISM: Artificial Sequence
<220> FEATURE:
<223> OTHER INFORMATION: Synthetic: IFNAR2-Linker-FC EW

<400> SEQUENCE: 30

```
Ala Thr Met Trp Trp Arg Leu Trp Trp Leu Leu Leu Leu Leu Leu Leu
1               5                   10                  15

Leu Trp Pro Met Val Trp Ala Ile Ser Tyr Asp Ser Pro Asp Tyr Thr
                20                  25                  30

Asp Glu Ser Cys Thr Phe Lys Ile Ser Leu Arg Asn Phe Arg Ser Ile
            35                  40                  45

Leu Ser Trp Glu Leu Lys Asn His Ser Ile Val Pro Thr His Tyr Thr
        50                  55                  60

Leu Leu Tyr Thr Ile Met Ser Lys Pro Glu Asp Leu Lys Val Val Lys
```

```
              65                  70                  75                  80
         Asn Cys Ala Asn Thr Thr Arg Ser Phe Cys Asp Leu Thr Asp Glu Trp
                          85                  90                  95

Arg Ser Thr His Glu Ala Tyr Val Thr Val Leu Glu Gly Phe Ser Gly
                         100                 105                 110

Asn Thr Thr Leu Phe Ser Cys Ser His Asn Phe Trp Leu Ala Ile Asp
                         115                 120                 125

Met Ser Phe Glu Pro Glu Phe Glu Ile Val Gly Phe Thr Asn His
             130                 135                 140

Ile Asn Val Met Val Lys Phe Pro Ser Ile Val Glu Glu Leu Gln
         145                 150                 155                 160

Phe Asp Leu Ser Leu Val Ile Glu Glu Gln Ser Glu Gly Ile Val Lys
                         165                 170                 175

Lys His Lys Pro Glu Ile Lys Gly Asn Met Ser Gly Asn Phe Thr Tyr
                         180                 185                 190

Ile Ile Asp Lys Leu Ile Pro Asn Thr Asn Tyr Cys Val Ser Val Tyr
                     195                 200                 205

Leu Glu His Ser Asp Glu Gln Ala Val Ile Lys Ser Pro Leu Lys Cys
             210                 215                 220

Thr Leu Leu Pro Pro Gly Gln Glu Ser Glu Ser Ala Glu Ser Ala Lys
         225                 230                 235                 240

Ile Glu Gly Arg Met Asp Pro Lys Ser Cys Asp Lys Thr His Thr Cys
                         245                 250                 255

Pro Pro Cys Pro Ala Pro Glu Leu Leu Gly Gly Pro Ser Val Phe Leu
                         260                 265                 270

Phe Pro Pro Lys Pro Lys Asp Thr Leu Met Ile Ser Arg Thr Pro Glu
                     275                 280                 285

Val Thr Cys Val Val Val Asp Val Ser His Glu Asp Pro Glu Val Lys
             290                 295                 300

Phe Asn Trp Tyr Val Asp Gly Val Glu Val His Asn Ala Lys Thr Lys
         305                 310                 315                 320

Pro Arg Glu Glu Gln Tyr Asn Ser Thr Tyr Arg Val Val Ser Val Leu
                         325                 330                 335

Thr Val Leu His Gln Asp Trp Leu Asn Gly Lys Glu Tyr Lys Cys Lys
                         340                 345                 350

Val Ser Asn Lys Ala Leu Pro Ala Pro Ile Glu Lys Thr Ile Ser Lys
                     355                 360                 365

Ala Lys Gly Gln Pro Arg Glu Pro Gln Val Tyr Thr Leu Pro Pro Ser
             370                 375                 380

Arg Asp Glu Leu Thr Glu Asn Gln Val Ser Leu Thr Cys Leu Val Lys
         385                 390                 395                 400

Gly Phe Tyr Pro Ser Asp Ile Ala Val Glu Trp Glu Ser Asn Gly Gln
                         405                 410                 415

Pro Glu Asn Asn Tyr Lys Thr Thr Pro Pro Val Leu Asp Ser Asp Gly
                         420                 425                 430

Ser Phe Phe Leu Tyr Ser Trp Leu Thr Val Asp Lys Ser Arg Trp Gln
                     435                 440                 445

Gln Gly Asn Val Phe Ser Cys Ser Val Met His Glu Ala Leu His Asn
             450                 455                 460

His Tyr Thr Gln Lys Ser Leu Ser Leu Ser Pro Gly Lys
         465                 470                 475

<210> SEQ ID NO 31
```

<211> LENGTH: 1434
<212> TYPE: DNA
<213> ORGANISM: Artificial Sequence
<220> FEATURE:
<223> OTHER INFORMATION: Synthetic: IFNAR2-Linker-FC RVT

<400> SEQUENCE: 31

```
gccaccatgt ggtggcgtct gtggtggctg ctgcttctgc tgttgctgct gtggcctatg      60
gtctgggcca tctcctacga cagccctgac tacaccgacg agtcctgcac cttcaagatc     120
tccctgcgga acttccggtc catcctgtcc tgggagctga agaaccactc catcgtgccc     180
acacactaca ccctgctgta caccatcatg tccaagcctg aggacctgaa ggtggtcaag     240
aactgcgcca acaccaccag atctttctgc gacctgaccg atgagtggcg gtctacccac     300
gaggcttacg tgacagtgct ggaaggcttc tccggcaata ccacactgtt cagctgctcc     360
cacaacttct ggctggccat cgacatgtcc ttcgagcctc agagttcga gatcgtgggc      420
ttcaccaacc acatcaacgt gatggtcaag ttccccagca tcgtggaaga ggaactccag     480
ttcgacctga gcctggtcat cgaggaacag tccgaggga tcgtgaagaa gcacaagccc      540
gagatcaagg gcaacatgtc cggcaacttc acctacatca tcgacaagct gatccccaac     600
accaactact gcgtgtccgt gtacctggaa cactccgatg agcaggccgt gatcaagtcc     660
cctctgaagt gtaccctgct gcctcctggc caagagtctg agtctgccga gtctgctaaa     720
atcgagggcc ggatggaccc caagagctgc gacaagaccc acacctgtcc ccctgccct      780
gcccctgaac tgctgggcgg acccagcgtg ttcctgttcc ccccaaagcc caaggacacc     840
ctgatgatca gccggacccc cgaagtgacc tgcgtggtgg tggacgtgtc ccacgaggac     900
cctgaagtga agttcaattg gtacgtggac ggcgtggaag tgcacaacgc caagaccaag     960
cccagagagg aacagtacaa cagcacctac cgggtggtgt ccgtgctgac cgtgctgcac    1020
caggactggc tgaacggcaa agagtacaag tgcaaggtgt ccaacaaggc cctgcctgcc    1080
cccatcgaga aaaccatcag caaggccaag ggccagcccc gcgagccccg ggtgtacaca    1140
ctgccccca gccgggacga gctgaccaag aaccaggtgt ccctgacctg cctggtgaaa     1200
ggcttctacc ccagcgatat cgccgtggaa tgggagagca acggccagcc cgagaacaac    1260
tacaagacca ccccccctgt gctggtcagc gacggctcat tcaccctgta cagcaagctg    1320
accgtggaca gagccggtg gcagcagggc aacgtgttca gctgcagcgt gatgcacgag     1380
gccctgcaca accactacac ccagaagtcc ctgagcctga gccccggcaa gtag          1434
```

<210> SEQ ID NO 32
<211> LENGTH: 477
<212> TYPE: PRT
<213> ORGANISM: Artificial Sequence
<220> FEATURE:
<223> OTHER INFORMATION: Synthetic: IFNAR2-Linker-FC RVT

<400> SEQUENCE: 32

```
Ala Thr Met Trp Trp Arg Leu Trp Trp Leu Leu Leu Leu Leu Leu Leu
1               5                   10                  15

Leu Trp Pro Met Val Trp Ala Ile Ser Tyr Asp Ser Pro Asp Tyr Thr
            20                  25                  30

Asp Glu Ser Cys Thr Phe Lys Ile Ser Leu Arg Asn Phe Arg Ser Ile
        35                  40                  45

Leu Ser Trp Glu Leu Lys Asn His Ser Ile Val Pro Thr His Tyr Thr
    50                  55                  60

Leu Leu Tyr Thr Ile Met Ser Lys Pro Glu Asp Leu Lys Val Val Lys
```

```
            65                  70                  75                  80
        Asn Cys Ala Asn Thr Thr Arg Ser Phe Cys Asp Leu Thr Asp Glu Trp
                        85                  90                  95
        Arg Ser Thr His Glu Ala Tyr Val Thr Val Leu Glu Gly Phe Ser Gly
                       100                 105                 110
        Asn Thr Thr Leu Phe Ser Cys Ser His Asn Phe Trp Leu Ala Ile Asp
                       115                 120                 125
        Met Ser Phe Glu Pro Glu Phe Glu Ile Val Gly Phe Thr Asn His
                   130                 135                 140
        Ile Asn Val Met Val Lys Phe Pro Ser Ile Val Glu Glu Leu Gln
        145                 150                 155                 160
        Phe Asp Leu Ser Leu Val Ile Glu Glu Gln Ser Glu Gly Ile Val Lys
                       165                 170                 175
        Lys His Lys Pro Glu Ile Lys Gly Asn Met Ser Gly Asn Phe Thr Tyr
                       180                 185                 190
        Ile Ile Asp Lys Leu Ile Pro Asn Thr Asn Tyr Cys Val Ser Val Tyr
                       195                 200                 205
        Leu Glu His Ser Asp Glu Gln Ala Val Ile Lys Ser Pro Leu Lys Cys
                   210                 215                 220
        Thr Leu Leu Pro Pro Gly Gln Glu Ser Glu Ser Ala Glu Ser Ala Lys
        225                 230                 235                 240
        Ile Glu Gly Arg Met Asp Pro Lys Ser Cys Asp Lys Thr His Thr Cys
                       245                 250                 255
        Pro Pro Cys Pro Ala Pro Glu Leu Leu Gly Gly Pro Ser Val Phe Leu
                       260                 265                 270
        Phe Pro Pro Lys Pro Lys Asp Thr Leu Met Ile Ser Arg Thr Pro Glu
                   275                 280                 285
        Val Thr Cys Val Val Val Asp Val Ser His Glu Asp Pro Glu Val Lys
                   290                 295                 300
        Phe Asn Trp Tyr Val Asp Gly Val Glu Val His Asn Ala Lys Thr Lys
        305                 310                 315                 320
        Pro Arg Glu Glu Gln Tyr Asn Ser Thr Tyr Arg Val Val Ser Val Leu
                       325                 330                 335
        Thr Val Leu His Gln Asp Trp Leu Asn Gly Lys Glu Tyr Lys Cys Lys
                   340                 345                 350
        Val Ser Asn Lys Ala Leu Pro Ala Pro Ile Glu Lys Thr Ile Ser Lys
                   355                 360                 365
        Ala Lys Gly Gln Pro Arg Glu Pro Arg Val Tyr Thr Leu Pro Pro Ser
                   370                 375                 380
        Arg Asp Glu Leu Thr Lys Asn Gln Val Ser Leu Thr Cys Leu Val Lys
        385                 390                 395                 400
        Gly Phe Tyr Pro Ser Asp Ile Ala Val Glu Trp Glu Ser Asn Gly Gln
                       405                 410                 415
        Pro Glu Asn Asn Tyr Lys Thr Thr Pro Pro Val Leu Val Ser Asp Gly
                   420                 425                 430
        Ser Phe Thr Leu Tyr Ser Lys Leu Thr Val Asp Lys Ser Arg Trp Gln
                   435                 440                 445
        Gln Gly Asn Val Phe Ser Cys Ser Val Met His Glu Ala Leu His Asn
                   450                 455                 460
        His Tyr Thr Gln Lys Ser Leu Ser Leu Ser Pro Gly Lys
        465                 470                 475

<210> SEQ ID NO 33
```

<210> SEQ ID NO 33
<211> LENGTH: 45
<212> TYPE: DNA
<213> ORGANISM: Artificial Sequence
<220> FEATURE:
<223> OTHER INFORMATION: Synthetic: Linker_4GS*3

<400> SEQUENCE: 33

```
ggcggcggag gatctggcgg aggtggaagc ggaggcggtg gatct            45
```

<210> SEQ ID NO 34
<211> LENGTH: 15
<212> TYPE: PRT
<213> ORGANISM: Artificial Sequence
<220> FEATURE:
<223> OTHER INFORMATION: Synthetic: Linker_4GS*3

<400> SEQUENCE: 34

```
Gly Gly Gly Gly Ser Gly Gly Gly Gly Ser Gly Gly Gly Gly Ser
1               5                   10                  15
```

<210> SEQ ID NO 35
<211> LENGTH: 810
<212> TYPE: DNA
<213> ORGANISM: Artificial Sequence
<220> FEATURE:
<223> OTHER INFORMATION: Synthetic: Linker_4GS*3-FC WT

<400> SEQUENCE: 35

```
gccaccatgt ggtggcgtct gtggtggctg ctgcttctgc tgttgctgct gtggcctatg     60
gtctgggccg gcggcggagg atctggcgga ggtggaagcg gaggcggtgg atctcccaag    120
agctgcgaca gacccacac ctgtccccc  tgccctgccc ctgaactgct gggcggaccc    180
agcgtgttcc tgttcccccc aaagcccaag acaccctga tgatcagccg gaccccgaa     240
gtgacctgcg tggtggtgga cgtgtcccac gaggaccctg aagtgaagtt caattggtac    300
gtggacggcg tggaagtgca caacgccaag accaagccca gagaggaaca gtacaacagc    360
acctaccggg tggtgtccgt gctgaccgtg ctgcaccagg actggctgaa cggcaaagag    420
tacaagtgca aggtgtccaa caaggccctg cctgccccca tcgagaaaac catcagcaag    480
gccaagggcc agccccgcga gccccaggtg tacacactgc cccccagccg ggacgagctg    540
accaagaacc aggtgtccct gacctgcctg gtgaaaggct tctacccag cgatatcgcc    600
gtggaatggg agagcaacgg ccagcccgag aacaactaca agaccacccc ccctgtgctg    660
gacagcgacg gctcattctt cctgtacagc aagctgaccg tggacaagag ccggtggcag    720
cagggcaacg tgttcagctg cagcgtgatg cacgaggccc tgcacaacca ctacacccag    780
aagtccctga gcctgagccc cggcaagtga                                     810
```

<210> SEQ ID NO 36
<211> LENGTH: 269
<212> TYPE: PRT
<213> ORGANISM: Artificial Sequence
<220> FEATURE:
<223> OTHER INFORMATION: Synthetic: Linker_4GS*3-FC WT

<400> SEQUENCE: 36

```
Ala Thr Met Trp Trp Arg Leu Trp Trp Leu Leu Leu Leu Leu Leu
1               5                   10                  15

Leu Trp Pro Met Val Trp Ala Gly Gly Gly Gly Ser Gly Gly Gly Gly
            20                  25                  30

Ser Gly Gly Gly Gly Ser Pro Lys Ser Cys Asp Lys Thr His Thr Cys
        35                  40                  45
```

Pro Pro Cys Pro Ala Pro Glu Leu Leu Gly Gly Pro Ser Val Phe Leu
    50                  55                  60

Phe Pro Pro Lys Pro Lys Asp Thr Leu Met Ile Ser Arg Thr Pro Glu
65                  70                  75                  80

Val Thr Cys Val Val Val Asp Val Ser His Glu Asp Pro Glu Val Lys
                85                  90                  95

Phe Asn Trp Tyr Val Asp Gly Val Glu Val His Asn Ala Lys Thr Lys
                100                 105                 110

Pro Arg Glu Glu Gln Tyr Asn Ser Thr Tyr Arg Val Val Ser Val Leu
            115                 120                 125

Thr Val Leu His Gln Asp Trp Leu Asn Gly Lys Glu Tyr Lys Cys Lys
            130                 135                 140

Val Ser Asn Lys Ala Leu Pro Ala Pro Ile Glu Lys Thr Ile Ser Lys
145                 150                 155                 160

Ala Lys Gly Gln Pro Arg Glu Pro Gln Val Tyr Thr Leu Pro Pro Ser
                165                 170                 175

Arg Asp Glu Leu Thr Lys Asn Gln Val Ser Leu Thr Cys Leu Val Lys
                180                 185                 190

Gly Phe Tyr Pro Ser Asp Ile Ala Val Glu Trp Glu Ser Asn Gly Gln
            195                 200                 205

Pro Glu Asn Asn Tyr Lys Thr Thr Pro Pro Val Leu Asp Ser Asp Gly
            210                 215                 220

Ser Phe Phe Leu Tyr Ser Lys Leu Thr Val Asp Lys Ser Arg Trp Gln
225                 230                 235                 240

Gln Gly Asn Val Phe Ser Cys Ser Val Met His Glu Ala Leu His Asn
                245                 250                 255

His Tyr Thr Gln Lys Ser Leu Ser Leu Ser Pro Gly Lys
            260                 265

<210> SEQ ID NO 37
<211> LENGTH: 810
<212> TYPE: DNA
<213> ORGANISM: Artificial Sequence
<220> FEATURE:
<223> OTHER INFORMATION: Synthetic: Linker_4GS*3-FC EW

<400> SEQUENCE: 37
gccaccatgt ggtggcgtct gtggtggctg ctgcttctgc tgttgctgct gtggcctatg      60
gtctgggccg gcggcggagg atctggcgga ggtggaagcg gaggcggtgg atctcccaag     120
agctgcgaca gacccacac ctgtccccc tgccctgccc ctgaactgct gggcggaccc      180
agcgtgttcc tgttcccccc aaagcccaag dacaccctga tgatcagccg daccccgaa     240 gtgacctgcg tggtggtgga cgtgtcccac gaggaccctg aagtgaagtt caattggtac     300
gtggacggcg tggaagtgca caacgccaag accaagccca gagaggaaca gtacaacagc     360
acctaccggg tggtgtccgt gctgaccgtg ctgcaccagg actggctgaa cggcaaagag     420
tacaagtgca aggtgtccaa caaggccctg cctgccccca tcgagaaaac catcagcaag     480
gccaagggcc agccccgcga gccccaggtg tacacactgc cccccagccg ggacgagctg     540
accgagaacc aggtgtccct gacctgcctg gtgaaaggct tctacccag cgatatcgcc     600 gtggaatggg agagcaacgg ccagcccgag aacaactaca agaccacccc cctgtgctg     660 gacagcgacg gctcattctt cctgtacagc aagctgaccg tggacaagag ccggtggcag     720
cagggcaacg tgttcagctg cagcgtgatg cacgaggccc tgcacaacca ctacacccag     780
aagtccctga gcctgagccc cggcaagtag 810

<210> SEQ ID NO 38
<211> LENGTH: 269
<212> TYPE: PRT
<213> ORGANISM: Artificial Sequence
<220> FEATURE:
<223> OTHER INFORMATION: Synthetic: Linker_4GS*3-FC EW

<400> SEQUENCE: 38

Ala Thr Met Trp Trp Arg Leu Trp Trp Leu Leu Leu Leu Leu Leu Leu
1               5                   10                  15

Leu Trp Pro Met Val Trp Ala Gly Gly Gly Ser Gly Gly Gly Gly
            20                  25                  30

Ser Gly Gly Gly Ser Pro Lys Ser Cys Asp Lys Thr His Thr Cys
        35                  40                  45

Pro Pro Cys Pro Ala Pro Glu Leu Leu Gly Gly Pro Ser Val Phe Leu
50                  55                  60

Phe Pro Pro Lys Pro Lys Asp Thr Leu Met Ile Ser Arg Thr Pro Glu
65                  70                  75                  80

Val Thr Cys Val Val Val Asp Val Ser His Glu Asp Pro Glu Val Lys
                85                  90                  95

Phe Asn Trp Tyr Val Asp Gly Val Glu Val His Asn Ala Lys Thr Lys
            100                 105                 110

Pro Arg Glu Glu Gln Tyr Asn Ser Thr Tyr Arg Val Val Ser Val Leu
        115                 120                 125

Thr Val Leu His Gln Asp Trp Leu Asn Gly Lys Glu Tyr Lys Cys Lys
130                 135                 140

Val Ser Asn Lys Ala Leu Pro Ala Pro Ile Glu Lys Thr Ile Ser Lys
145                 150                 155                 160

Ala Lys Gly Gln Pro Arg Glu Pro Gln Val Tyr Thr Leu Pro Pro Ser
                165                 170                 175

Arg Asp Glu Leu Thr Glu Asn Gln Val Ser Leu Thr Cys Leu Val Lys
            180                 185                 190

Gly Phe Tyr Pro Ser Asp Ile Ala Val Glu Trp Glu Ser Asn Gly Gln
        195                 200                 205

Pro Glu Asn Asn Tyr Lys Thr Thr Pro Pro Val Leu Asp Ser Asp Gly
210                 215                 220

Ser Phe Phe Leu Tyr Ser Trp Leu Thr Val Asp Lys Ser Arg Trp Gln
225                 230                 235                 240

Gln Gly Asn Val Phe Ser Cys Ser Val Met His Glu Ala Leu His Asn
                245                 250                 255

His Tyr Thr Gln Lys Ser Leu Ser Leu Ser Pro Gly Lys
            260                 265

<210> SEQ ID NO 39
<211> LENGTH: 810
<212> TYPE: DNA
<213> ORGANISM: Artificial Sequence
<220> FEATURE:
<223> OTHER INFORMATION: Synthetic: Linker_4GS*3-FC RVT

<400> SEQUENCE: 39
gccaccatgt ggtggcgtct gtggtggctg ctgcttctgc tgttgctgct gtggcctatg      60
gtctgggccg gcggcggagg atctggcgga ggtggaagcg gaggcggtgg atctcccaag     120
agctgcgaca agacccacac ctgtcccccc tgccctgccc ctgaactgct gggcggaccc     180

```
agcgtgttcc tgttccccec aaagcccaag acaccctga tgatcagccg gaccccgaa      240 gtgacctgcg tggtggtgga cgtgtcccac gaggaccctg aagtgaagtt caattggtac    300
gtggacggcg tggaagtgca caacgccaag accaagccca gagaggaaca gtacaacagc    360
acctaccggg tggtgtccgt gctgaccgtg ctgcaccagg actggctgaa cggcaaagag    420
tacaagtgca aggtgtccaa caaggccctg cctgccccca tcgagaaaac catcagcaag    480
gccaagggcc agccccgcga gccccgggtg tacacactgc cccccagccg ggacgagctg    540
accaagaacc aggtgtccct gacctgcctg gtgaaaggct tctacccag cgatatcgcc     600 gtggaatggg agagcaacgg ccagcccgag aacaactaca agaccacccc ccctgtgctg    660
gtcagcgacg gctcattcac cctgtacagc aagctgaccg tggacaagag ccggtggcag    720
cagggcaacg tgttcagctg cagcgtgatg cacgaggccc tgcacaacca ctacacccag    780
aagtccctga gcctgagccc cggcaagtag                                      810
```

<210> SEQ ID NO 40
<211> LENGTH: 269
<212> TYPE: PRT
<213> ORGANISM: Artificial Sequence
<220> FEATURE:
<223> OTHER INFORMATION: Synthetic: Linker_4GS*3-FC RVT

<400> SEQUENCE: 40

```
Ala Thr Met Trp Trp Arg Leu Trp Trp Leu Leu Leu Leu Leu Leu Leu
1               5                   10                  15

Leu Trp Pro Met Val Trp Ala Gly Gly Gly Ser Gly Gly Gly Gly
            20                  25                  30

Ser Gly Gly Gly Gly Ser Pro Lys Ser Cys Asp Lys Thr His Thr Cys
        35                  40                  45

Pro Pro Cys Pro Ala Pro Glu Leu Leu Gly Gly Pro Ser Val Phe Leu
    50                  55                  60

Phe Pro Pro Lys Pro Lys Asp Thr Leu Met Ile Ser Arg Thr Pro Glu
65                  70                  75                  80

Val Thr Cys Val Val Val Asp Val Ser His Glu Asp Pro Glu Val Lys
                85                  90                  95

Phe Asn Trp Tyr Val Asp Gly Val Glu Val His Asn Ala Lys Thr Lys
            100                 105                 110

Pro Arg Glu Glu Gln Tyr Asn Ser Thr Tyr Arg Val Val Ser Val Leu
        115                 120                 125

Thr Val Leu His Gln Asp Trp Leu Asn Gly Lys Glu Tyr Lys Cys Lys
    130                 135                 140

Val Ser Asn Lys Ala Leu Pro Ala Pro Ile Glu Lys Thr Ile Ser Lys
145                 150                 155                 160

Ala Lys Gly Gln Pro Arg Glu Pro Arg Val Tyr Thr Leu Pro Pro Ser
                165                 170                 175

Arg Asp Glu Leu Thr Lys Asn Gln Val Ser Leu Thr Cys Leu Val Lys
            180                 185                 190

Gly Phe Tyr Pro Ser Asp Ile Ala Val Glu Trp Glu Ser Asn Gly Gln
        195                 200                 205

Pro Glu Asn Asn Tyr Lys Thr Thr Pro Pro Val Leu Val Ser Asp Gly
    210                 215                 220

Ser Phe Thr Leu Tyr Ser Lys Leu Thr Val Asp Lys Ser Arg Trp Gln
225                 230                 235                 240

Gln Gly Asn Val Phe Ser Cys Ser Val Met His Glu Ala Leu His Asn
                245                 250                 255
```

His Tyr Thr Gln Lys Ser Leu Ser Leu Ser Pro Gly Lys
        260                 265

<210> SEQ ID NO 41
<211> LENGTH: 2037
<212> TYPE: DNA
<213> ORGANISM: Artificial Sequence
<220> FEATURE:
<223> OTHER INFORMATION: Synthetic: IFNAR1-Linker_4GS*3-FC WT

<400> SEQUENCE: 41

| | | | | |
|---|---|---|---|---|
| gccaccatgt | ggtggcgtct | gtggtggctg | ctgcttctgc | tgttgctgct | gtggcctatg | 60 |
| gtctgggcca | agaacctgaa | gtcccctcag | aaagtggaag | tggacatcat | cgacgacaac | 120 |
| ttcatcctgc | ggtggaacag | atccgacgag | tccgtgggca | acgtgacctt | cagcttcgac | 180 |
| taccagaaaa | ccggcatgga | caactggatc | aagctgtccg | gctgccagaa | catcacctct | 240 |
| accaagtgca | acttctccag | cctgaagctg | aacgtgtacg | aggaaatcaa | gctgcggatc | 300 |
| cgggccgaga | aagagaacac | cagcagttgg | tacgaggtgg | acagcttcac | ccctttcaga | 360 |
| aaggcccaga | tcggccctcc | tgaagtgcac | ctggaagccg | aggataaggc | catcgtgatc | 420 |
| cacatcagcc | ccgcaccaa | ggactctgtg | atgtgggctc | tcgacggcct | gtccttcacc | 480 |
| tacagcctgg | tcatctggaa | gaactcctcc | ggcgtggaag | agagaatcga | aacatctac | 540 |
| tcccggcaca | agatctacaa | gctgagcccc | gagacaacct | actgcctgaa | agtgaaggcc | 600 |
| gctctgctga | cctcctggaa | gatcggcgtg | tactctcccg | tgcactgcat | caagaccacc | 660 |
| gtggaaaacg | agctgcctcc | tcagagaaac | atcgaggtgt | ccgtgcagaa | ccagaactac | 720 |
| gtgctgaagt | gggactacac | ctacgccaac | atgaccttc | aggtgcagtg | gctgcacgct | 780 |
| tttctgaagc | ggaaccctgg | caaccacctg | tacaagtgga | agcagattcc | cgactgcgag | 840 |
| aacgtgaaaa | ccacacagtg | cgtgttccct | cagaacgtgt | ccagaaggg | catctacctg | 900 |
| ctgagagtgc | aggcctccga | cggcaacaac | accagctttt | ggagcgaaga | gatcaagttc | 960 |
| gataccgaga | tccaggcctt | cctgctgcct | ccagtgttca | acatcagatc | cctgtccgac | 1020 |
| tccttccaca | tctacatcgg | cgctcctaag | cagtccggca | caccctgt | gatccaggac | 1080 |
| taccctctga | tctacgagat | catcttctgg | gagaacacct | ccaacgccga | gcggaagatc | 1140 |
| atcgagaaga | aaaccgacgt | gaccgtgcct | aacctgaagc | tctgaccgt | gtactgcgtg | 1200 |
| aaggctaggg | cccacaccat | ggacgaaaag | ctgaacaagt | cctccgtgtt | ctccgacgcc | 1260 |
| gtgtgcgaaa | agaccaagcc | aggcaacacc | tctaaaggcg | gcggaggatc | tggcggaggt | 1320 |
| ggaagcggag | gcggtggatc | tcccaagagc | tgcgacaaga | cccacacctg | tccccctgc | 1380 |
| cctgcccctg | aactgctggg | cggacccagc | gtgttcctgt | tccccccaaa | gcccaaggac | 1440 |
| accctgatga | tcagccggac | ccccgaagtg | acctgcgtgg | tggtggacgt | gtcccacgag | 1500 |
| gaccctgaag | tgaagttcaa | ttggtacgtg | gacggcgtgg | aagtgcacaa | cgccaagacc | 1560 |
| aagcccagag | aggaacagta | caacagcacc | taccgggtgg | tgtccgtgct | gaccgtgctg | 1620 |
| caccaggact | ggctgaacgg | caaagagtac | aagtgcaagg | tgtccaacaa | ggccctgcct | 1680 |
| gccccatcg | agaaaaccat | cagcaaggcc | aagggccagc | ccgcgagcc | ccaggtgtac | 1740 |
| acactgcccc | ccagccggga | cgagctgacc | aagaaccagg | tgtccctgac | ctgcctggtg | 1800 |
| aaaggcttct | accccagcga | tatcgccgtg | gaatgggaga | gcaacggcca | gcccgagaac | 1860 |
| aactacaaga | ccacccccc | tgtgctggac | agcgacggct | cattcttcct | gtacagcaag | 1920 |
| ctgaccgtgg | acaagagccg | gtggcagcag | ggcaacgtgt | tcagctgcag | cgtgatgcac | 1980 | gaggccctgc acaaccacta cacccagaag tccctgagcc tgagcccccgg caagtga    2037

<210> SEQ ID NO 42
<211> LENGTH: 678
<212> TYPE: PRT
<213> ORGANISM: Artificial Sequence
<220> FEATURE:
<223> OTHER INFORMATION: Synthetic: IFNAR1-Linker_4GS*3-FC WT

<400> SEQUENCE: 42

```
Ala Thr Met Trp Trp Arg Leu Trp Trp Leu Leu Leu Leu Leu Leu
1               5                   10                  15

Leu Trp Pro Met Val Trp Ala Lys Asn Leu Lys Ser Pro Gln Lys Val
            20                  25                  30

Glu Val Asp Ile Ile Asp Asp Asn Phe Ile Leu Arg Trp Asn Arg Ser
        35                  40                  45

Asp Glu Ser Val Gly Asn Val Thr Phe Ser Phe Asp Tyr Gln Lys Thr
    50                  55                  60

Gly Met Asp Asn Trp Ile Lys Leu Ser Gly Cys Gln Asn Ile Thr Ser
65                  70                  75                  80

Thr Lys Cys Asn Phe Ser Ser Leu Lys Leu Asn Val Tyr Glu Glu Ile
                85                  90                  95

Lys Leu Arg Ile Arg Ala Glu Lys Glu Asn Thr Ser Ser Trp Tyr Glu
            100                 105                 110

Val Asp Ser Phe Thr Pro Phe Arg Lys Ala Gln Ile Gly Pro Pro Glu
        115                 120                 125

Val His Leu Glu Ala Glu Asp Lys Ala Ile Val Ile His Ile Ser Pro
    130                 135                 140

Gly Thr Lys Asp Ser Val Met Trp Ala Leu Asp Gly Leu Ser Phe Thr
145                 150                 155                 160

Tyr Ser Leu Val Ile Trp Lys Asn Ser Ser Gly Val Glu Glu Arg Ile
                165                 170                 175

Glu Asn Ile Tyr Ser Arg His Lys Ile Tyr Lys Leu Ser Pro Glu Thr
            180                 185                 190

Thr Tyr Cys Leu Lys Val Lys Ala Ala Leu Leu Thr Ser Trp Lys Ile
        195                 200                 205

Gly Val Tyr Ser Pro Val His Cys Ile Lys Thr Thr Val Glu Asn Glu
    210                 215                 220

Leu Pro Pro Pro Glu Asn Ile Glu Val Ser Val Gln Asn Gln Asn Tyr
225                 230                 235                 240

Val Leu Lys Trp Asp Tyr Thr Tyr Ala Asn Met Thr Phe Gln Val Gln
                245                 250                 255

Trp Leu His Ala Phe Leu Lys Arg Asn Pro Gly Asn His Leu Tyr Lys
            260                 265                 270

Trp Lys Gln Ile Pro Asp Cys Glu Asn Val Lys Thr Thr Gln Cys Val
        275                 280                 285

Phe Pro Gln Asn Val Phe Gln Lys Gly Ile Tyr Leu Leu Arg Val Gln
    290                 295                 300

Ala Ser Asp Gly Asn Asn Thr Ser Phe Trp Ser Glu Glu Ile Lys Phe
305                 310                 315                 320

Asp Thr Glu Ile Gln Ala Phe Leu Leu Pro Pro Val Phe Asn Ile Arg
                325                 330                 335

Ser Leu Ser Asp Ser Phe His Ile Tyr Ile Gly Ala Pro Lys Gln Ser
            340                 345                 350
```

Gly Asn Thr Pro Val Ile Gln Asp Tyr Pro Leu Ile Tyr Glu Ile Ile
            355                 360                 365

Phe Trp Glu Asn Thr Ser Asn Ala Glu Arg Lys Ile Ile Glu Lys Lys
    370                 375                 380

Thr Asp Val Thr Val Pro Asn Leu Lys Pro Leu Thr Val Tyr Cys Val
385                 390                 395                 400

Lys Ala Arg Ala His Thr Met Asp Glu Lys Leu Asn Lys Ser Ser Val
                405                 410                 415

Phe Ser Asp Ala Val Cys Glu Lys Thr Lys Pro Gly Asn Thr Ser Lys
            420                 425                 430

Gly Gly Gly Gly Ser Gly Gly Gly Ser Gly Gly Gly Ser Pro
            435                 440                 445

Lys Ser Cys Asp Lys Thr His Thr Cys Pro Pro Cys Pro Ala Pro Glu
    450                 455                 460

Leu Leu Gly Gly Pro Ser Val Phe Leu Phe Pro Pro Lys Pro Lys Asp
465                 470                 475                 480

Thr Leu Met Ile Ser Arg Thr Pro Glu Val Thr Cys Val Val Val Asp
                485                 490                 495

Val Ser His Glu Asp Pro Glu Val Lys Phe Asn Trp Tyr Val Asp Gly
            500                 505                 510

Val Glu Val His Asn Ala Lys Thr Lys Pro Arg Glu Glu Gln Tyr Asn
    515                 520                 525

Ser Thr Tyr Arg Val Val Ser Val Leu Thr Val Leu His Gln Asp Trp
530                 535                 540

Leu Asn Gly Lys Glu Tyr Lys Cys Lys Val Ser Asn Lys Ala Leu Pro
545                 550                 555                 560

Ala Pro Ile Glu Lys Thr Ile Ser Lys Ala Lys Gly Gln Pro Arg Glu
                565                 570                 575

Pro Gln Val Tyr Thr Leu Pro Pro Ser Arg Asp Glu Leu Thr Lys Asn
            580                 585                 590

Gln Val Ser Leu Thr Cys Leu Val Lys Gly Phe Tyr Pro Ser Asp Ile
    595                 600                 605

Ala Val Glu Trp Glu Ser Asn Gly Gln Pro Glu Asn Asn Tyr Lys Thr
610                 615                 620

Thr Pro Pro Val Leu Asp Ser Asp Gly Ser Phe Phe Leu Tyr Ser Lys
625                 630                 635                 640

Leu Thr Val Asp Lys Ser Arg Trp Gln Gln Gly Asn Val Phe Ser Cys
                645                 650                 655

Ser Val Met His Glu Ala Leu His Asn His Tyr Thr Gln Lys Ser Leu
            660                 665                 670

Ser Leu Ser Pro Gly Lys
        675

<210> SEQ ID NO 43
<211> LENGTH: 2037
<212> TYPE: DNA
<213> ORGANISM: Artificial Sequence
<220> FEATURE:
<223> OTHER INFORMATION: Synthetic: IFNAR1-Linker_4GS*3-FC EW

<400> SEQUENCE: 43
gccaccatgt ggtggcgtct gtggtggctg ctgcttctgc tgttgctgct gtggcctatg      60
gtctgggcca agaacctgaa gtcccctcag aaagtggaag tggacatcat cgacgacaac     120
ttcatcctgc ggtggaacag atccgacgag tccgtgggca cgtgaccctt cagcttcgac     180

| | |
|---|---|
| taccagaaaa ccggcatgga caactggatc aagctgtccg gctgccagaa catcacctct | 240 |
| accaagtgca acttctccag cctgaagctg aacgtgtacg aggaaatcaa gctgcggatc | 300 |
| cgggccgaga agagaacaca cagcagttgg tacgaggtgg acagcttcac cccttttcaga | 360 |
| aaggcccaga tcggcctcc tgaagtgcac ctggaagccg aggataaggc catcgtgatc | 420 |
| cacatcagcc ccggcaccaa ggactctgtg atgtgggctc tcgacggcct gtccttcacc | 480 |
| tacagcctgg tcatctggaa gaactcctcc ggcgtggaag agagaatcga gaacatctac | 540 |
| tcccggcaca agatctacaa gctgagcccc gagacaacct actgcctgaa agtgaaggcc | 600 |
| gctctgctga cctcctggaa gatcggcgtg tactctcccg tgcactgcat caagaccacc | 660 |
| gtggaaaacg agctgcctcc tccagagaac atcgaggtgt ccgtgcagaa ccagaactac | 720 |
| gtgctgaagt gggactacac ctacgccaac atgacctttc aggtgcagtg gctgcacgct | 780 |
| tttctgaagc ggaaccctgg caaccacctg tacaagtgga agcagattcc cgactgcgag | 840 |
| aacgtgaaaa ccacacagtg cgtgttccct cagaacgtgt ccagaaggg catctacctg | 900 |
| ctgagagtgc aggcctccga cggcaacaac accagctttt ggagcgaaga gatcaagttc | 960 |
| gataccgaga tccaggcctt cctgctgcct ccagtgttca acatcagatc cctgtccgac | 1020 |
| tccttccaca tctacatcgg cgctcctaag cagtccggca cacccctgt gatccaggac | 1080 |
| taccctctga tctacgagat catcttctgg gagaacacct ccaacgccga gcggaagatc | 1140 |
| atcgagaaga aaaccgacgt gaccgtgcct aacctgaagc tctgaccgt gtactgcgtg | 1200 |
| aaggctaggg cccacaccat ggacgaaaag ctgaacaagt cctccgtgtt ctccgacgcc | 1260 |
| gtgtgcgaaa agaccaagcc aggcaacacc tctaaaggcg gcggaggatc tggcggaggt | 1320 |
| ggaagcggag gcggtggatc tcccaagagc tgcgacaaga cccacacctg tcccccctgc | 1380 |
| cctgccctg aactgctggg cggacccagc gtgttcctgt tccccccaaa gcccaaggac | 1440 |
| accctgatga tcagccggac ccccgaagtg acctgcgtgg tggtggacgt gtcccacgag | 1500 |
| gaccctgaag tgaagttcaa ttggtacgtg gacggcgtgg aagtgcacaa cgccaagacc | 1560 |
| aagcccagag aggaacagta caacagcacc taccgggtgg tgtccgtgct gaccgtgctg | 1620 |
| caccaggact ggctgaacgg caaagagtac aagtgcaagg tgtccaacaa ggcccctgcct | 1680 |
| gcccccatcg agaaaaccat cagcaaggcc aagggccagc ccgcgagcc ccaggtgtac | 1740 |
| acactgcccc ccagccggga cgagctgacc gagaaccagg tgtccctgac ctgcctggtg | 1800 |
| aaaggcttct accccagcga tatcgccgtg gaatgggaga gcaacggcca gcccgagaac | 1860 |
| aactacaaga ccacccccc tgtgctggac agcgacggct cattcttcct gtacagctgg | 1920 |
| ctgaccgtgg acaagagccg gtggcagcag ggcaacgtgt tcagctgcag cgtgatgcac | 1980 |
| gaggccctgc acaaccacta cacccagaag tccctgagcc tgagccccgg caagtag | 2037 |

<210> SEQ ID NO 44
<211> LENGTH: 678
<212> TYPE: PRT
<213> ORGANISM: Artificial Sequence
<220> FEATURE:
<223> OTHER INFORMATION: Synthetic: IFNAR1-Linker_4GS*3-FC EW

<400> SEQUENCE: 44

Ala Thr Met Trp Trp Arg Leu Trp Trp Leu Leu Leu Leu Leu Leu
1               5                   10                  15

Leu Trp Pro Met Val Trp Ala Lys Asn Leu Lys Ser Pro Gln Lys Val
            20                  25                  30

Glu Val Asp Ile Ile Asp Asp Asn Phe Ile Leu Arg Trp Asn Arg Ser

```
                35                  40                  45
Asp Glu Ser Val Gly Asn Val Thr Phe Ser Phe Asp Tyr Gln Lys Thr
 50                  55                  60
Gly Met Asp Asn Trp Ile Lys Leu Ser Gly Cys Gln Asn Ile Thr Ser
 65                  70                  75                  80
Thr Lys Cys Asn Phe Ser Ser Leu Lys Leu Asn Val Tyr Glu Glu Ile
                 85                  90                  95
Lys Leu Arg Ile Arg Ala Glu Lys Glu Asn Thr Ser Ser Trp Tyr Glu
                100                 105                 110
Val Asp Ser Phe Thr Pro Phe Arg Lys Ala Gln Ile Gly Pro Pro Glu
                115                 120                 125
Val His Leu Glu Ala Glu Asp Lys Ala Ile Val Ile His Ile Ser Pro
                130                 135                 140
Gly Thr Lys Asp Ser Val Met Trp Ala Leu Asp Gly Leu Ser Phe Thr
145                 150                 155                 160
Tyr Ser Leu Val Ile Trp Lys Asn Ser Ser Gly Val Glu Glu Arg Ile
                165                 170                 175
Glu Asn Ile Tyr Ser Arg His Lys Ile Tyr Lys Leu Ser Pro Glu Thr
                180                 185                 190
Thr Tyr Cys Leu Lys Val Lys Ala Ala Leu Leu Thr Ser Trp Lys Ile
                195                 200                 205
Gly Val Tyr Ser Pro Val His Cys Ile Lys Thr Thr Val Glu Asn Glu
210                 215                 220
Leu Pro Pro Pro Glu Asn Ile Glu Val Ser Val Gln Asn Gln Asn Tyr
225                 230                 235                 240
Val Leu Lys Trp Asp Tyr Thr Tyr Ala Asn Met Thr Phe Gln Val Gln
                245                 250                 255
Trp Leu His Ala Phe Leu Lys Arg Asn Pro Gly Asn His Leu Tyr Lys
                260                 265                 270
Trp Lys Gln Ile Pro Asp Cys Glu Asn Val Lys Thr Thr Gln Cys Val
                275                 280                 285
Phe Pro Gln Asn Val Phe Gln Lys Gly Ile Tyr Leu Leu Arg Val Gln
                290                 295                 300
Ala Ser Asp Gly Asn Asn Thr Ser Phe Trp Ser Glu Glu Ile Lys Phe
305                 310                 315                 320
Asp Thr Glu Ile Gln Ala Phe Leu Leu Pro Pro Val Phe Asn Ile Arg
                325                 330                 335
Ser Leu Ser Asp Ser Phe His Ile Tyr Ile Gly Ala Pro Lys Gln Ser
                340                 345                 350
Gly Asn Thr Pro Val Ile Gln Asp Tyr Pro Leu Ile Tyr Glu Ile Ile
                355                 360                 365
Phe Trp Glu Asn Thr Ser Asn Ala Glu Arg Lys Ile Ile Glu Lys Lys
                370                 375                 380
Thr Asp Val Thr Val Pro Asn Leu Lys Pro Leu Thr Val Tyr Cys Val
385                 390                 395                 400
Lys Ala Arg Ala His Thr Met Asp Glu Lys Leu Asn Lys Ser Ser Val
                405                 410                 415
Phe Ser Asp Ala Val Cys Glu Lys Thr Lys Pro Gly Asn Thr Ser Lys
                420                 425                 430
Gly Gly Gly Gly Ser Gly Gly Gly Ser Gly Gly Gly Ser Pro
                435                 440                 445
Lys Ser Cys Asp Lys Thr His Thr Cys Pro Pro Cys Pro Ala Pro Glu
450                 455                 460
```

```
Leu Gly Gly Pro Ser Val Phe Leu Phe Pro Pro Lys Pro Lys Asp
465                 470                 475                 480

Thr Leu Met Ile Ser Arg Thr Pro Glu Val Thr Cys Val Val Val Asp
            485                 490                 495

Val Ser His Glu Asp Pro Glu Val Lys Phe Asn Trp Tyr Val Asp Gly
        500                 505                 510

Val Glu Val His Asn Ala Lys Thr Lys Pro Arg Glu Glu Gln Tyr Asn
        515                 520                 525

Ser Thr Tyr Arg Val Val Ser Val Leu Thr Val Leu His Gln Asp Trp
    530                 535                 540

Leu Asn Gly Lys Glu Tyr Lys Cys Lys Val Ser Asn Lys Ala Leu Pro
545                 550                 555                 560

Ala Pro Ile Glu Lys Thr Ile Ser Lys Ala Lys Gly Gln Pro Arg Glu
                565                 570                 575

Pro Gln Val Tyr Thr Leu Pro Pro Ser Arg Asp Glu Leu Thr Glu Asn
            580                 585                 590

Gln Val Ser Leu Thr Cys Leu Val Lys Gly Phe Tyr Pro Ser Asp Ile
        595                 600                 605

Ala Val Glu Trp Glu Ser Asn Gly Gln Pro Glu Asn Asn Tyr Lys Thr
        610                 615                 620

Thr Pro Pro Val Leu Asp Ser Asp Gly Ser Phe Phe Leu Tyr Ser Trp
625                 630                 635                 640

Leu Thr Val Asp Lys Ser Arg Trp Gln Gln Gly Asn Val Phe Ser Cys
                645                 650                 655

Ser Val Met His Glu Ala Leu His Asn His Tyr Thr Gln Lys Ser Leu
            660                 665                 670

Ser Leu Ser Pro Gly Lys
            675

<210> SEQ ID NO 45
<211> LENGTH: 2037
<212> TYPE: DNA
<213> ORGANISM: Artificial Sequence
<220> FEATURE:
<223> OTHER INFORMATION: Synthetic: IFNAR1-Linker_4GS*3-FC RVT

<400> SEQUENCE: 45
gccaccatgt ggtggcgtct gtggtggctg ctgcttctgc tgttgctgct gtggcctatg      60
gtctgggcca agaacctgaa gtcccctcag aaagtggaag tggacatcat cgacgacaac     120
ttcatcctgc ggtggaacag atccgacgag tccgtgggca acgtgacctt cagcttcgac     180
taccagaaaa ccggcatgga caactggatc aagctgtccg gctgccagaa catcacctct     240
accaagtgca cttctccag cctgaagctg aacgtgacg aggaaatcaa gctgcggatc       300
cgggccgaga agagaacac cagcagttgg tacgaggtgg acagcttcac ccctttcaga      360
aaggcccaga tcggccctcc tgaagtgcac ctggaagccg aggataaggc catcgtgatc     420
cacatcagcc ccggcaccaa ggactctgtg atgtgggctc tcgacggcct gtccttcacc    480
tacagcctgg tcatctggaa gaactcctcc ggcgtggaag agagaatcga gaacatctac     540
tcccggcaca gatctacaa gctgagcccc gagacaacct actgcctgaa agtgaaggcc     600
gctctgctga cctcctggaa gatcggcgtg tactctcccg tgcactgcat caagaccacc     660
gtggaaaacg agctgcctcc tcagagaaac atcgaggtgt ccgtgcagaa ccagaactac    720
gtgctgaagt gggactacac ctacgccaac atgacctttc aggtgcagtg gctgcacgct    780
```

```
tttctgaagc ggaaccctgg caaccacctg tacaagtgga agcagattcc cgactgcgag    840
aacgtgaaaa ccacacagtg cgtgttccct cagaacgtgt tccagaaggg catctacctg    900
ctgagagtgc aggcctccga cggcaacaac accagctttt ggagcgaaga gatcaagttc    960
gataccgaga tccaggcctt cctgctgcct ccagtgttca acatcagatc cctgtccgac   1020
tccttccaca tctacatcgg cgctcctaag cagtccggca caccctgt gatccaggac    1080 taccctctga tctacgagat catcttctgg gagaacacct ccaacgccga gcggaagatc   1140
atcgagaaga aaaccgacgt gaccgtgcct aacctgaagc tctgaccgt gtactgcgtg    1200 aaggctaggg cccacaccat ggacgaaaag ctgaacaagt cctccgtgtt ctccgacgcc   1260
gtgtgcgaaa agaccaagcc aggcaacacc tctaaaggcg gcggaggatc tggcggaggt   1320
ggaagcggag gcgtggatc tcccaagagc tgcgacaaga cccacacctg tcccccctgc    1380
cctgcccctg aactgctggg cggacccagc gtgttcctgt tccccccaaa gcccaaggac    1440
accctgatga tcagccggac ccccgaagtg acctgcgtgg tggtggacgt gtcccacgag   1500
gaccctgaag tgaagttcaa ttggtacgtg gacggcgtgg aagtgcacaa cgccaagacc   1560
aagcccagag aggaacagta caacagcacc taccgggtgg tgtccgtgct gaccgtgctg   1620
caccaggact ggctgaacgg caaagagtac aagtgcaagg tgtccaacaa ggccctgcct   1680
gcccccatcg agaaaaccat cagcaaggcc aagggccagc ccgcgagcc ccgggtgtac    1740 acactgcccc cagccggga cgagctgacc aagaaccagg tgtccctgac ctgcctggtg    1800
aaaggcttct accccagcga tatcgccgtg gaatgggaga gcaacggcca gcccgagaac   1860
aactacaaga ccaccccccc tgtgctggtc agcgacggct cattcaccct gtacagcaag   1920
ctgaccgtgg acaagagccg gtggcagcag ggcaacgtgt tcagctgcag cgtgatgcac   1980
gaggccctgc acaaccacta cacccagaag tccctgagcc tgagccccgg caagtag     2037
```

<210> SEQ ID NO 46
<211> LENGTH: 678
<212> TYPE: PRT
<213> ORGANISM: Artificial Sequence
<220> FEATURE:
<223> OTHER INFORMATION: Synthetic: IFNAR1-Linker_4GS*3-FC RVT

<400> SEQUENCE: 46

```
Ala Thr Met Trp Trp Arg Leu Trp Trp Leu Leu Leu Leu Leu Leu Leu
1               5                  10                  15

Leu Trp Pro Met Val Trp Ala Lys Asn Leu Lys Ser Pro Gln Lys Val
            20                  25                  30

Glu Val Asp Ile Ile Asp Asp Asn Phe Ile Leu Arg Trp Asn Arg Ser
        35                  40                  45

Asp Glu Ser Val Gly Asn Val Thr Phe Ser Phe Asp Tyr Gln Lys Thr
    50                  55                  60

Gly Met Asp Asn Trp Ile Lys Leu Ser Gly Cys Gln Asn Ile Thr Ser
65                  70                  75                  80

Thr Lys Cys Asn Phe Ser Ser Leu Lys Leu Asn Val Tyr Glu Glu Ile
                85                  90                  95

Lys Leu Arg Ile Arg Ala Glu Lys Glu Asn Thr Ser Ser Trp Tyr Glu
            100                 105                 110

Val Asp Ser Phe Thr Pro Phe Arg Lys Ala Gln Ile Gly Pro Pro Glu
        115                 120                 125

Val His Leu Glu Ala Glu Asp Lys Ala Ile Val Ile His Ile Ser Pro
    130                 135                 140
```

Gly Thr Lys Asp Ser Val Met Trp Ala Leu Asp Gly Leu Ser Phe Thr
145                 150                 155                 160

Tyr Ser Leu Val Ile Trp Lys Asn Ser Ser Gly Val Glu Glu Arg Ile
            165                 170                 175

Glu Asn Ile Tyr Ser Arg His Lys Ile Tyr Lys Leu Ser Pro Glu Thr
                180                 185                 190

Thr Tyr Cys Leu Lys Val Lys Ala Ala Leu Leu Thr Ser Trp Lys Ile
        195                 200                 205

Gly Val Tyr Ser Pro Val His Cys Ile Lys Thr Thr Val Glu Asn Glu
        210                 215                 220

Leu Pro Pro Pro Glu Asn Ile Glu Val Ser Val Gln Asn Gln Asn Tyr
225                 230                 235                 240

Val Leu Lys Trp Asp Tyr Thr Tyr Ala Asn Met Thr Phe Gln Val Gln
            245                 250                 255

Trp Leu His Ala Phe Leu Lys Arg Asn Pro Gly Asn His Leu Tyr Lys
            260                 265                 270

Trp Lys Gln Ile Pro Asp Cys Glu Asn Val Lys Thr Thr Gln Cys Val
        275                 280                 285

Phe Pro Gln Asn Val Phe Gln Lys Gly Ile Tyr Leu Leu Arg Val Gln
290                 295                 300

Ala Ser Asp Gly Asn Asn Thr Ser Phe Trp Ser Glu Glu Ile Lys Phe
305                 310                 315                 320

Asp Thr Glu Ile Gln Ala Phe Leu Leu Pro Pro Val Phe Asn Ile Arg
                325                 330                 335

Ser Leu Ser Asp Ser Phe His Ile Tyr Ile Gly Ala Pro Lys Gln Ser
            340                 345                 350

Gly Asn Thr Pro Val Ile Gln Asp Tyr Pro Leu Ile Tyr Glu Ile Ile
            355                 360                 365

Phe Trp Glu Asn Thr Ser Asn Ala Glu Arg Lys Ile Ile Glu Lys Lys
370                 375                 380

Thr Asp Val Thr Val Pro Asn Leu Lys Pro Leu Thr Val Tyr Cys Val
385                 390                 395                 400

Lys Ala Arg Ala His Thr Met Asp Glu Lys Leu Asn Lys Ser Ser Val
                405                 410                 415

Phe Ser Asp Ala Val Cys Glu Lys Thr Lys Pro Gly Asn Thr Ser Lys
            420                 425                 430

Gly Gly Gly Gly Ser Gly Gly Gly Ser Gly Gly Gly Gly Ser Pro
            435                 440                 445

Lys Ser Cys Asp Lys Thr His Thr Cys Pro Pro Cys Pro Ala Pro Glu
450                 455                 460

Leu Leu Gly Gly Pro Ser Val Phe Leu Phe Pro Pro Lys Pro Lys Asp
465                 470                 475                 480

Thr Leu Met Ile Ser Arg Thr Pro Glu Val Thr Cys Val Val Val Asp
                485                 490                 495

Val Ser His Glu Asp Pro Glu Val Lys Phe Asn Trp Tyr Val Asp Gly
            500                 505                 510

Val Glu Val His Asn Ala Lys Thr Lys Pro Arg Glu Glu Gln Tyr Asn
            515                 520                 525

Ser Thr Tyr Arg Val Val Ser Val Leu Thr Val Leu His Gln Asp Trp
            530                 535                 540

Leu Asn Gly Lys Glu Tyr Lys Cys Lys Val Ser Asn Lys Ala Leu Pro
545                 550                 555                 560

Ala Pro Ile Glu Lys Thr Ile Ser Lys Ala Lys Gly Gln Pro Arg Glu

```
                    565                 570                 575
Pro Arg Val Tyr Thr Leu Pro Pro Ser Arg Asp Glu Leu Thr Lys Asn
                580                 585                 590

Gln Val Ser Leu Thr Cys Leu Val Lys Gly Phe Tyr Pro Ser Asp Ile
            595                 600                 605

Ala Val Glu Trp Glu Ser Asn Gly Gln Pro Glu Asn Asn Tyr Lys Thr
        610                 615                 620

Thr Pro Pro Val Leu Val Ser Asp Gly Ser Phe Thr Leu Tyr Ser Lys
625                 630                 635                 640

Leu Thr Val Asp Lys Ser Arg Trp Gln Gln Gly Asn Val Phe Ser Cys
                645                 650                 655

Ser Val Met His Glu Ala Leu His Asn His Tyr Thr Gln Lys Ser Leu
            660                 665                 670

Ser Leu Ser Pro Gly Lys
            675

<210> SEQ ID NO 47
<211> LENGTH: 1461
<212> TYPE: DNA
<213> ORGANISM: Artificial Sequence
<220> FEATURE:
<223> OTHER INFORMATION: Synthetic: IFNAR2-Linker_4GS*3-FC WT

<400> SEQUENCE: 47
gccaccatgt ggtggcgtct gtggtggctg ctgcttctgc tgttgctgct gtggcctatg      60
gtctgggcca tctcctacga cagccctgac tacaccgacg agtcctgcac cttcaagatc     120
tccctgcgga acttccggtc catcctgtcc tgggagctga agaaccactc catcgtgccc     180
acacactaca ccctgctgta caccatcatg tccaagcctg aggacctgaa ggtggtcaag     240
aactgcgcca acaccaccag atctttctgc gacctgaccg atgagtggcg gtctacccac     300
gaggcttacg tgacagtgct ggaaggcttc tccggcaata ccacactgtt cagctgctcc     360
cacaacttct ggctggccat cgacatgtcc ttcgagcctc agagttcga dcgtgggc       420 ttcaccaacc acatcaacgt gatggtcaag ttccccagca tcgtggaaga ggaactccag     480
ttcgacctga gcctggtcat cgaggaacag tccgagggca tcgtgaagaa gcacaagccc     540
gagatcaagg gcaacatgtc cggcaacttc acctacatca tcgacaagct gatccccaac     600
accaactact gcgtgtccgt gtacctggaa cactccgatg agcaggccgt gatcaagtcc     660
cctctgaagt gtaccctgct gcctcctggc aagagtctg agtctgccga gtctgctaaa      720
ggcggcggag gatctggcgg aggtggaagc ggaggcggtg gatctcccaa gagctgcgac     780
aagacccaca cctgtccccc ctgccctgcc cctgaactgc tgggcggacc cagcgtgttc     840
ctgttccccc caaagcccaa ggacaccctg atgatcagcc ggacccccga agtgacctgc     900
gtggtggtgg acgtgtccca cgaggaccct gaagtgaagt tcaattggta cgtggacggc     960
gtggaagtgc acaacgccaa gaccaagccc agagaggaac agtacaacag cacctaccgg    1020
gtggtgtccg tgctgaccgt gctgcaccag gactggctga acggcaaaga gtacaagtgc    1080
aaggtgtcca acaaggccct gcctgccccc atcgagaaaa ccatcagcaa ggccaagggc    1140
cagccccgcg agccccaggt gtacacactg cccccagcc gggacgagct gaccaagaac     1200
caggtgtccc tgacctgcct ggtgaaaggc ttctaccccca gcgatatcgc cgtggaatgg    1260
gagagcaacg gccagcccga gaacaactac aagaccaccc cccctgtgct ggacagcgac    1320
ggctcattct tcctgtacag caagctgacc gtggacaaga gccggtggca gcagggcaac    1380
```

```
gtgttcagct gcagcgtgat gcacgaggcc ctgcacaacc actacaccca gaagtccctg    1440
agcctgagcc ccggcaagtg a                                              1461
```

<210> SEQ ID NO 48
<211> LENGTH: 486
<212> TYPE: PRT
<213> ORGANISM: Artificial Sequence
<220> FEATURE:
<223> OTHER INFORMATION: Synthetic: IFNAR2-Linker_4GS*3-FC WT

<400> SEQUENCE: 48

```
Ala Thr Met Trp Trp Arg Leu Trp Trp Leu Leu Leu Leu Leu Leu Leu
1               5                   10                  15

Leu Trp Pro Met Val Trp Ala Ile Ser Tyr Asp Ser Pro Asp Tyr Thr
            20                  25                  30

Asp Glu Ser Cys Thr Phe Lys Ile Ser Leu Arg Asn Phe Arg Ser Ile
        35                  40                  45

Leu Ser Trp Glu Leu Lys Asn His Ser Ile Val Pro Thr His Tyr Thr
    50                  55                  60

Leu Leu Tyr Thr Ile Met Ser Lys Pro Glu Asp Leu Lys Val Val Lys
65                  70                  75                  80

Asn Cys Ala Asn Thr Thr Arg Ser Phe Cys Asp Leu Thr Asp Glu Trp
                85                  90                  95

Arg Ser Thr His Glu Ala Tyr Val Thr Val Leu Glu Gly Phe Ser Gly
            100                 105                 110

Asn Thr Thr Leu Phe Ser Cys Ser His Asn Phe Trp Leu Ala Ile Asp
        115                 120                 125

Met Ser Phe Glu Pro Pro Glu Phe Glu Ile Val Gly Phe Thr Asn His
    130                 135                 140

Ile Asn Val Met Val Lys Phe Pro Ser Ile Val Glu Glu Glu Leu Gln
145                 150                 155                 160

Phe Asp Leu Ser Leu Val Ile Glu Glu Gln Ser Glu Gly Ile Val Lys
                165                 170                 175

Lys His Lys Pro Glu Ile Lys Gly Asn Met Ser Gly Asn Phe Thr Tyr
            180                 185                 190

Ile Ile Asp Lys Leu Ile Pro Asn Thr Asn Tyr Cys Val Ser Val Tyr
        195                 200                 205

Leu Glu His Ser Asp Glu Gln Ala Val Ile Lys Ser Pro Leu Lys Cys
    210                 215                 220

Thr Leu Leu Pro Pro Gly Gln Glu Ser Glu Ser Ala Glu Ser Ala Lys
225                 230                 235                 240

Gly Gly Gly Gly Ser Gly Gly Gly Ser Gly Gly Gly Ser Pro
                245                 250                 255

Lys Ser Cys Asp Lys Thr His Thr Cys Pro Pro Cys Pro Ala Pro Glu
            260                 265                 270

Leu Leu Gly Gly Pro Ser Val Phe Leu Phe Pro Pro Lys Pro Lys Asp
        275                 280                 285

Thr Leu Met Ile Ser Arg Thr Pro Glu Val Thr Cys Val Val Val Asp
    290                 295                 300

Val Ser His Glu Asp Pro Glu Val Lys Phe Asn Trp Tyr Val Asp Gly
305                 310                 315                 320

Val Glu Val His Asn Ala Lys Thr Lys Pro Arg Glu Glu Gln Tyr Asn
                325                 330                 335

Ser Thr Tyr Arg Val Val Ser Val Leu Thr Val Leu His Gln Asp Trp
            340                 345                 350
```

Leu Asn Gly Lys Glu Tyr Lys Cys Lys Val Ser Asn Lys Ala Leu Pro
            355                 360                 365

Ala Pro Ile Glu Lys Thr Ile Ser Lys Ala Lys Gly Gln Pro Arg Glu
    370                 375                 380

Pro Gln Val Tyr Thr Leu Pro Pro Ser Arg Asp Glu Leu Thr Lys Asn
385                 390                 395                 400

Gln Val Ser Leu Thr Cys Leu Val Lys Gly Phe Tyr Pro Ser Asp Ile
                405                 410                 415

Ala Val Glu Trp Glu Ser Asn Gly Gln Pro Glu Asn Asn Tyr Lys Thr
            420                 425                 430

Thr Pro Pro Val Leu Asp Ser Asp Gly Ser Phe Phe Leu Tyr Ser Lys
            435                 440                 445

Leu Thr Val Asp Lys Ser Arg Trp Gln Gln Gly Asn Val Phe Ser Cys
    450                 455                 460

Ser Val Met His Glu Ala Leu His Asn His Tyr Thr Gln Lys Ser Leu
465                 470                 475                 480

Ser Leu Ser Pro Gly Lys
            485

<210> SEQ ID NO 49
<211> LENGTH: 1461
<212> TYPE: DNA
<213> ORGANISM: Artificial Sequence
<220> FEATURE:
<223> OTHER INFORMATION: Synthetic: IFNAR2-Linker_4GS*3-FC EW

<400> SEQUENCE: 49
gccaccatgt ggtggcgtct gtggtggctg ctgcttctgc tgttgctgct gtggcctatg      60
gtctgggcca tctcctacga cagccctgac tacaccgacg agtcctgcac cttcaagatc     120
tccctgcgga acttccggtc catcctgtcc tgggagctga agaaccactc catcgtgccc     180
acacactaca ccctgctgta caccatcatg tccaagcctg aggacctgaa ggtggtcaag     240
aactgcgcca acaccaccag atctttctgc gacctgaccg atgagtggcg gtctacccac     300
gaggcttacg tgacagtgct ggaaggcttc tccggcaata ccacactgtt cagctgctcc     360
cacaacttct ggctggccat cgacatgtcc ttcgagcctc agagttcga gatcgtgggc     420 ttcaccaacc acatcaacgt gatggtcaag ttccccagca tcgtggaaga ggaactccag     480
ttcgacctga gcctggtcat cgaggaacag tccgagggca tcgtgaagaa gcacaagccc     540
gagatcaagg gcaacatgtc cggcaacttc acctacatca tcgacaagct gatccccaac     600
accaactact gcgtgtccgt gtacctggaa cactccgatg agcaggccgt gatcaagtcc     660
cctctgaagt gtaccctgct gcctcctggc aagagtctg agtctgccga gtctgctaaa     720
ggcggcggag atctggcgg aggtggaagc ggaggcggtg atctcccaa gagctgcgac     780 aagacccaca cctgtccccc ctgccctgcc cctgaactgc tgggcggacc cagcgtgttc     840
ctgttccccc caaagcccaa ggacaccctg atgatcagcc ggacccccga agtgacctgc     900
gtggtggtgg acgtgtccca cgaggaccct gaagtgaagt tcaattggta cgtggacggc     960
gtggaagtgc acaacgccaa gaccaagccc agagaggaac agtacaacag cacctaccgg    1020
gtggtgtccg tgctgaccgt gctgcaccag gactggctga acggcaaaga gtacaagtgc    1080
aaggtgtcca acaaggccct gcctgccccc atcgagaaaa ccatcagcaa ggccaagggc    1140
cagccccgcg agccccaggt gtacacactg cccccagcc gggacgagct gaccgagaac    1200
caggtgtccc tgacctgcct ggtgaaaggc ttctacccca gcgatatcgc cgtggaatgg    1260

```
gagagcaacg gccagcccga gaacaactac aagaccaccc cccctgtgct ggacagcgac      1320
ggctcattct tcctgtacag ctggctgacc gtgacaaga gccggtggca gcagggcaac       1380
gtgttcagct gcagcgtgat gcacgaggcc ctgcacaacc actacaccca gaagtccctg      1440
agcctgagcc ccggcaagta g                                                1461
```

```
<210> SEQ ID NO 50
<211> LENGTH: 486
<212> TYPE: PRT
<213> ORGANISM: Artificial Sequence
<220> FEATURE:
<223> OTHER INFORMATION: Synthetic: IFNAR2-Linker_4GS*3-FC EW

<400> SEQUENCE: 50
```

```
Ala Thr Met Trp Trp Arg Leu Trp Trp Leu Leu Leu Leu Leu Leu Leu
1               5                   10                  15

Leu Trp Pro Met Val Trp Ala Ile Ser Tyr Asp Ser Pro Asp Tyr Thr
            20                  25                  30

Asp Glu Ser Cys Thr Phe Lys Ile Ser Leu Arg Asn Phe Arg Ser Ile
        35                  40                  45

Leu Ser Trp Glu Leu Lys Asn His Ser Ile Val Pro Thr His Tyr Thr
    50                  55                  60

Leu Leu Tyr Thr Ile Met Ser Lys Pro Glu Asp Leu Lys Val Val Lys
65                  70                  75                  80

Asn Cys Ala Asn Thr Thr Arg Ser Phe Cys Asp Leu Thr Asp Glu Trp
                85                  90                  95

Arg Ser Thr His Glu Ala Tyr Val Thr Val Leu Glu Gly Phe Ser Gly
            100                 105                 110

Asn Thr Thr Leu Phe Ser Cys Ser His Asn Phe Trp Leu Ala Ile Asp
        115                 120                 125

Met Ser Phe Glu Pro Pro Glu Phe Glu Ile Val Gly Phe Thr Asn His
    130                 135                 140

Ile Asn Val Met Val Lys Phe Pro Ser Ile Val Glu Glu Glu Leu Gln
145                 150                 155                 160

Phe Asp Leu Ser Leu Val Ile Glu Glu Gln Ser Glu Gly Ile Val Lys
                165                 170                 175

Lys His Lys Pro Glu Ile Lys Gly Asn Met Ser Gly Asn Phe Thr Tyr
            180                 185                 190

Ile Ile Asp Lys Leu Ile Pro Asn Thr Asn Tyr Cys Val Ser Val Tyr
        195                 200                 205

Leu Glu His Ser Asp Glu Gln Ala Val Ile Lys Ser Pro Leu Lys Cys
    210                 215                 220

Thr Leu Leu Pro Pro Gly Gln Glu Ser Glu Ser Ala Glu Ser Ala Lys
225                 230                 235                 240

Gly Gly Gly Gly Ser Gly Gly Gly Ser Gly Gly Gly Ser Pro
                245                 250                 255

Lys Ser Cys Asp Lys Thr His Thr Cys Pro Pro Cys Pro Ala Pro Glu
            260                 265                 270

Leu Leu Gly Gly Pro Ser Val Phe Leu Phe Pro Pro Lys Pro Lys Asp
        275                 280                 285

Thr Leu Met Ile Ser Arg Thr Pro Glu Val Thr Cys Val Val Val Asp
    290                 295                 300

Val Ser His Glu Asp Pro Glu Val Lys Phe Asn Trp Tyr Val Asp Gly
305                 310                 315                 320
```

Val Glu Val His Asn Ala Lys Thr Lys Pro Arg Glu Glu Gln Tyr Asn
            325                 330                 335

Ser Thr Tyr Arg Val Val Ser Val Leu Thr Val Leu His Gln Asp Trp
        340                 345                 350

Leu Asn Gly Lys Glu Tyr Lys Cys Lys Val Ser Asn Lys Ala Leu Pro
    355                 360                 365

Ala Pro Ile Glu Lys Thr Ile Ser Lys Ala Lys Gly Gln Pro Arg Glu
370                 375                 380

Pro Gln Val Tyr Thr Leu Pro Pro Ser Arg Asp Glu Leu Thr Glu Asn
385                 390                 395                 400

Gln Val Ser Leu Thr Cys Leu Val Lys Gly Phe Tyr Pro Ser Asp Ile
                405                 410                 415

Ala Val Glu Trp Glu Ser Asn Gly Gln Pro Glu Asn Asn Tyr Lys Thr
            420                 425                 430

Thr Pro Pro Val Leu Asp Ser Asp Gly Ser Phe Phe Leu Tyr Ser Trp
        435                 440                 445

Leu Thr Val Asp Lys Ser Arg Trp Gln Gln Gly Asn Val Phe Ser Cys
    450                 455                 460

Ser Val Met His Glu Ala Leu His Asn His Tyr Thr Gln Lys Ser Leu
465                 470                 475                 480

Ser Leu Ser Pro Gly Lys
                485

<210> SEQ ID NO 51
<211> LENGTH: 1461
<212> TYPE: DNA
<213> ORGANISM: Artificial Sequence
<220> FEATURE:
<223> OTHER INFORMATION: Synthetic: IFNAR2-Linker_4GS*3-FC RVT

<400> SEQUENCE: 51

| | |
|---|---:|
| gccaccatgt ggtggcgtct gtggtggctg ctgcttctgc tgttgctgct gtggcctatg | 60 |
| gtctgggcca tctcctacga cagccctgac tacaccgacg agtcctgcac cttcaagatc | 120 |
| tccctgcgga acttccggtc catcctgtcc tgggagctga gaaccactc catcgtgccc | 180 |
| acacactaca ccctgctgta caccatcatg tccaagcctg aggacctgaa ggtggtcaag | 240 |
| aactgcgcca acaccaccag atctttctgc gacctgaccg atgagtggcg gtctacccac | 300 |
| gaggcttacg tgacagtgct ggaaggcttc tccggcaata ccacactgtt cagctgctcc | 360 |
| cacaacttct ggctggccat cgacatgtcc ttcgagcctc cagagttcga gatcgtgggc | 420 |
| ttcaccaacc acatcaacgt gatggtcaag ttccccagca tcgtggaaga ggaactccag | 480 |
| ttcgacctga gcctggtcat cgaggaacag tccgagggca tcgtgaagaa gcacaagccc | 540 |
| gagatcaagg gcaacatgtc cggcaacttc acctacatca tcgacaagct gatccccaac | 600 |
| accaactact gcgtgtccgt gtacctggaa cactccgatg agcaggccgt gatcaagtcc | 660 |
| cctctgaagt gtaccctgct gcctcctggc caagagtctg agtctgccga gtctgctaaa | 720 |
| ggcggcggag gatctggcgg aggtggaagc ggaggcggtg gatctcccaa gagctgcgac | 780 |
| aagacccaca cctgtccccc ctgccctgcc cctgaactgc tgggcggacc cagcgtgttc | 840 |
| ctgttccccc caaagcccaa ggacaccctg atgatcagcc ggacccccga agtgacctgc | 900 |
| gtggtggtgg acgtgtccca cgaggaccct gaagtgaagt tcaattggta cgtggacggc | 960 |
| gtggaagtgc acaacgccaa gaccaagccc agagaggaac agtacaacag cacctaccgg | 1020 |
| gtggtgtccg tgctgaccgt gctgcaccag gactggctga acggcaaaga gtacaagtgc | 1080 |

```
aaggtgtcca acaaggccct gcctgccccc atcgagaaaa ccatcagcaa ggccaagggc    1140
cagccccgcg agcccggggt gtacacactg ccccccagcc gggacgagct gaccaagaac    1200
caggtgtccc tgacctgcct ggtgaaaggc ttctacccca gcgatatcgc cgtggaatgg    1260
gagagcaacg gccagcccga gaacaactac aagaccaccc ccctgtgct ggtcagcgac    1320 ggctcattca ccctgtacag caagctgacc gtggacaaga ccggtggca gcagggcaac    1380 gtgttcagct gcagcgtgat gcacgaggcc ctgcacaacc actacaccca gaagtccctg    1440
agcctgagcc ccggcaagta g                                             1461
```

<210> SEQ ID NO 52
<211> LENGTH: 486
<212> TYPE: PRT
<213> ORGANISM: Artificial Sequence
<220> FEATURE:
<223> OTHER INFORMATION: Synthetic: IFNAR2-Linker_4GS*3-FC RVT

<400> SEQUENCE: 52

```
Ala Thr Met Trp Trp Arg Leu Trp Trp Leu Leu Leu Leu Leu Leu
1               5                   10                  15

Leu Trp Pro Met Val Trp Ala Ile Ser Tyr Asp Ser Pro Asp Tyr Thr
            20                  25                  30

Asp Glu Ser Cys Thr Phe Lys Ile Ser Leu Arg Asn Phe Arg Ser Ile
        35                  40                  45

Leu Ser Trp Glu Leu Lys Asn His Ser Ile Val Pro Thr His Tyr Thr
    50                  55                  60

Leu Leu Tyr Thr Ile Met Ser Lys Pro Glu Asp Leu Lys Val Val Lys
65                  70                  75                  80

Asn Cys Ala Asn Thr Thr Arg Ser Phe Cys Asp Leu Thr Asp Glu Trp
                85                  90                  95

Arg Ser Thr His Glu Ala Tyr Val Thr Val Leu Glu Gly Phe Ser Gly
            100                 105                 110

Asn Thr Thr Leu Phe Ser Cys Ser His Asn Phe Trp Leu Ala Ile Asp
        115                 120                 125

Met Ser Phe Glu Pro Pro Glu Phe Glu Ile Val Gly Phe Thr Asn His
    130                 135                 140

Ile Asn Val Met Val Lys Phe Pro Ser Ile Val Glu Glu Glu Leu Gln
145                 150                 155                 160

Phe Asp Leu Ser Leu Val Ile Glu Glu Gln Ser Glu Gly Ile Val Lys
                165                 170                 175

Lys His Lys Pro Glu Ile Lys Gly Asn Met Ser Gly Asn Phe Thr Tyr
            180                 185                 190

Ile Ile Asp Lys Leu Ile Pro Asn Thr Asn Tyr Cys Val Ser Val Tyr
        195                 200                 205

Leu Glu His Ser Asp Glu Gln Ala Val Ile Lys Ser Pro Leu Lys Cys
    210                 215                 220

Thr Leu Leu Pro Pro Gly Gln Glu Ser Glu Ser Ala Glu Ser Ala Lys
225                 230                 235                 240

Gly Gly Gly Gly Ser Gly Gly Gly Gly Ser Gly Gly Gly Gly Ser Pro
                245                 250                 255

Lys Ser Cys Asp Lys Thr His Thr Cys Pro Pro Cys Pro Ala Pro Glu
            260                 265                 270

Leu Leu Gly Gly Pro Ser Val Phe Leu Phe Pro Pro Lys Pro Lys Asp
        275                 280                 285

Thr Leu Met Ile Ser Arg Thr Pro Glu Val Thr Cys Val Val Val Asp
```

```
                    290                 295                 300

Val Ser His Glu Asp Pro Glu Val Lys Phe Asn Trp Tyr Val Asp Gly
305                 310                 315                 320

Val Glu Val His Asn Ala Lys Thr Lys Pro Arg Glu Glu Gln Tyr Asn
                325                 330                 335

Ser Thr Tyr Arg Val Val Ser Val Leu Thr Val Leu His Gln Asp Trp
            340                 345                 350

Leu Asn Gly Lys Glu Tyr Lys Cys Lys Val Ser Asn Lys Ala Leu Pro
        355                 360                 365

Ala Pro Ile Glu Lys Thr Ile Ser Lys Ala Lys Gly Gln Pro Arg Glu
    370                 375                 380

Pro Arg Val Tyr Thr Leu Pro Pro Ser Arg Asp Glu Leu Thr Lys Asn
385                 390                 395                 400

Gln Val Ser Leu Thr Cys Leu Val Lys Gly Phe Tyr Pro Ser Asp Ile
                405                 410                 415

Ala Val Glu Trp Glu Ser Asn Gly Gln Pro Glu Asn Asn Tyr Lys Thr
            420                 425                 430

Thr Pro Pro Val Leu Val Ser Asp Gly Ser Phe Thr Leu Tyr Ser Lys
        435                 440                 445

Leu Thr Val Asp Lys Ser Arg Trp Gln Gln Gly Asn Val Phe Ser Cys
    450                 455                 460

Ser Val Met His Glu Ala Leu His Asn His Tyr Thr Gln Lys Ser Leu
465                 470                 475                 480

Ser Leu Ser Pro Gly Lys
                485

<210> SEQ ID NO 53
<211> LENGTH: 5
<212> TYPE: PRT
<213> ORGANISM: Artificial Sequence
<220> FEATURE:
<223> OTHER INFORMATION: Synthetic: Linker_4GS

<400> SEQUENCE: 53

Gly Gly Gly Gly Ser
1               5

<210> SEQ ID NO 54
<211> LENGTH: 10
<212> TYPE: PRT
<213> ORGANISM: Artificial Sequence
<220> FEATURE:
<223> OTHER INFORMATION: Synthetic: Linker_4GS*2

<400> SEQUENCE: 54

Gly Gly Gly Gly Ser Gly Gly Gly Gly Ser
1               5                   10

<210> SEQ ID NO 55
<211> LENGTH: 20
<212> TYPE: PRT
<213> ORGANISM: Artificial Sequence
<220> FEATURE:
<223> OTHER INFORMATION: Synthetic: Linker_4GS*4

<400> SEQUENCE: 55

Gly Gly Gly Gly Ser Gly Gly Gly Gly Ser Gly Gly Gly Gly Ser Gly
1               5                   10                  15

Gly Gly Gly Ser
            20
```

<210> SEQ ID NO 56
<211> LENGTH: 6
<212> TYPE: PRT
<213> ORGANISM: Artificial Sequence
<220> FEATURE:
<223> OTHER INFORMATION: Synthetic: Linker_6G

<400> SEQUENCE: 56

Gly Gly Gly Gly Gly Gly
1               5

<210> SEQ ID NO 57
<211> LENGTH: 8
<212> TYPE: PRT
<213> ORGANISM: Artificial Sequence
<220> FEATURE:
<223> OTHER INFORMATION: Synthetic: Linker_8G

<400> SEQUENCE: 57

Gly Gly Gly Gly Gly Gly Gly Gly
1               5

<210> SEQ ID NO 58
<211> LENGTH: 12
<212> TYPE: PRT
<213> ORGANISM: Artificial Sequence
<220> FEATURE:
<223> OTHER INFORMATION: Synthetic: Linker_AEAAAKEAAAKA

<400> SEQUENCE: 58

Ala Glu Ala Ala Ala Lys Glu Ala Ala Ala Lys Ala
1               5                   10

<210> SEQ ID NO 59
<211> LENGTH: 46
<212> TYPE: PRT
<213> ORGANISM: Artificial Sequence
<220> FEATURE:
<223> OTHER INFORMATION: Synthetic: Linker_EAAAK complex

<400> SEQUENCE: 59

Ala Glu Ala Ala Ala Lys Glu Ala Ala Ala Lys Glu Ala Ala Ala Lys
1               5                   10                  15

Glu Ala Ala Ala Lys Ala Leu Glu Ala Glu Ala Ala Lys Glu Ala
            20                  25                  30

Ala Ala Lys Glu Ala Ala Ala Lys Glu Ala Ala Lys Ala
            35                  40                  45

<210> SEQ ID NO 60
<211> LENGTH: 15
<212> TYPE: PRT
<213> ORGANISM: Artificial Sequence
<220> FEATURE:
<223> OTHER INFORMATION: Synthetic: Linker_EAAAK*3

<400> SEQUENCE: 60

Glu Ala Ala Ala Lys Glu Ala Ala Ala Lys Glu Ala Ala Ala Lys
1               5                   10                  15

<210> SEQ ID NO 61
<211> LENGTH: 5
<212> TYPE: PRT
<213> ORGANISM: Artificial Sequence
<220> FEATURE:
<223> OTHER INFORMATION: Synthetic: Linker_EAAAK

```
<400> SEQUENCE: 61

Glu Ala Ala Ala Lys
1               5

<210> SEQ ID NO 62
<211> LENGTH: 10
<212> TYPE: PRT
<213> ORGANISM: Artificial Sequence
<220> FEATURE:
<223> OTHER INFORMATION: Synthetic: Linker_EAAAK*2

<400> SEQUENCE: 62

Glu Ala Ala Ala Lys Glu Ala Ala Ala Lys
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Synthetic: Linker_AP*5

<400> SEQUENCE: 63

Ala Pro Ala Pro Ala Pro Ala Pro Ala Pro
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Synthetic: Linker_AP*6

<400> SEQUENCE: 64

Ala Pro Ala Pro Ala Pro Ala Pro Ala Pro Ala Pro
1               5                   10

<210> SEQ ID NO 65
<211> LENGTH: 14
<212> TYPE: PRT
<213> ORGANISM: Artificial Sequence
<220> FEATURE:
<223> OTHER INFORMATION: Synthetic: Linker_AP*7

<400> SEQUENCE: 65

Ala Pro Ala Pro Ala Pro Ala Pro Ala Pro Ala Pro Ala Pro
1               5                   10

<210> SEQ ID NO 66
<211> LENGTH: 16
<212> TYPE: PRT
<213> ORGANISM: Artificial Sequence
<220> FEATURE:
<223> OTHER INFORMATION: Synthetic: Linker_AP*8

<400> SEQUENCE: 66

Ala Pro Ala Pro Ala Pro Ala Pro Ala Pro Ala Pro Ala Pro Ala Pro
1               5                   10                  15

<210> SEQ ID NO 67
<211> LENGTH: 18
<212> TYPE: PRT
<213> ORGANISM: Artificial Sequence
<220> FEATURE:
<223> OTHER INFORMATION: Synthetic: Linker_AP*9
```

```
<400> SEQUENCE: 67

Ala Pro Ala Pro Ala Pro Ala Pro Ala Pro Ala Pro Ala Pro Ala Pro
1               5                   10                  15

Ala Pro

<210> SEQ ID NO 68
<211> LENGTH: 20
<212> TYPE: PRT
<213> ORGANISM: Artificial Sequence
<220> FEATURE:
<223> OTHER INFORMATION: Synthetic: Linker_AP*10

<400> SEQUENCE: 68

Ala Pro Ala Pro Ala Pro Ala Pro Ala Pro Ala Pro Ala Pro Ala Pro
1               5                   10                  15

Ala Pro Ala Pro
            20

<210> SEQ ID NO 69
<211> LENGTH: 22
<212> TYPE: PRT
<213> ORGANISM: Artificial Sequence
<220> FEATURE:
<223> OTHER INFORMATION: Synthetic: Linker_AP*11

<400> SEQUENCE: 69

Ala Pro Ala Pro Ala Pro Ala Pro Ala Pro Ala Pro Ala Pro Ala Pro
1               5                   10                  15

Ala Pro Ala Pro Ala Pro
            20

<210> SEQ ID NO 70
<211> LENGTH: 24
<212> TYPE: PRT
<213> ORGANISM: Artificial Sequence
<220> FEATURE:
<223> OTHER INFORMATION: Synthetic: Linker_AP*12

<400> SEQUENCE: 70

Ala Pro Ala Pro Ala Pro Ala Pro Ala Pro Ala Pro Ala Pro Ala Pro
1               5                   10                  15

Ala Pro Ala Pro Ala Pro Ala Pro
            20

<210> SEQ ID NO 71
<211> LENGTH: 26
<212> TYPE: PRT
<213> ORGANISM: Artificial Sequence
<220> FEATURE:
<223> OTHER INFORMATION: Synthetic: Linker_AP*13

<400> SEQUENCE: 71

Ala Pro Ala Pro Ala Pro Ala Pro Ala Pro Ala Pro Ala Pro Ala Pro
1               5                   10                  15

Ala Pro Ala Pro Ala Pro Ala Pro Ala Pro
            20                  25

<210> SEQ ID NO 72
<211> LENGTH: 28
<212> TYPE: PRT
<213> ORGANISM: Artificial Sequence
<220> FEATURE:
<223> OTHER INFORMATION: Synthetic: Linker_AP*14
```

```
<400> SEQUENCE: 72

Ala Pro Ala Pro Ala Pro Ala Pro Ala Pro Ala Pro Ala Pro Ala Pro
1               5                   10                  15

Ala Pro Ala Pro Ala Pro Ala Pro Ala Pro
            20                  25

<210> SEQ ID NO 73
<211> LENGTH: 30
<212> TYPE: PRT
<213> ORGANISM: Artificial Sequence
<220> FEATURE:
<223> OTHER INFORMATION: Synthetic: Linker_AP*15

<400> SEQUENCE: 73

Ala Pro Ala Pro Ala Pro Ala Pro Ala Pro Ala Pro Ala Pro Ala Pro
1               5                   10                  15

Ala Pro Ala Pro Ala Pro Ala Pro Ala Pro Ala Pro Ala Pro
            20                  25                  30

<210> SEQ ID NO 74
<211> LENGTH: 32
<212> TYPE: PRT
<213> ORGANISM: Artificial Sequence
<220> FEATURE:
<223> OTHER INFORMATION: Synthetic: Linker_AP*16

<400> SEQUENCE: 74

Ala Pro Ala Pro Ala Pro Ala Pro Ala Pro Ala Pro Ala Pro Ala Pro
1               5                   10                  15

Ala Pro Ala Pro Ala Pro Ala Pro Ala Pro Ala Pro Ala Pro Ala Pro
            20                  25                  30

<210> SEQ ID NO 75
<211> LENGTH: 34
<212> TYPE: PRT
<213> ORGANISM: Artificial Sequence
<220> FEATURE:
<223> OTHER INFORMATION: Synthetic: Linker_AP*17

<400> SEQUENCE: 75

Ala Pro Ala Pro Ala Pro Ala Pro Ala Pro Ala Pro Ala Pro Ala Pro
1               5                   10                  15

Ala Pro Ala Pro Ala Pro Ala Pro Ala Pro Ala Pro Ala Pro Ala Pro
            20                  25                  30

Ala Pro

<210> SEQ ID NO 76
<211> LENGTH: 5
<212> TYPE: PRT
<213> ORGANISM: Artificial Sequence
<220> FEATURE:
<223> OTHER INFORMATION: Synthetic: Linker_PAPAP

<400> SEQUENCE: 76

Pro Ala Pro Ala Pro
1               5
```

TYPE 1 INTERFERON NEUTRALIZING FC-FUSION PROTEIN AND USE THEREOF

CROSS-REFERENCE TO RELATED APPLICATIONS

This application is a national phase entry under 35 U.S.C. 371 of PCT International Application No. PCT/KR2019/018233 filed Dec. 20, 2019, which claims priority to Korean Patent Application No. No. 10-2018-0168801 filed on Dec. 24, 2018, the disclosure of each of these applications is expressly incorporated herein by reference in their entirety.

REFERENCE TO SEQUENCE LISTING SUBMITTED VIA EFS-WEB

This application includes an electronically submitted sequence listing in .txt format. The .txt file contains a sequence listing entitled "2650-11_ST25.txt" created on Jun. 24, 20201 and is 136,981 bytes in size. The sequence listing contained in this .txt file is part of the specification and is hereby incorporated by reference herein in its entirety.

TECHNICAL FIELD

The present invention relates to a type 1 interferon neutralizing Fc-fusion protein and use thereof, more specifically, it relates to a dimeric polypeptide in which a monomer comprising an interferon receptor fragment or an antibody Fc fragment is bound, and a method for preparing the same, and a composition for preventing or treating diseases related to abnormal expression of type 1 interferon or interferon-inducible gene comprising the same.

BACKGROUND OF THE INVENTION

Type I interferons (IFNs) (IFN-α, IFN-β, INF-ω, IFN-τ) are a group of structurally related cytokines with antiviral, antitumor and immunomodulatory effects. The human IFNα locus has two subgroups. The first subgroup has 14 non-alleles and 4 pseudogenes with at least 80% identity. The second subgroup, αII or omega (ω), has 1 functional gene and 5 pseudogenes showing 70% identity to the IFNα gene. The subtypes of IFNα have different specific activities, but show the same biological spectrum and have the same cellular receptors. Interferon β (IFN β) is encoded by a single gene with nearly 50% identity to the IFNα gene. Interferon γ produced by activated lymphocytes has no identity with alpha/beta interferon and does not react with their receptors.

All human type I IFNs bind to a cell surface receptor (IFN alpha receptor, IFNAR), which consists of two transmembrane proteins, IFNAR-1 and IFNAR-2. IFNAR-1 is essential for the high affinity binding and different specificity of the IFNAR complex. Although the difference in the function of each type I IFN subtype has not been elucidated, it is thought that each exhibits a different action with the IFNAR receptor component, potentially leading to various signaling.

Early studies of the function of type I IFN have focused on innate defenses against viral infection. However, more recent studies relate to type I IFNs as potent immunoregulatory cytokines in adaptive immune response. In particular, type I IFN has been shown to facilitate the mutation of native T cells in the Th1 pathway, increase antibody production, and support the functional activity and survival of memory T cells.

Several groups of recent studies have suggested that IFN-α can enhance the maturation or activation of dendritic cells (DCs). Moreover, increased expression of type I interferon has been described in a number of autoimmune diseases related literature.

The most studied example of this is insulin-dependent diabetes mellitus (IDDM) (Paulis et al. (1987) Lancet 2:1423), systemic lupus erythematosus (SLE) (Hooks et al. (1982) Arthritis Rheum. 25:396), Sjogren's syndrome (Lee Hong-Yau et al. (2013) Autoimmun Rev. 12(5):558-66), inflammatory myositis (Beckler et al. (2007) Mol Med. 13 (1-2): 59-68) and rheumatoid arthritis (RA) in which IFN-β plays a more important role (Herzzog et al. (1988) Clin. Immunol. Immunopathol. 48:192, Hopkins and Meggle (1988) Clin. Exp. Immunol. 73:88, Alvin and Miller (1984) Arthritis Rheum. 27:582), which is all associated with elevated levels of IFNα.

Moreover, it has been reported that administration of interferon α, a representative type of type 1 interferon, exacerbates the underlying disease in patients with psoriasis and multiple sclerosis and induces SLE-like symptoms in patients without prior experience of autoimmune disease. Interferon α has also been shown to induce glomerulonephritis in normal mice and accelerate the development of concomitant autoimmune disease in NZB/W mice. Furthermore, IFN-α therapy has been shown to induce undesirable side effects including fever and neurological disorders in some cases.

Although it has the diversity of type 1 IFN, and in recent studies on SLE patients, not only IFN-α but also IFN-β acts as the etiology for mucosal skin diseases, there is a problem in that the treatment for type 1 interferon-mediated disease is concentrated on IFN-α alone, such as a vaccine (IFN-kinoid) or anti-IFN-α monoclonal neutralizing antibody (Sifalimumab, Rontalizumab, AGS-009) treatment. In addition, the problem of such neutralizing antibodies is that they cannot neutralize all the parts that bind to two different receptors of interferon, and have binding ability only to IFNAR1 or IFNAR2. In order to compensate for this problem, Anifrolumab (MAbs. 2015 March-April; 7(2): 428-439) that specifically binds to IFNAR1, a type I IFN receptor, and exhibits neutralizing ability is being developed. However, the characteristics of these neutralizing antibody therapeutics in various signaling mechanisms of type 1 interferon are expected that there will be a limitation in inability to remove type 1 interferon from the body and complex signaling mechanisms such as non-canonical pathways mediated by IFNAR1 (Nat Immunol. 2013 September; 14(9):901-7) or IFNAR2 (Sci Signal. 2014 May 27; 7 (327):ra50; PLoS One. 2017; 12 (8): e0182866) other than the canonical pathways mediated by IFNAR1 and IFNAR2.

DETAILED DESCRIPTION OF THE INVENTION

Technical Problem

The inventors of the present invention have completed the present invention, while developing a treatment for type 1 interferon-mediated disease, as it confirmed that the dimer-type polypeptide comprising the interferon receptor 1 fragment and the interferon receptor 2 fragment not only binds to type 1 interferon, but also significantly inhibits the inhibition of signaling mechanism initiation and biological activity during treatment.

Therefore, the object of the present invention is to provide a dimeric polypeptide in which a monomer comprising an interferon receptor fragment or an antibody Fc fragment is bounded, Wherein the monomer is a polypeptide selected from the group consisting of (i), (ii) and (iii):
(i) a monomer comprising an interferon receptor 1 (IFNAR1) fragment and an antibody Fc fragment;
(ii) a monomer comprising an interferon receptor 2 (IFNAR2) fragment and an antibody Fc fragment; and
(iii) an antibody Fc fragment.

Another object of the present invention is to provide a polynucleotide encoding the polypeptide.

Another object of the present invention is to provide a vector comprising the polynucleotide.

Another object of the present invention is to provide a host cell transformed with the vector.

Another object of the present invention is to provide a method for producing the polypeptide comprising:
(a) providing the host cell;
(b) culturing the provided cells; and
(c) preparing the polypeptide by recovering the polypeptide from the cell or culture medium.

Another object of the present invention is
to provide a pharmaceutical composition for preventing or treating a type 1 interferon-mediated disease or disorder comprising a polypeptide as an active ingredient.
also, to provide a pharmaceutical composition for preventing or treating a type 1 interferon-mediated disease or disorder consisting of a polypeptide as an active ingredient.
also, to provide a pharmaceutical composition for preventing or treating a type 1 interferon-mediated disease or disorder consisting essentially of a polypeptide as an active ingredient.

Another object of the present invention is to provide a use of the polypeptide for the preparation of an agent for the prevention or treatment of a type 1 interferon-mediated disease or disorder.

Another object of the present invention is to provide a method of treating a type 1 interferon-mediated disease or disorder, comprising administering to a subject in need thereof an effective amount of a composition comprising the polypeptide as an active ingredient

Technical Solution

Accordingly, the present invention in order to achieve the object of the present invention provides,
a dimeric polypeptide in which a monomer comprising an interferon receptor fragment or an antibody Fc fragment is bounded,
Wherein the monomer is a polypeptide selected from the group consisting of (i), (ii) and (iii):
(i) a monomer comprising an interferon receptor 1 (IFNAR1) fragment and an antibody Fc fragment;
(ii) a monomer comprising an interferon receptor 2 (IFNAR2) fragment and an antibody Fc fragment; and
(iii) an antibody Fc fragment.

In order to achieve another object of the present invention, the present invention provides a polynucleotide encoding the polypeptide.

In order to achieve another object of the present invention, the present invention provides a vector comprising the polynucleotide.

In order to achieve another object of the present invention, the present invention provides a host cell transformed with the vector.

In order to achieve another object of the present invention, the present invention provides a method for producing the polypeptide comprising:
(a) providing the host cell;
(b) culturing the provided cells; and
(c) preparing the polypeptide by recovering the polypeptide from the cell or culture medium.

In order to achieve another object of the present invention, the present invention, provides a pharmaceutical composition for prevention or treatment of type 1 interferon-mediated diseases or disorders comprising the polypeptide as an active ingredient.

In addition, provides a pharmaceutical composition for preventing or treating a type 1 interferon-mediated disease or disorder consisting of a polypeptide as an active ingredient.

In addition, provides a pharmaceutical composition for preventing or treating a type 1 interferon-mediated disease or disorder consisting essentially of a polypeptide as an active ingredient.

In order to achieve another object of the present invention, the present invention provides a use of the polypeptide for the preparation of an agent for the prevention or treatment of a type 1 interferon-mediated disease or disorder.

In order to achieve another object of the present invention, the present invention provides a method of treating a type 1 interferon-mediated disease or disorder, comprising administering to a subject in need thereof an effective amount of a composition comprising the polypeptide as an active ingredient.

Hereinafter, the present invention will be described in detail.

Therefore, the present invention is a dimeric polypeptide in which a monomer comprising an interferon receptor fragment or an antibody Fc fragment is bounded, wherein the monomer provide a polypeptide selected from the group consisting of (i), (ii) and (iii):
(i) a monomer comprising an interferon receptor 1 (IFNAR1) fragment and an antibody Fc fragment;
(ii) a monomer comprising an interferon receptor 2 (IFNAR2) fragment and an antibody Fc fragment; and
(iii) an antibody Fc fragment.

In the present specification including the claims, the term "interferon receptor fragment" is meant to include all polypeptides having human interferon receptor activity while having all or part of an amino acid sequence derived from a native human interferon receptor.

The terms "interferon receptor 1" "IFNAR 1" and "IFNAR-1 antigen" are used interchangeably, and variants, isoforms, species isoforms of human IFNAR 1 and analogs having at least one common epitope of IFNAR 1 are included. Thus, the polypeptides of the invention may in some cases cross-react with IFNAR 1 from other non-human species or other proteins structurally associated with human IFNAR 1 (e.g., human IFNAR-1 homologs). In other cases, the polypeptide may be intactly specific for human IFNAR-1 and does not represent a species or other type of cross-reactivity. The complete cDNA sequence of human IFNAR 1 has genbank accession number XM_005260964.2, NM_000629.2, or XM_011529552.2.

The nucleotide sequence used in the present invention may include the extracellular domain (28-436a.a.; P17181-1) of the sequence of IFNAR 1 Isoform 1 (genebank accession number: NM_000629.2), and may include a part of the nucleotide sequence. The IFNAR 1 fragment of the present invention may preferably be an interferon receptor 1 comprising the amino acid sequence represented by SEQ ID NO: 4, more preferably, it may be an interferon receptor 1 consisting of the amino acid sequence represented by SEQ ID NO: 4.

In one embodiment of the present invention, the polypeptide was prepared using the interferon receptor 1 comprising the amino acid sequence (Polynucleotide sequence represented by SEQ ID NO: 3—The polynucleotide sequence may include a stop codon. Hereinafter, it is the same for all DNA sequences) represented by SEQ ID NO: 4.

The terms "interferon receptor 2" "IFNAR 2" and "IFNAR-2 antigen" are used interchangeably, variants, isoforms, species isoforms of human IFNAR 2 and analogs having at least one common epitope of IFNAR 2 are included. Thus, the polypeptides of the invention may in some instances cross-react with IFNAR 2 from other non-human species or other proteins structurally related to human IFNAR 2 (e.g., human IFNAR-2 homologs). In other cases, the polypeptide may be intactly specific for human IFNAR-2 and does not represent a species or other type of cross-reactivity. The complete cDNA sequence of human IFNAR 2 has genbank accession number NM_000874.4, NM_001289125.1, or NM_001289126.1. The nucleotide sequence used in the present invention may include the extracellular domain (27-243a.a.; P48551-1) of the sequence of Isoform 1 of human IFNAR2 (genebank accession number: NM_001289125.1), may include a part of the nucleotide sequence. The IFNAR 2 fragment of the present invention may preferably be an interferon receptor 2 comprising the amino acid sequence represented by SEQ ID NO: 6, more preferably, it may be an interferon receptor 2 consisting of the amino acid sequence represented by SEQ ID NO: 6.

In one embodiment of the present invention, the polypeptide was prepared using an interferon receptor 2 fragment comprising the amino acid sequence (Polynucleotide sequence represented by SEQ ID NO: 5) represented by SEQ ID NO: 6.

In addition, the term "polypeptide having all or part of an amino acid sequence derived from an interferon receptor fragment" is meant to include a polypeptide comprising all or a substantial part of the amino acid sequence of SEQ ID NO: 4 or SEQ ID NO: 6, which is the amino acid sequence of a native interferon receptor fragment, or a polypeptide substantially similar to such a polypeptide.

Here, the "polypeptide comprising a substantial portion of the entire amino acid sequence of SEQ ID NO: 4 or SEQ ID NO: 6" is defined as a polypeptide comprising having an activity equal to or higher than that of the native interferon receptor having the amino acid sequence of SEQ ID NO: 4 or SEQ ID NO: 6, or a portion of the amino acid sequence of SEQ ID NO: 4 or SEQ ID NO: 6 comprising one or more substituted amino acids while still retaining the activity of the interferon receptor, although low in activity. The "polypeptide substantially similar to all or a substantial part of the amino acid sequence set forth in SEQ ID NO: 4 or SEQ ID NO: 6" is defined as a polypeptide comprising having an activity equal to or higher than that of the interferon receptor of SEQ ID NO: 4 or SEQ ID NO: 6, or the whole or a substantial portion of the amino acid sequence of SEQ ID NO: 4 or SEQ ID NO: 6 comprising one or more substituted amino acids while still retaining the activity of the interferon receptor, although low in activity.

There may be cases in which an N-terminal portion and/or a C-terminal portion are deleted in a polypeptide comprising the amino acid sequence set forth in SEQ ID NO: 4 or SEQ ID NO: 6 as a polypeptide comprising a substantial portion of the entire amino acid sequence set forth in SEQ ID NO: 4 or SEQ ID NO: 6, and there may be cases that even if one or more amino acids are substituted, if the amino acid before the substitution is chemically equivalent to the substituted amino acid, for example, when alanine, which is a hydrophobic amino acid, is substituted with another hydrophobic amino acid, in particular, a case where it is substituted with a more hydrophobic amino acid, for example, valine, leucine or isoleucine as a polypeptide substantially similar to all or a substantial part of the amino acid sequence set forth in SEQ ID NO: 4 or SEQ ID NO: 6.

In the present invention, "fusion" refers to integrating two molecules with different or the same function or structure, and may be fusion by any physical, chemical or biological method capable of binding the antibody Fc portion or each monomer to the interferon receptor.

The fusion is preferably by a linker peptide, which may bind to, for example, the C-terminus of an Fc fragment of an antibody.

"Antibody Fc fragment" may be an Fc fragment of an IgA, IgM, IgE, IgD, or IgG antibody, or a modification thereof. In one embodiment, the fragment is an Fc fragment (e.g., Fc fragment of an IgG1, IgG2a, IgG2b, IgG3, or IgG4 antibody) of an IgG antibody. In addition, the polypeptide comprising the Fc fragment of the present invention may be partially or entirely glycosylated or non-glycosylated. In addition, the polypeptide may include one or more regions derived from an antibody in addition to the Fc fragment. Additionally, the polypeptide may include an antibody-derived antigen binding domain, and a plurality of polypeptides may form an antibody or antibody-like protein.

In the present specification, amino acid residue number of antibody Fc fragments is according to the Kabat numbering system commonly used in the art (EU index number as in Kabat et al., in of Proteins of Immunological Interest 5th Ed., U.S. Department of Health and Human Services, NIH Publication No. 91-3242, 1991).

According to an embodiment of the present invention, it may include the wild-type Fc fragment of the present invention as well as a substituted Fc variant.

The wild-type Fc fragment sequence of the present invention may comprise the amino acid represented by SEQ ID NO: 8, and preferably, may consist of the amino acid represented by SEQ ID NO: 8.

The substituted Fc fragment of the present invention comprises one or more amino acid substitutions selected from the group consisting of Q347R, K360E, D399V, F405T and K409W according to the Kabat numbering system.

The substituted Fc fragment of the present invention may be one comprising K360E and K409W amino acid substitutions, preferably, it may comprise the amino acid sequence represented by SEQ ID NO: 12, more preferably, it may consist of the amino acid sequence represented by SEQ ID NO: 12.

The substituted Fc fragment of the present invention may be one comprising Q347R, D399V, and F405T amino acid substitutions, preferably, it may consist of the amino acid sequence represented by SEQ ID NO: 14, more preferably, it may consist of SEQ ID NO: 14.

In addition, the antibody Fc fragment as a monomer forming a dimer comprises SEQ ID NO: 8, SEQ ID NO: 12 or SEQ ID NO: 14, and a linker or other short fragment peptide may be attached to the N-terminus or C-terminus. The linker may be a linker comprising an amino acid sequence selected from the group consisting of SEQ ID NO: 10, SEQ ID NO: 34, and SEQ ID NO: 53 to SEQ ID NO: 76. The antibody Fc fragment as a monomer may consist of an amino acid sequence selected from the group consisting of SEQ ID NO: 8, SEQ ID NO: 12, SEQ ID NO: 14, SEQ ID NO: 16, SEQ ID NO: 18, SEQ ID NO: 20, SEQ ID NO: 36, SEQ ID NO: 38 and SEQ ID NO: 40.

"Monomer comprising interferon receptor 1 (IFNAR1) fragment and antibody Fc fragment" of the present invention preferably may one comprising i) an interferon receptor 1 (IFNAR1) fragment comprising the amino acid sequence represented by SEQ ID NO: 4 and ii) an antibody Fc fragment comprising an amino acid sequence selected from the group consisting of SEQ ID NO: 8, SEQ ID NO: 12 and SEQ ID NO: 14, more preferably, it may one comprising i) an interferon receptor 1 (IFNAR1) fragment comprising the amino acid sequence represented by SEQ ID NO: 4, ii) a linker comprising an amino acid sequence selected from the group consisting of SEQ ID NO: 10, SEQ ID NO: 34, and SEQ ID NO: 53 to SEQ ID NO: 76, and iii) an antibody Fc fragment comprising an amino acid sequence selected from the group consisting of SEQ ID NO: 8, SEQ ID NO: 12 and SEQ ID NO: 14, most preferably, it may be a monomer comprising or consisting of an amino acid selected from the group consisting of SEQ ID NO: 22, SEQ ID NO: 24, SEQ ID NO: 26, SEQ ID NO: 42, SEQ ID NO: 44 and SEQ ID NO: 46.

The "monomer comprising the interferon receptor 2 (IFNAR2) fragment and the antibody Fc fragment" of the present invention is preferably may one comprising i) an interferon receptor 2 (IFNAR2) fragment comprising the amino acid sequence represented by SEQ ID NO: 6 and ii) an antibody Fc fragment comprising an amino acid sequence selected from the group consisting of SEQ ID NO: 8, SEQ ID NO: 12 and SEQ ID NO: 14, more preferably, it may one comprising i) an interferon receptor 2 (IFNAR2) fragment comprising the amino acid sequence represented by SEQ ID NO: 6, ii) a linker comprising an amino acid sequence selected from the group consisting of SEQ ID NO: 10, SEQ ID NO: 34, SEQ ID NO: 53 to SEQ ID NO: 76 and iii) an antibody Fc fragment comprising an amino acid sequence selected from the group consisting of SEQ ID NO: 8, SEQ ID NO: 12 and SEQ ID NO: 14, most preferably, it may be a monomer comprising or consisting of amino acids selected from the group consisting of SEQ ID NO: 28, SEQ ID NO: 30, SEQ ID NO: 32, SEQ ID NO: 48, SEQ ID NO: 50 and SEQ ID NO: 52.

The polypeptide of the present invention may be one that neutralizes type I interferon, and thus can be used as a type I interferon neutralizing antibody.

As used herein, the term "type I interferon" is intended to refer to the multiple class I interferon group (ie, multiple type I interferon groups of molecules capable of binding to IFNAR 1 or IFNAR 2) of molecules that are ligands of IFNAR 1 and IFNAR 2. Examples of type I interferon ligands are interferon alpha 1, 2a, 2b, 4, 5, 6, 7, 8, 10, 14, 16, 17, 21, interferon beta, interferon omega and interferon epsilon.

A person skilled in the art can use the above-described polypeptides without limitation in practicing the present invention.

The present invention also provides a dimeric polypeptide wherein the monomer is linked to the antibody or fragment thereof by a peptide linker. A peptide linker refers to a molecule that connects two or more separate substances to each other as a short fragment of amino acids or amino acid analogs in which amino acids or amino acid-like substances are linked to each other by peptide bonds. Glycine, serine, and alanine are used as major constituent amino acids, so a glycine-serine linker, a glycine-serine-alanine linker, etc. can be used, and according to a preferred embodiment of the present invention, the linker may consist of or comprise an amino acid sequence represented by SEQ ID NO: 8 and SEQ ID NO: 10.

Polypeptides of the present invention may preferably comprise a flexible linker sequence inserted between the monomers.

The linker refers to a naturally-derived peptide linker or a synthetically-derived peptide linker. The peptide linker consists of a linear amino acid chain, wherein the 20 naturally occurring amino acids are monomeric building blocks. The linker may have a repetitive amino acid sequence or may have the sequence of a naturally occurring polypeptide, for example, a polypeptide having a hinge function. Since all peptide linkers can be encoded by nucleic acid molecules, they can be expressed in a recombinant method. Since the linker is itself a peptide, each monomer can be linked to the linker via a peptide bond to form a dimer.

The linker consists of amino acids linked together by peptide bonds, preferably 1 to 20 amino acids linked together by peptide bonds, in this case, the amino acid is preferably selected from among 20 natural amino acids. One or more of these amino acids are glycosylated as understood by one of ordinary skill in the art. Preferably, but not limited to, 1 to 20 amino acids are selected from among glycine, alanine, proline, asparagine, glutamine and lysine.

Suitable linkers include, for example, cleavable linkers and non-cleavable linkers. Cleavable linkers are typically readily cleaved under intracellular conditions. Suitable cleavable linkers include, for example, peptide linkers cleavable by intracellular proteases such as lysosomal proteases or endosomal proteases.

The linker is, for example, the N-terminus of the linker is connected to the C-terminus of the interferon receptor. Linking to the C-terminus of the interferon receptor can preferably be directly linked to the antibody expressed by the expression vector as the nucleotide sequence encoding the linker sequence is linked to the expression vector expressing the protein of the present invention so that the protein expression frame coincides. In addition, the N-terminus of the Fc portion of the antibody of the present invention is linked to the C-terminus of the linker.

The peptide linker of the present invention may be a peptide linker known in the art, but preferably a glycine-serine linker, a helix-forming peptide linker, or a peptide linker comprising or consisting of the amino acid sequence of SEQ ID NO: 8 or SEQ ID NO: 10.

The liker is, preferably, a gly-ser linker, for example $(Gly_xSer_y)_z$ type (x is an integer from 1 to 5, y is an integer from 1 to 2, z is an integer from 1 to 6), for example $(gly_4ser_1)_3$ or $(gly_3ser_2)_3$, in the case of a helix-forming peptide linker (or rigid helical linker), it may be $A(EAAAK)_n$ A (n=an integer from 2 to 5).

Preferably, the peptide linker of the present invention may be GGGGS, $(GGGGS)_3$, $(GGGGS)_n$ (n=1, 2, 4), $(Gly)_6$, $(Gly)_S$, AEAAAKEAAAKA, $A(EAAAK)_4ALEA(EAAAK)_4$ A, $(EAAAK)_3$, EAAAK, $(EAAAK)_2$, $(Ala-Pro)_n$ (n is 5 to 17, length from 10 to 34 aa), PAPAP, and may be a peptide linker consisting of an amino acid sequence selected from SEQ ID NO: 10, SEQ ID NO: 34, and SEQ ID NO: 53 to SEQ ID NO: 76.

In the present invention, the peptide linker may be suitably constructed by overlapping the above-exemplified peptide linkers or in combination with other linkers, if necessary.

For heterodimerization of Fc in the present invention, Fc heterodimerization techniques known in the art may be used. Fc heterodimerization technology is shown in Table 1 below.

TABLE 1

| strategy | CH3 domain 1 | CH3 domain 2 |
|---|---|---|
| knobs-into-holes (Y-T) | T366Y | Y407T |
| knobs-into-holes (CW-CSAV) | S354C, T366W | Y349C, T366S, L368A, Y407V |
| HA-TF | S364H, F405A | Y349T, T394F |
| ZW1 (VYAV-VLLW) | T350V, L351Y, F405A, Y407V | T350V, T366L, K392L, T394W |
| CH3 charge pairs (DD-KK) | K392D, K409D | E356K, D399K |
| IgG1 hinge/CH3 charge pairs (EEE-RRR) | IgG1: D221E, P228E, L368E | IgG1: D221R, P228R, K409R |
| IgG2 hinge/CH3 charge pairs (EEE-RRRR) | IgG2: C223E, P228E, L368E | IgG2: C223R, E225R, P228R, K409R |
| EW-RVT | K360E, K409W, | Q347R, D399V, F405T |
| EW-RVTS-S | K360E, K409W, Y349C | Q347R, D399V, F405T, S354C |
| Biclonic | 366K (+351K) | 351D or E or D at 349, 368, 349, or 349 + 355 |
| DuoBody (L-R) | F405L | K409R |
| SEEDbody | IgG/A chimera | IgG/A chimera |
| BEAT | residues from TCRα interface | residues from TCRβ interface |
| 7.8.60 (DMA-RRVV) | K360D, D399M, Y407A | E345R, Q347R, T366V, K409V |
| 20.8.34 (SYMV-GDQA) | Y349S, K370Y, T366M, K409V | E356G, E357D, S364Q, Y407A |

The present invention also provides a polypeptide comprising the amino acid sequence of SEQ ID NO: 4 or SEQ ID NO: 6, respectively or all of the polypeptide.

Also, the present invention provides
(a) a monomer comprising an interferon receptor 1 fragment and an antibody Fc fragment represented by the amino acid sequence of SEQ ID NO: 4;
(b) a dimeric polypeptide comprising a monomer comprising an interferon receptor 2 fragment and antibody Fc fragment represented by the amino acid sequence of SEQ ID NO: 6.

The monomer (a) comprises an interferon receptor 1 fragment and an antibody Fc fragment represented by the amino acid sequence of SEQ ID NO: 4, preferably, it may consist of or comprise an amino acid sequence selected from the group consisting of SEQ ID NO: 22, SEQ ID NO: 24, SEQ ID NO: 26, SEQ ID NO: 42, SEQ ID NO: 44 and SEQ ID NO: 46.

The monomer (b) comprises an interferon receptor 2 fragment and an antibody Fc fragment represented by the amino acid sequence of SEQ ID NO: 6, preferably, it may consist of or comprise an amino acid sequence selected from the group consisting of SEQ ID NO: 28, SEQ ID NO: 30, SEQ ID NO: 32, SEQ ID NO: 48, SEQ ID NO: 50 and SEQ ID NO: 52.

The polypeptide of the present invention may preferably be an antibody that mediates type 1 interferon.

The present invention also provides a polynucleotide encoding the polypeptide.

(i) In the present invention, 'polynucleotide' or 'nucleic acid' refers to deoxyribonucleic acid (DNA) or ribonucleic acid (RNA) in the form of single or double strands. Unless otherwise limited, known analogs of natural nucleotides that hybridize to nucleic acids in a manner analogous to naturally occurring nucleotides are also included.

A monomer comprising an interferon receptor 1 fragment and an antibody Fc fragment represented by the amino acid sequence of SEQ ID NO: 4, preferably, it may consist of or comprise a DNA sequence selected from the group consisting of SEQ ID NO: 21, SEQ ID NO: 23, SEQ ID NO: 25, SEQ ID NO: 41, SEQ ID NO: 43 and SEQ ID NO: 45.

A monomer comprising an interferon receptor 2 fragment and an antibody Fc fragment represented by the amino acid sequence of SEQ ID NO: 6, preferably, it may consist of or comprise a DNA sequence selected from the group consisting of SEQ ID NO: 27, SEQ ID NO: 29, SEQ ID NO: 31, SEQ ID NO: 47, SEQ ID NO: 49, and SEQ ID NO: 51.

The polynucleotide may be used without limitation as long as it encodes the polypeptide of the present invention, and includes all of DNA, cDNA and RNA sequences. It refers to a polynucleotide encoding a peptide having an amino acid sequence represented by the sequence or having an amino acid sequence having at least 70% homology with the amino acid sequence, it can be isolated from nature or prepared by genetic engineering methods known in the art.

The present invention also provides a vector comprising the polynucleotide.

The vector refers to an expression vector prepared by those skilled in the art to express the polypeptide of the present invention by inserting the polynucleotide of the present invention into the vector according to any method known in the art and using appropriate transcription/translation control sequences.

The polynucleotide sequence cloned according to the present invention may be operably linked to an appropriate expression control sequence, and the operably linked gene sequence and expression control sequence may be included in one expression vector including a selection marker and a replication origin. 'Operably linked' is meant that the polynucleotide sequence is linked to expression control sequences in such a way as to enable gene expression. The 'expression control sequence' refers to a DNA sequence that controls the expression of an operably linked polynucleotide sequence in a specific host cell. Such regulatory sequences may comprise one or more selected from the group consisting of a promoter for effecting transcription, an optional operator sequence for regulating transcription, sequences encoding suitable mRNA liposome binding sites, and sequences controlling the termination of transcription and translation and the like.

The vector used as the parent vector of the expression vector is not particularly limited, all plasmids, viruses or other mediators commonly used for expression in microorganisms used as host cells in the art to which the present invention pertains can be used. For example, the plasmid includes *E. coli*-derived plasmids (pBR322, pBR325, pUC118 and pUC119, pET-22b(+)), *Bacillus subtilis*-derived plasmids (pUB110 and pTP5) and yeast-derived plasmids (YEp13, YEp24 and YCp50) and the like, the virus may be used by an animal virus such as retrovirus, adenovirus or vaccinia virus, insect viruses such as baculoviruses and the like, but is not limited thereto.

The present invention also provides a host cell transformed with the vector.

The host cell may choose to modulate the expression of the inserted sequence or to process the gene product in the particular manner desired. Different host cells have characteristic and specific mechanisms for translation and post-translational processing and modification of proteins. Suitable cell lines or host systems can be selected that provide for the desired modification and processing of the expressed heterologous protein. Expression in yeast can produce biologically active products. Expression in eukaryotic cells may increase the likelihood of "native" folding.

As a host cell capable of stably and continuously cloning and expressing the vector of the present invention may be used in any host cell known in the art, for example, *E. coli* JM109, *E. coli* BL21DE, *E. coli* DH5, *E. coli* RR1, *E. coli* LE392, *E. coli* B, *E. coli* X 1776, *E. coli* W3110 and the like may be used, in addition, strains of the genus *Agrobacterium*, such as *Agrobacterium* A4, Bacilli, such as *Bacillus subtilis*, another intestinal Bacteria and various strains of the genus *Pseudomonas* such as *Salmonella typhimurium*, or *Serratia marcescens* can be used as host cells.

In addition, when the vector of the present invention is transfected into eukaryotic cells, as host cells, yeast (*Saccharomyces cerevisiae*), insect cells and human cells (eg, CHO cell lines (Chinese hamster ovary), Expi293, W138, BHK, COS-7, 293, HepG2, 3T3, RIN and MDCK cell lines) and the like can be used.

In the present invention, the host cell may preferably be Expi293 or CHO cell line.

The method for transfecting the host cell by delivering the vector into the host cell may be any known method and is not particularly limited. For example, transfection can be performed by gene bombardment, polycation, and receptor-mediated transfection using calcium phosphate precipitation, DEAE-dextran method, electroporation method, direct microinjection method, DNA-loaded liposome method, lipofectamine-DNA complex method, cell sonication method (cell sonication), high velocity microprojectile. Some of these techniques can be improved for in vivo or ex vivo use.

The present invention also provides a method for producing a dimeric polypeptide comprising the step of (a) providing a host cell, (b) culturing the provided cell, and (c) preparing the polypeptide of the present invention by recovering the polypeptide from the cell or culture medium.

Culturing of the transformed cells is carried out under appropriate conditions allowing expression of the fusion protein (or fusion polypeptide), these conditions can be carried out according to methods well known to those skilled in the art. Transformed cells can be cultured in large quantities by conventional culture methods. As the culture medium, a medium composed of a carbon source, a nitrogen source, vitamins and minerals may be used, for example, 2XYT medium may be used. Cell culture is possible under normal cell culture conditions, for example, it can be cultured for 10 hours to 40 hours at a temperature range of 15° C. to 45° C. In order to remove the cells in the culture medium and recover only the culture medium, centrifugation or filtration may be performed. These steps can be performed by those skilled in the art as needed. The culture medium (filtrate) from which the cells have been removed can be refrigerated according to a conventional method and stored for a short time so as not to lose its activity.

The fusion protein expressed in the transformed cell (or transformant) may be purified in a conventional manner, for example, the fusion protein of the present invention may be purified by applying techniques such as salting out (e.g., ammonium sulfate precipitation, sodium phosphate precipitation), column chromatography and ultrafiltration such as solvent precipitation (precipitation of protein fraction using acetone, ethanol, etc.), dialysis, gel filtration, ion exchange, reverse phase column chromatography, affinity chromatography alone or in combination.

The interferon receptor of the present invention is a hyper-glycosylated protein containing a large amount of glycosylation during post-translational modification, and microbial culture may not be suitable because the corresponding sugar causes structural stability problems. Accordingly, the polypeptide of the present invention may preferably be a host cell of an animal cell.

Accordingly, the present invention provides a pharmaceutical composition for preventing or treating a type 1 interferon-mediated disease or disorder comprising a polypeptide as an active ingredient.

"Type 1 interferon-mediated disease or disorder" according to the present invention refers to a disease or disorder mediated by type 1 interferon or a disease associated with abnormal expression (e.g., overexpression or inhibition of expression) of an interferon-inducible gene, examples include, but are not limited to, systemic lupus erythematosus (SLE, J Immunol. 2014 Jun. 15; 192(12): 5459-5468.) Sjogren's Syndrome (Autoimmun Rev. 2013 March; 12(5): 558-66.), Insulin Dependent Diabetes Mellitus (IDDM), Inflammatory Bowel Disease (IBD) (including Crohn's Disease, Ulcerative Colitis and Celiac Disease), Multiple Sclerosis (MS), psoriasis, autoimmune thyroiditis, rheumatoid arthritis (RA, Front Immunol. 2017; 8: 2007.), inflammatory myositis (Arthritis Rheum 2009; 60:181524.; Mol Med 2007; 13:5968.) and glomerulonephritis. Moreover, the composition of the present invention can be used for the inhibition or prevention of transplant rejection or for the treatment of graft-versus-host reaction (GVHD) or for the treatment of HIV infection/AIDS.

Meanwhile, the pharmaceutical composition according to the present invention may be provided by formulating the polypeptide in a pure form or in a suitable form together with a pharmaceutically acceptable carrier. 'Pharmaceutically acceptable' refers to a non-toxic composition that is physiologically acceptable and does not normally cause allergic reactions such as gastrointestinal disorders, dizziness, or similar reactions when administered to humans. The carrier includes all kinds of solvents, dispersion media, oil-in-water or water-in-oil emulsions, aqueous compositions, liposomes, microbeads and microsomes.

Meanwhile, the pharmaceutical composition according to the present invention may be formulated with a suitable carrier depending on the route of administration. The route of administration of the pharmaceutical composition according to the present invention is not limited thereto, but may be administered orally or parenterally. Parenteral routes of administration include multiple routes such as, for example, transdermal, nasal, intraperitoneal, intramuscular, subcutaneous, or intravenous.

When the pharmaceutical composition of the present invention is orally administered, the pharmaceutical composition of the present invention may be formulated in the form of powder, granules, tablets, pills, dragees, capsules, liquids, gels, syrups, suspensions, wafers and the like according to a method known in the art together with a suitable carrier for oral administration. Examples of suitable carriers may be included in sugars including lactose, dextrose, sucrose, sorbitol, mannitol, xylitol, erythritol and maltitol and the like, and starches including corn starch, wheat starch, rice starch and potato starch and the like, celluloses including cellulose, methyl cellulose, sodium carboxymethylcellulose and hydroxypropylmethyl-cellulose and the like, and the like, fillers such as gelatin, polyvinylpyrrolidone, and the like. In addition, cross-linked polyvinylpyrrolidone, agar, alginic acid or sodium alginate may be added as a disintegrant if necessary. Furthermore, the pharmaceutical composition may further include an anti-aggregating agent, a lubricant, a wetting agent, a flavoring agent, an emulsifying agent, and a preservative and the like.

In addition, when administered parenterally, the pharmaceutical composition of the present invention may be formulated according to methods known in the art in the form of injections, transdermal administrations and nasal inhalants together with suitable parenteral carriers. In the case of the injection, it must be sterilized and protected from contamination of microorganisms such as bacteria and fungi. For injection, examples of suitable carriers may include, but are not limited to, water, ethanol, polyol (e.g., glycerol, propylene glycol and liquid polyethylene glycol, etc.), mixtures thereof and/or a solvent or dispersion medium containing vegetable oil. More preferably, as a suitable carrier, Hanks' solution, Ringer's solution, an isotonic solution such as phosphate buffered saline (PBS) or sterile water for injection, 10% ethanol, 40% propylene glycol and 5% dextrose with triethanolamine, and the like can be used. In order to protect the injection from microbial contamination, it may further include various antibacterial and antifungal agents such as parabens, chlorobutanol, phenol, sorbic acid, thimerosal, and the like. In addition, in most cases, the injection may further contain an isotonic agent such as sugar or sodium chloride.

In the case of transdermal administration, forms such as ointment, cream, lotion, gel, external solution, pasta, liniment, and air are included. As used herein, "transdermal administration" means that an effective amount of the active ingredient contained in the pharmaceutical composition is delivered into the skin by topically administering the pharmaceutical composition to the skin. These formulations are described in formularies commonly known in pharmaceutical chemistry.

For administration by inhalation, the compounds for use according to the invention may be conveniently delivered in the form of an aerosol spray from a pressurized pack or nebulizer using a suitable propellant, for example dichlorofluoromethane, trichlorofluoromethane, dichlorotetrafluoroethane, carbon dioxide or other suitable gas. In the case of a pressurized aerosol, the dosage unit may be determined by providing a valve to deliver a metered amount. For example, gelatin capsules and cartridges used in inhalers or insufflators may be formulated to contain a powder mixture of the compound and a suitable powder base such as lactose or starch. As other pharmaceutically acceptable carriers, those known in the art may be referred to.

In addition, the pharmaceutical composition according to the present invention may further comprise one or more buffers (e.g., saline or PBS), Carbohydrate (e.g., glucose, mannose, sucrose or dextran), stabilizer (sodium bisulfite, sodium sulfite or ascorbic acid) antioxidant, bacteriostatic, chelating agent (e.g., EDTA or glutathione), adjuvants (e.g., aluminum hydroxide), suspending agents, thickening agents and/or preservatives (benzalkonium chloride, methyl- or propyl-paraben and chlorobutanol).

In addition, the pharmaceutical compositions of the present invention may be formulated using methods known in the art to provide rapid, sustained or delayed release of the active ingredient after administration to a mammal.

The pharmaceutical composition formulated in the above manner may be administered in an effective amount through various routes including oral, transdermal, subcutaneous, intravenous or intramuscular. As used herein, the term 'effective amount' refers to an amount of a compound or extract that enables tracking of diagnostic or therapeutic effects when administered to a patient. The dosage of the pharmaceutical composition according to the present invention may be appropriately selected according to the route of administration, the administration target, the target disease and its severity, age, sex, body weight, individual differences and disease state. Preferably, the pharmaceutical composition comprising the polypeptide of the present invention may vary the content of the active ingredient depending on the severity of the disease, but, in general, based on an adult, it may be repeatedly administered several times a day at an effective dose of 10 μg to 10 mg when administered once.

In addition, the present invention provides a vaccine comprising a polypeptide as an active ingredient, and the vaccine according to the present invention is a vaccine for preventing or treating a type 1 interferon-mediated disease or disorder.

As used herein, the term "vaccine" refers to an immunogen or antigenic substance that induces immunity in a living body by injecting or orally administering to a person or animal for the prevention of infection as a biological agent containing an antigen that gives immunity to a living body. In vivo immunity is largely divided into automatic immunity, which is obtained automatically after infection with a pathogen, and passive immunity, which is obtained by an externally injected vaccine. While autoimmunity is characterized by a long period of production of antibodies related to immunity and continuous immunity, passive immunity by vaccine works immediately for the treatment of infection, but has the disadvantage of poor durability.

The vaccine composition of the present invention may include a pharmaceutically acceptable carrier. It refers to any component suitable for delivery of an antigenic material to a site in vivo, examples include, but are not limited to, water, saline, phosphate buffered saline, Ringer's solution, dextrose solution, serum-containing solution, Hans' solution, other aqueous physiologically equilibrated solutions, oils, esters and glycols, and the like.

The carrier of the present invention may contain suitable auxiliary ingredients and preservatives to enhance chemical stability and isotonicity, stabilizers such as trehalose, glycine, sorbitol, lactose or monosodium glutamate (MSG) may be included to protect the vaccine composition against temperature changes or lyophilization. The vaccine composition of the present invention may contain a suspension liquid such as sterile water or saline (preferably buffered saline).

The vaccine composition of the present invention may contain any adjuvant in an amount sufficient to enhance the immune response to the immunogen. Suitable adjuvants are known in the art, examples include, but are not limited to, aluminum salts (aluminum phosphate or aluminum hydroxide), Squalene mixture (SAF-1), muramyl peptide, saponin derivative, *mycobacterium* cell wall preparation, monophosphoryl lipid A, mycolic acid derivative, Nonionic block copolymer surfactants, Quil A, cholera toxin B subunit, polyphosphazene and derivatives, and immun-stimulating complexes (ISCOMs).

As with all other vaccine compositions, the immunologically effective amount of the immunogen must be determined empirically, in which case factors that may be considered include immunogenicity, route of administration, and frequency of administration of the immune system. In addition, it can be adjusted according to the patient's disease progression and metastasis status, the type of formulation, the patient's age, sex, weight, health status, diet, administration time, and administration method.

The dimeric polypeptide in the vaccine composition of the present invention may be present in various concentrations in the composition of the present invention, but, typically, the antigen material is included in a concentration necessary to induce the formation of an appropriate level of antibody in vivo.

As used herein, the term "administration" means introducing a predetermined substance into a patient by any suitable method, and the administration route of the vaccine of the present invention may be administered through any general route as long as they can reach the target tissue.

The vaccine composition of the present invention can be used to treat type 1 interferon-mediated diseases or disorders by administration via the systemic or mucosal route.

Administration of the vaccine composition may include, but is not limited to, injection via an intramuscular, intraperitoneal, intradermal or subcutaneous route, oral/meal, respiratory, and mucosal administration to the genitourinary tract.

In addition, in order to increase the efficacy of the vaccine, when the vaccine is injected, cytokines that help activate T cells, such as IL-12, are co-administered, or a vaccine transfected with these cytokine genes may be used.

Cells containing the dimer-type polypeptide, which is an active ingredient of the vaccine produced by the present invention, can also be depleted of cell proliferation in order to increase safety, because the human body is inoculated as a therapeutic vaccine. For example, in order to be selectively used as a cell vaccine more safely, it can be treated with heat treatment, radiation treatment, or mitomycin C (MMC) treatment, and the proliferation can be eliminated, while leaving the function as a vaccine. For example, when using X-ray irradiation, it can be irradiated with a total radiation dose of 1000 to 3300 Rad. In the mitomycin C treatment method, for example, 25 to 50 μg/ml of mitomycin C is added to the polypeptide, and heat treatment can be performed at 37° C. for 30 minutes to 60 minutes. In the cell treatment method by heat, for example, heat treatment can be performed at 50° C. to 65° C. for 20 minutes.

As used herein, 'treatment' refers to a clinical procedure intended to alter the natural process of a subject or cell to be treated, it can also be performed for the prevention of clinical pathology. Desirable effects of treatment include suppression of occurrence or recurrence of disease, alleviation of symptoms, reduction of any direct or indirect pathological consequences of disease, reducing the rate of disease progression, ameliorating, improving, alleviating, or improving prognosis and the like. Also, the term 'prevention' refers to any action that suppresses the onset or delays the progression of a disease.

As used herein, the term 'comprising' is used with the same meaning as 'including' or 'characterized by', in the composition or method according to the present invention, additional components or steps of the method not specifically mentioned are not excluded. In addition, the term 'consisting of' means excluding additional elements, steps, or ingredients that are not separately described. The term 'essentially consisting of' means that, in the scope of the composition or method, it may include substances or steps that do not substantially affect the basic properties thereof in addition to the substances or steps described.

The present invention also provides a use of the polypeptide for the preparation of an agent for preventing or treating a type 1 interferon-mediated disease or disorder.

In addition, the present invention provides a method for treating a type 1 interferon-mediated disease or disorder, comprising administering to a subject in need thereof an effective amount of a composition comprising the polypeptide as an active ingredient.

The 'effective amount' of the present invention refers to an amount that, when administered to an individual, exhibits an effect of improving, treating, preventing, detecting, diagnosing, or inhibiting or reducing a type 1 interferon-mediated disease or disorder, or a type 1 interferon-mediated disease or disorder, and the 'subject' may be an animal, preferably an animal, including a mammal, particularly a human, and a cell, tissue, organ, or the like derived from an animal. The subject may be a patient in need of the effect.

The 'treatment' of the present invention refers generically to ameliorating a type 1 interferon mediated disease or disorder, or a symptom of a type 1 interferon mediated disease or disorder, and this may include curing, substantially preventing, or ameliorating the condition, and including alleviating, curing or preventing one or most of the symptoms resulting from the disease, but is not limited thereto.

Advantageous Effect

The type 1 interferon-neutralizing Fc-fusion protein of the present invention blocks the binding of type 1 interferon to the interferon receptor, and has excellent initiation and biological activity inhibition of signaling mechanisms, thereby effectively treating diseases mediated by type 1 interferon.

BRIEF DESCRIPTION OF THE DRAWINGS

FIG. 1 shows a schematic diagram of the preparation of an expression vector for the production of type 1 interferon Fc fusion receptor protein. SEQ ID NO: 10 and 34.

FIG. 2*a* is a result of comparing the size of each protein through size exclusion chromatography.

FIG. 2*b* is a result confirming the binding of IFNAR1/2 hetero Fc fusion protein and human IFN 13 under native conditions and reducing conditions.

FIG. 2*c* is a schematic diagram showing the type 1 interferon Fc fusion receptor protein.

FIG. 3 is a diagram showing the results of SPR analysis of the type 1 interferon Fc fusion receptor protein.

FIGS. 4*a* to 4*c* are results confirming the type 1 interferon neutralizing ability of the type 1 interferon Fc fusion receptor protein of the present invention.

FIG. 4a is a result showing the cell viability in Daudi cells treated with human IFN β-1a alone or type 1 interferon Fc fusion receptor protein.

Figure 5:
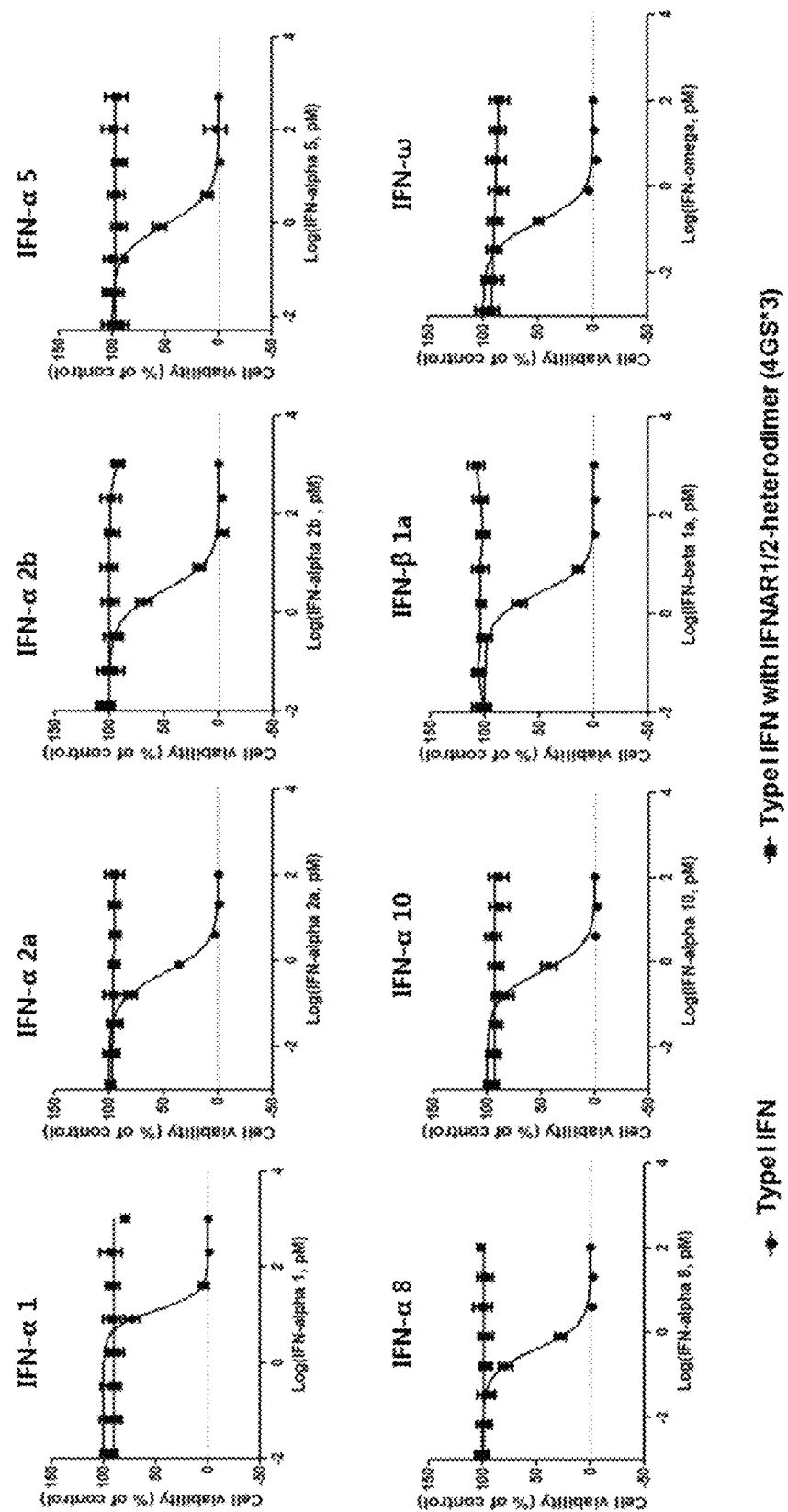

FIG. 5 confirms the neutralizing ability of the IFNAR1/2-Fc heterodimer (4GS*3) protein of the present invention for the biological activity of type 1 interferon (IFN-α 1, IFN-α 2a, IFN-α 2b, IFN-α 5, IFN-α 8, IFN-α 10, IFN-β 1a, IFN-ω), and the cell viability of Daudi cells in the group to which type 1 interferon was added and the group in which each interferon was treated with IFNAR1/2-Fc heterodimer (4GS*3) protein was shown.

Figure 6A:
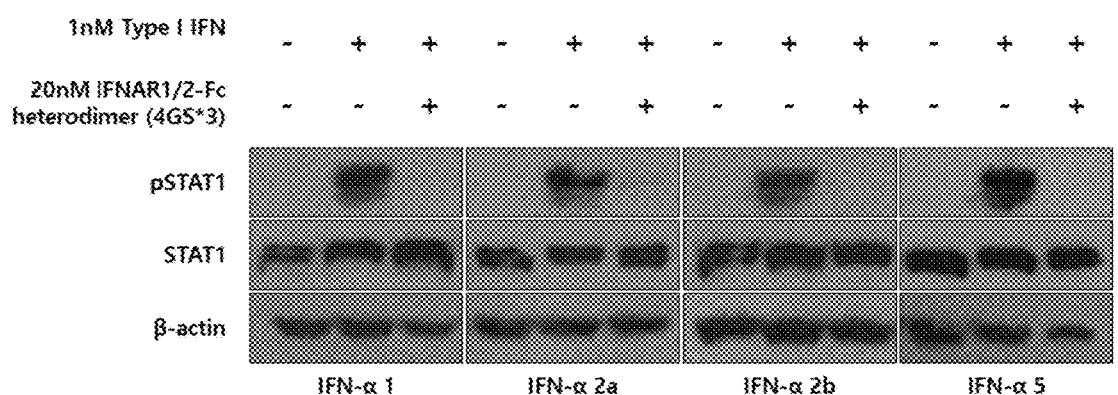
Figure 6B:
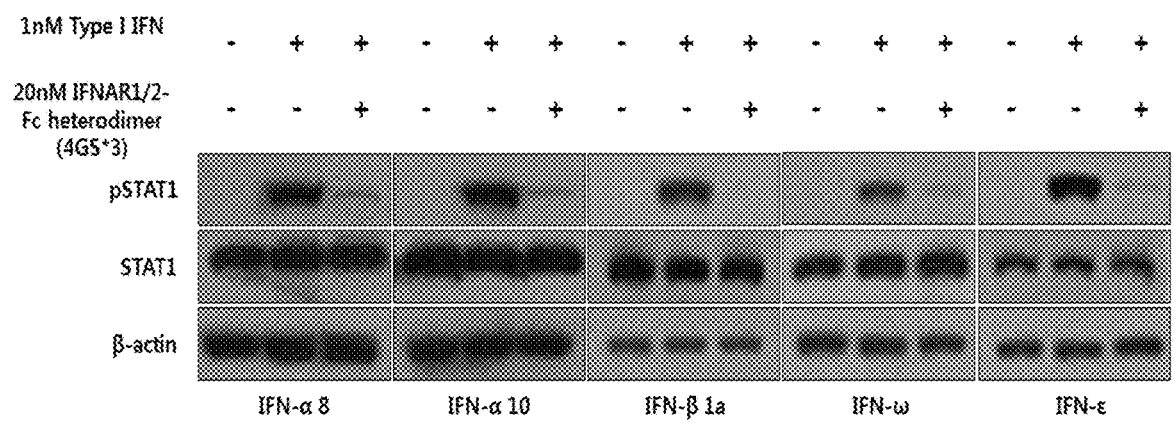

FIGS. 6a and 6b are the results of confirming the neutralizing ability of the IFNAR1/2-Fc heterodimer (4GS*3) protein of the present invention for the signaling mechanism of type 1 interferon, and the results show the phosphorylation change of STAT1 protein in Daudi cells of the group to which type 1 interferon (IFN-α 1, IFN-α 2a, IFN-α 2b, IFN-α 5, IFN-α 8, IFN-α 10, IFN-β 1a, IFN-ω, IFN-ε) was added and the group in which each interferon was treated with IFNAR1/2-Fc heterodimer (4GS*3) protein.

MODE FOR CARRYING OUT INVENTION

Hereinafter, the present invention will be described in detail.

However, the following examples are only illustrative of the present invention, and the content of the present invention is not limited to the following examples.

Figure 1:
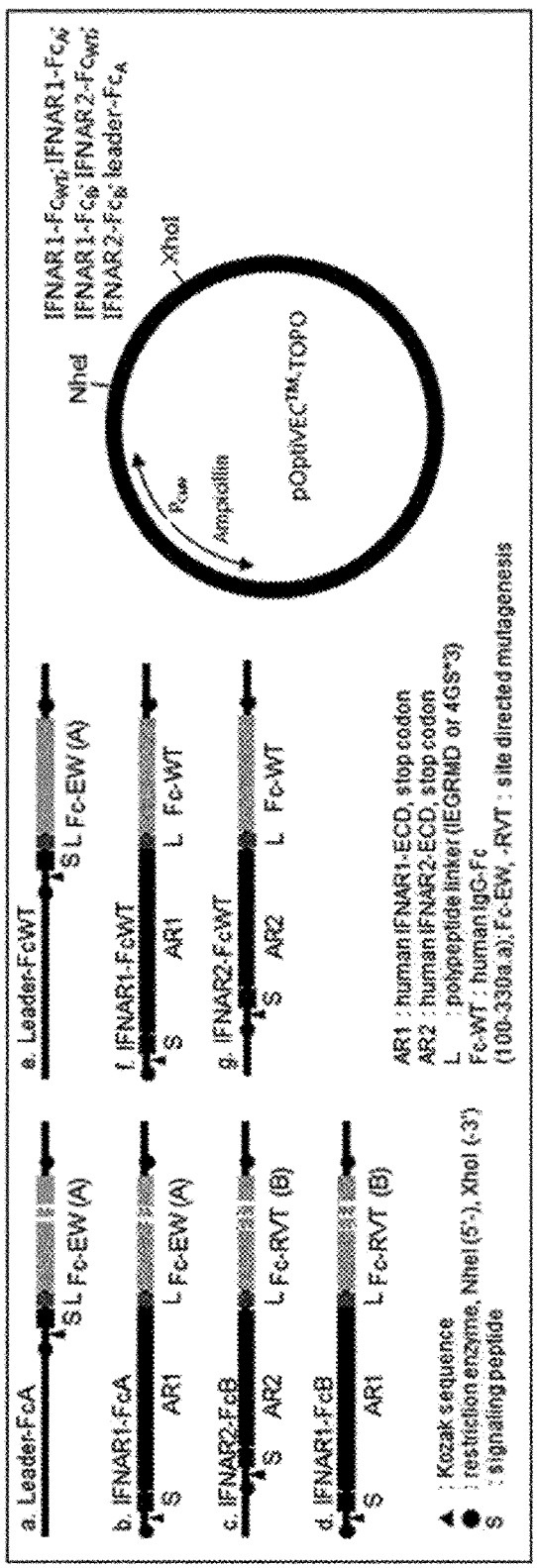
Figure 2A:
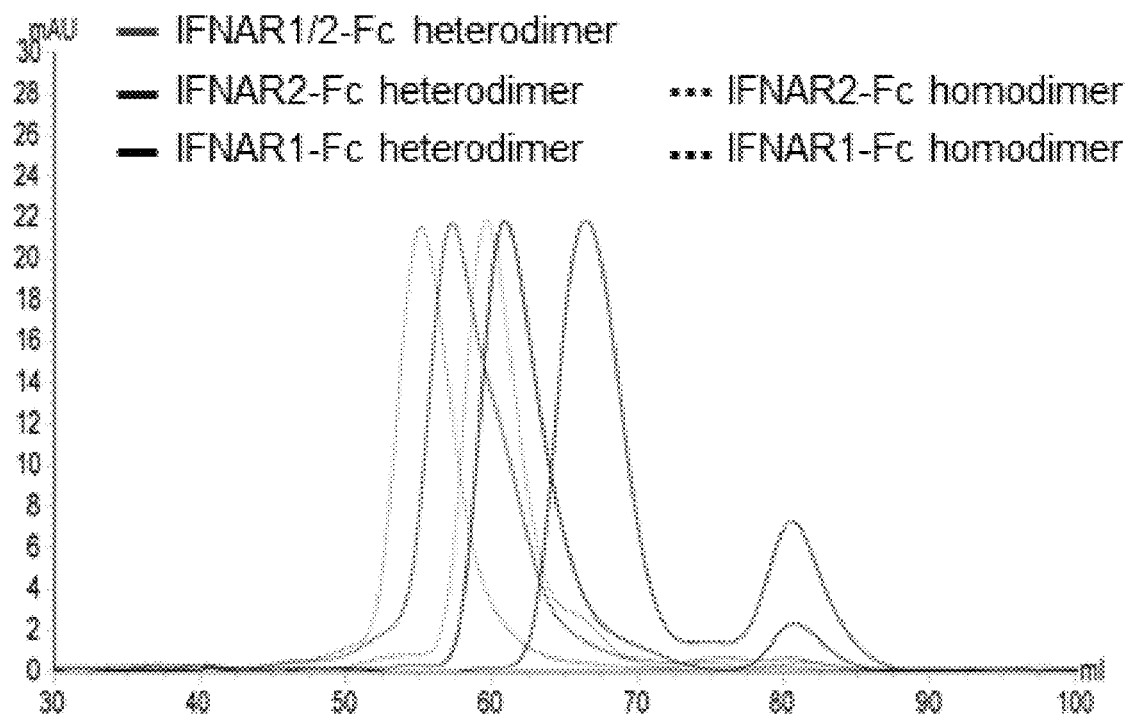
Figure 2B:
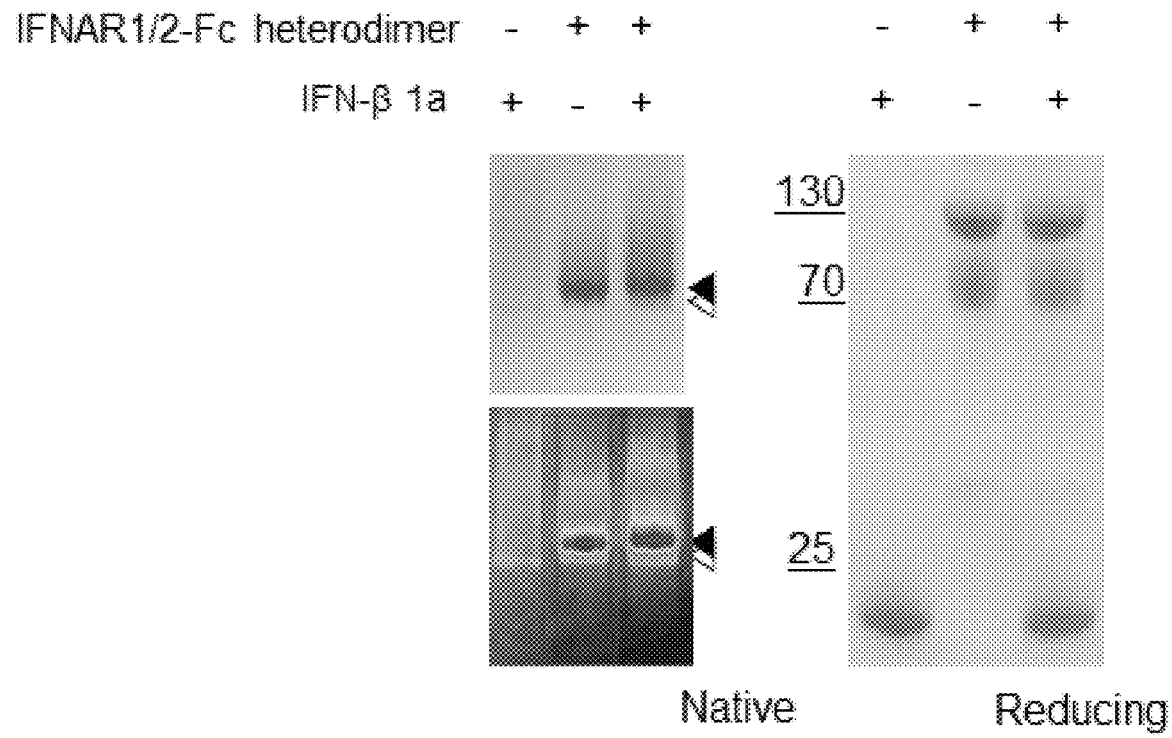
Figure 2C:
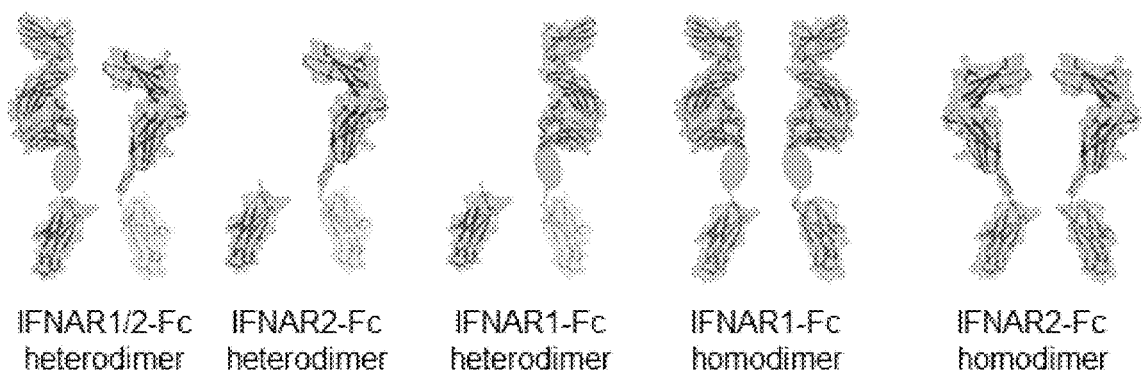

Example 1: Preparation of Expression Vector for Production of Type 1 Interferon Fc Fusion Receptor Protein Human IFNAR1 (P17181, 28-436 aa.), IFNAR2 (P48552, 27-243 aa.) and IGHG (P01857, 100-330 aa) amino acid sequences were used to develop an Fc fusion protein capable of binding or neutralizing type 1 interferon protein. As shown in FIG. 1 (left), Fc were labeled with a polypeptide linker (L; IEGRMD) at the C-terminus of the expression vector in all Fc fusion protein expression vectors, it is linked by IFNAR1 or IFNAR2 between the C-terminus and the N-terminus including the Kozac sequence (▲) and the extracellular secretion inducing signal sequence (S), or directly linked.

As shown in FIG. 1 (right), the sequence including each gene was linked between restriction enzymes NheI and XhoI. Expression vectors were named pIFNAR1-FcWT, pIFNAR2-FcWT, pIFNAR1-FcA, pIFNAR2-FcB, pIFNAR1-FcB and pLeader-FcA, respectively.

Codon optimization of the gene comprising the polynucleotide sequence (SEQ ID NO: 1), the extracellular domain of IFNAR1 (SEQ ID NO: 3), the extracellular domain of IFNAR2 (SEQ ID NO: 5), a polypeptide linker (SEQ ID NO: 7), and the Fc portion of human IGHG (SEQ ID NO: 11) and variants (SEQ ID NO: 13, SEQ ID NO: 15) comprising the Kozac sequence and the signal sequence was performed to synthesize the gene to prepare the nucleotide sequence fragments e to g of FIG. 1. An expression vector was prepared using T4 DNA ligase (RBC) between NheI and Xho I among the restriction enzyme sites of the expression vector (pOptiVec-TOPO) for each nucleotide sequence fragment.

In addition, the expression vector was prepared in the same manner except that the linker of SEQ ID NO: 33 was used instead of the polypeptide linker of SEQ ID NO: 7. In other words, the gene comprising the polynucleotide sequence (SEQ ID NO: 1), the extracellular domain of IFNAR1 (SEQ ID NO: 3), the extracellular domain of IFNAR2 (SEQ ID NO: 5), a polypeptide linker (SEQ ID NO: 33), and the Fc portion of human IGHG (SEQ ID NO: 11) and variants (SEQ ID NO: 13, SEQ ID NO: 13) number 15) comprising the Kozac sequence and the signal sequence was codon-optimized to synthesize the gene to prepare the nucleotide sequence fragments e to g of FIG. 1. An expression vector was prepared using T4 DNA ligase (RBC) between NheI and Xho I among the restriction enzyme sites of the expression vector (pOptiVec-TOPO) for each nucleotide sequence fragment.

Example 2: Protein Expression Purification, Structure Confirmation and Binding Confirmation The following expression and purification processes were performed in order to produce a protein having the structure shown in FIG. 2c using expression vectors into which the nucleotide sequence fragments of each combination were inserted.

In order to maintain the native post-translational modification (PTM) of each type 1 interferon receptor, all recombinant protein expression use Expi293TM expression medium in 300-600 mL according to the protocol of the transient expression system, using the human-derived expression cell, Expi293 cell line (Thermo Fisher Scientific). Depending on the final protein, one or two expression vectors were transfected into cells, and then Enhancers 1 and 2 were added according to the manufacturer's protocol. Thereafter, the culture medium cultured for 6 days was centrifuged at 6580 rpm, 20 minutes, and 8° C., and then filtered using a 0.22 μm polytyrene filter (Corning). All proteins were purified in the AKTA avant purification system (GE healthcare Life Sciences), and the column filled with MabSelect SuRe (GE healthcare Life Science) was equilibrated as much as 2 CV using 20 mM sodium phosphate, pH 7.2 and 150 mM NaCl buffer at a rate of 5 ml/min, and then the culture solution was flowed to bind to the resin.

Thereafter, the recombinant protein was eluted with 100 mM citrate buffer, pH 3.5 buffer after a column wash process using 5 CV of 35 mM sodium phosphate, pH 7.2, 500 mM NaCl buffer and 1 CV of 20 mM sodium phosphate, pH 7.2 buffer. The eluted protein was concentrated to 3 ml using an Amicon Ultra Centrifugal filter (50K-cut off, Merck Millipore) after dialysis for 12 hours and 3 times using 4L of 1×PBS buffer (Biosesang). The concentrated recombinant protein was additionally separated from the target protein using the same buffer used for dialysis on a Hiload Superdex 200 pg (GE healthcare Life Sciences) column.

As a result, as shown in FIG. 2a, the size of each Fc fusion protein was compared through size exclusion chromatography, and it was expected to have the protein structure shown in FIG. 2c.

In addition, as shown in FIG. 2b, binding between the IFNAR1/2 hetero Fc fusion protein and human IFN β-1a was confirmed, respectively in native conditions (7.5% Mini-PROTEIN® TGXTM Precase protein gels), reducing conditions (Any kDTM Mini-PROTEIN® TGXTM Precast protein gel, Bio-rad)

The FC portion of the amino acid sequence of the present invention includes the HINGE portion of IGHG1 (100-330a.a.), and a disulfide bond is formed by amino acids 109-109 and 112-112 to form a dimer. In more detail, the formation of a heterodimer occurs dominantly from a homodimer to a heterodimer due to a change in the specific amino acid sequence of the CH3 portion of FC.

Example 3: SPR Analysis Using Fc Fusion Protein

Binding affinity and kinetics of Fc fusion proteins (IFNAR2-Fc heterodimer, IFNAR1/2-Fc heterodimer, IFNAR1-Fc heterodimer) expressed/purified through the expression vector combination of FIG. 1 and hIFN β-1a among Type I IFNs were analyzed.

In this experiment, (IFNAR1-Fc EW+-Fc RVT), (IFNAR2-Fc EW+-Fc RVT) and (IFNAR1-Fc EW+IFNAR2Fc RVT) were used to analyze binding strength and kinetics. When expressing (IFNAR1-Fc RVT+IFNAR2-Fc EW), as it was confirmed that the problem that the homodimer form appeared more than (IFNAR1-Fc EW+IFNAR2-Fc RVT) was confirmed, so (IFNAR1-Fc RVT+IFNAR2-Fc EW) was not used.

Based on Biacore T200 (GE Healthcare Life Sciences), 25° C., 30 µl/min conditions and 0.005% DPBST (DPBS/modified, Hyclone and Tween20, Signal) running buffer were used, and the gold sensor chip was amine-coupled with an anti-human Fcγ capture antibody (AffiniPure Goat Anti-Human IgG, Fcγ fragment specific, Jackson ImmunoResearch). Each analyte was tested under 180 seconds, association and 600 seconds, and dissociation conditions.

Figure 3:
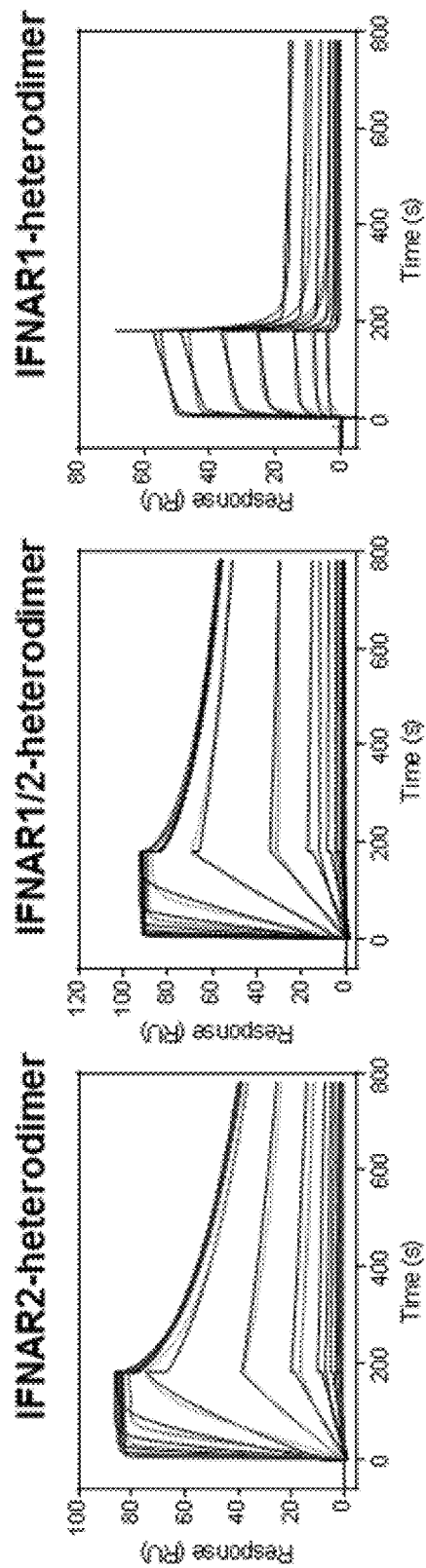

As shown in FIG. 3, the curve fitting was performed according to hIFNb-1a-IFNAR2 (1:1 fitting model), hIFNb-1a-IFNAR1/2 (heterogeneous ligand model), hIFNb-1a-IFNAR1 (two-state binding models) sensorgram shape and the docking model prediction. In particular, the IFNAR1/2 hetero Fc fusion protein showed a low KD value. (See Table 2 and Table 3)

TABLE 2

| Ligand | Analyte | $k_{1a} \times 10^5$ ($M^{-1} s^{-1}$) | $k_{1d} \times 10^{-3}$ ($s^{-1}$) | $K_{1D}$ (nM) | $k_{2a} \times 10^7$ ($M^{-1} s^{-1}$) | $k_{2d} \times 10^{-3}$ ($s^{-1}$) | $K_{2D}$ (pM) |
|---|---|---|---|---|---|---|---|
| IFNAR2-Fc heterodimer | IFN-β-1a[a] | 75.45 | 3.556 | 0.47 | | | |
| | IFN-β-1a[b] | | | 4.26 | | | |
| IFNAR1/2-Fc heterodimer | IFN-β-1a[c] | 76.85 | 0.0044 | 0.0006 | 1.57 | 3.109 | 198.6 |
| | IFN-β-1a[b] | | | 4.775 | | | |
| IFNAR1-Fc heterodimer | IFN-β-1a[a] | 0.2368 | 0.9723 | 41.11 | | | |
| | IFN-β-1a[b] | | | 81.51 | | | |

[a]Sensorgrams fit with one to one binding model (A + B ⇌ AB)
[b]the steady state equilibrium analysis were estimated using each parameter at 179.04 sec.
[c]Sensorgrams fit with heterogeneous ligand model (A + B ⇌ AB + C ⇌ ABC)

TABLE 3

| Ligand | Analyte | $k_{1a} \times 10^5$ ($M^{-1} s^{-1}$) | $k_{1d} \times 10^{-3}$ ($s^{-1}$) | $k_{2a} \times 10^{-3}$ ($s^{-1}$) | $k_{2d} \times 10^{-3}$ ($s^{-1}$) | $K_{2D}$ (nM) |
|---|---|---|---|---|---|---|
| IFNAR1-Fc heterodimer | IFN-β-1a[a] | 5.426 | 129.7 | 1.776 | 45.75 | 48.97 |
| IFNAR2-Fc heterodimer | IFN-β-1a[a] | 2.23E+06 | 8.81E+05 | 22.04 | 3.444 | 0.5342 |

[a]Sensorgrams fit with two-state binding model (A + B ⇌ AB ⇌ AB*)

Example 4: Confirmation of Biological Activity Neutralizing Ability by Ligand of Fc Fusion Protein The following experiment was conducted to confirm the neutralizing ability of the Fc fusion protein to the biological activity caused by the ligand. As in Example 3, (IFNAR1-Fc EW+-Fc RVT), (IFNAR2-Fc EW+-Fc RVT) and (IFNAR1-Fc EW+IFNAR2Fc RVT) were used in this experiment.

All experiments were designed based on the anti-proliferative effect of hIFN-β using the Ez-cytox cell viability assay kit (Deaillab) in Daudi cells, where the expression of each receptor is high. This test method showed test results that well reflect the biophysical characteristics of the ligand, similar to the results of the kinetics analysis of SPR.

Specifically, in a 96-well plate (SPL), the concentration of hIFN-β-1a in cells of $3 \times 10^3$ cells was determined by concentration (10 nM of IFNAR1-Fc heterodimer, IFNAR2-Fc heterodimer, IFNAR1/2-Fc heterodimer; 6 pM of IFNAR1-Fc heterodimer; IFNAR1/2-Fc heterodimer), and then the reaction was carried out in a cell incubator at 37° C. and 5% $CO_2$ for 72 hours. Then, after adding the Ex-cytox reagent according to the manufacturer's protocol, after an additional 3 hours of reaction, it was measured at 450 nm with a Microplate reader (Genios Pro, Tecan), and $IC_{50}$ values were compared and analyzed using nonlinear regression analysis (GraphPad Prism version 7.0 software, san diego, Ca, USA). The neutralizing ability of each protein of the present invention was confirmed for statistical significance through One-way ANOVA, Bonferroni's multiple comparisons post hoc test.

Figure 4A:
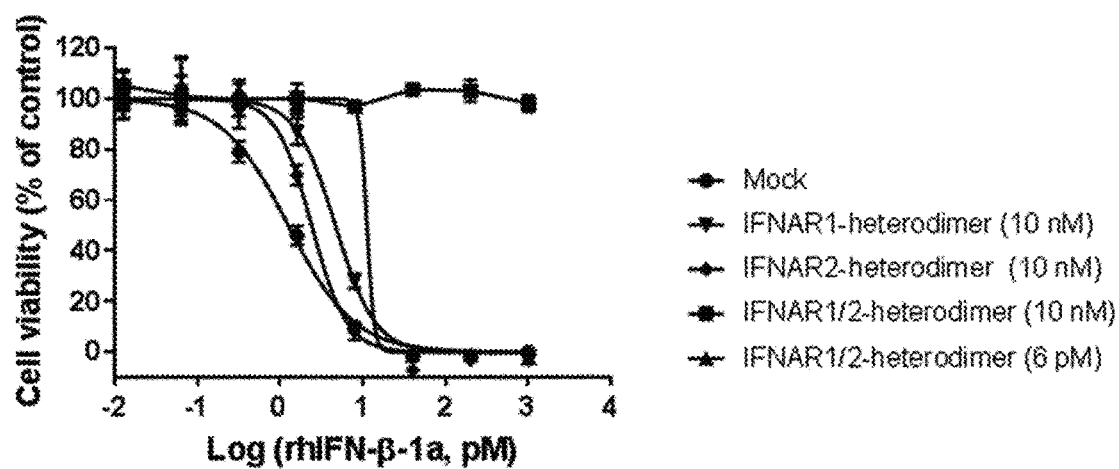
FIG. 4b is a result showing the IC50 value treated with human IFN β-1a alone or type 1 interferon Fc fusion receptor protein.
FIG. 4c is a result showing the cell viability of Daudi cells treated with human IFN β-1a according to the concentration of the protein of the present invention.

As shown in FIG. 4a, it was confirmed that anti-cell proliferation by interferon was significantly reduced as compared to the case of a fusion protein that blocks IFNAR1 and IFNAR2, respectively, when interferon is treated with an Fc fusion protein that blocks both IFNAR1 and IFNAR2 binding.

Figure 4B:
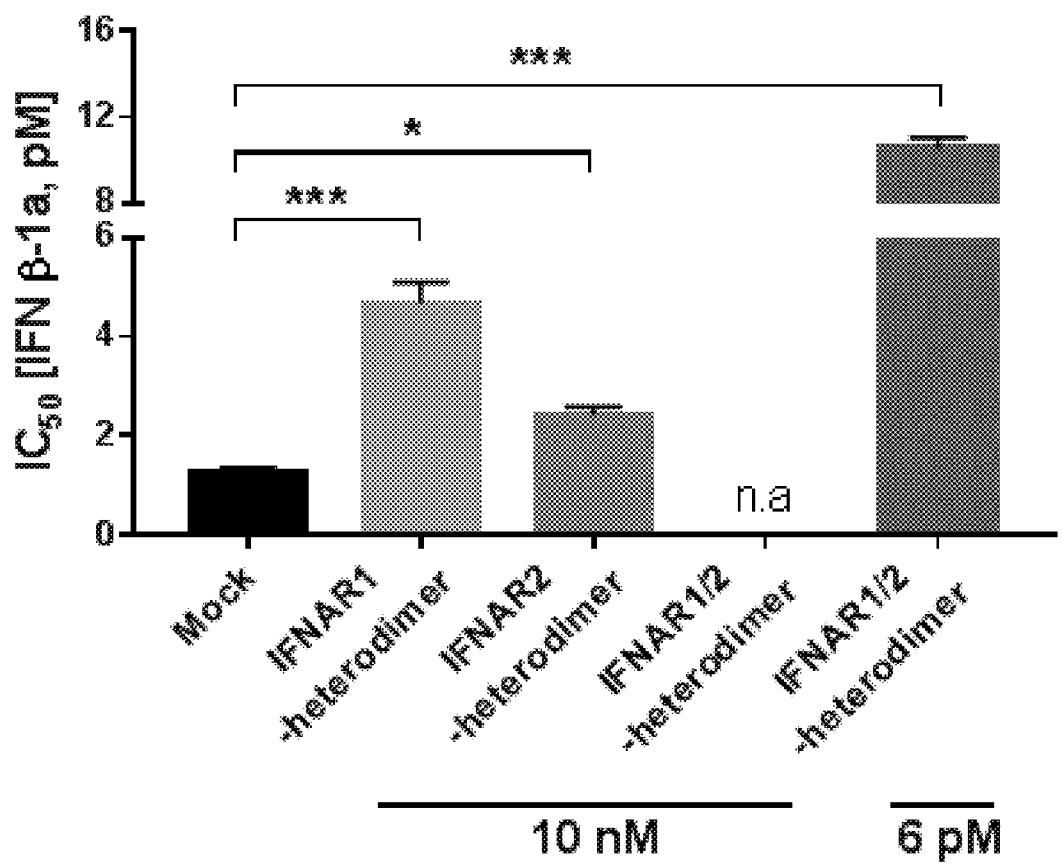

As shown in FIG. 4b, the IC50 value was the highest when the Fc fusion protein blocking both IFNAR1 and IFNAR2 according to the present invention was added. Therefore, it was confirmed that anti-cell proliferation by interferon was superior to cell viability when blocking IFNAR1 or IFNAR2, respectively.

Figure 4C:
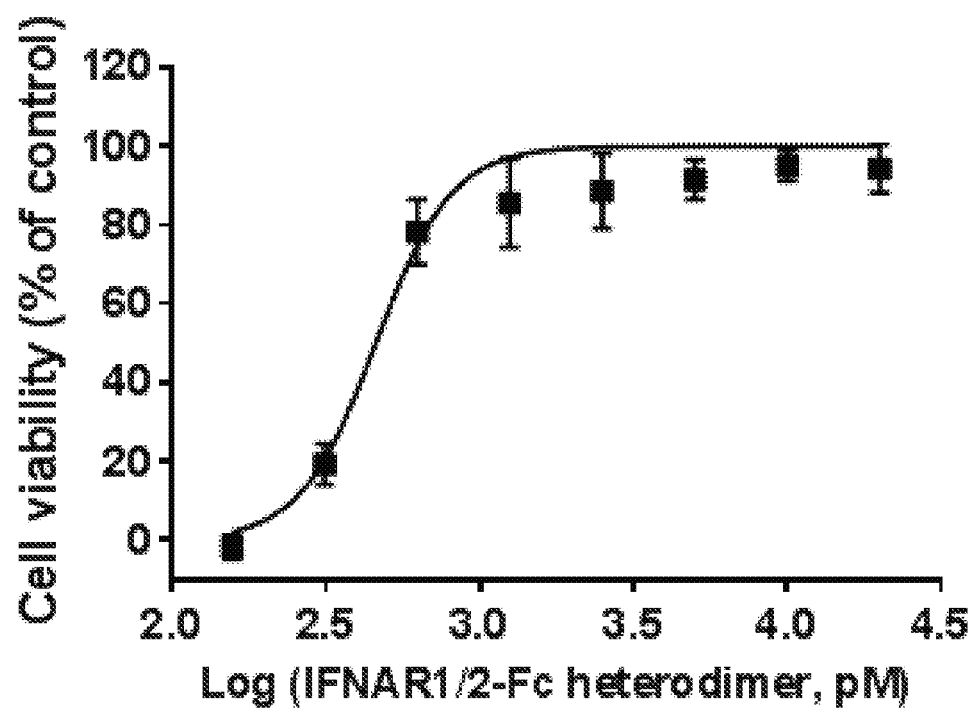

As shown in FIG. 4c, it was confirmed that the cell viability increased in a concentration-dependent manner when the IFNAR1/2-Fc heterodimer with the highest neutralizing ability was treated.

Example 5: Confirmation of Signal Mechanism Activity Neutralizing Ability by Ligand of IFNAR1/2-Fc Heterodimer In the same manner as in Example 4, except for the IFNAR1/2-Fc heterodimer mentioned below, the ability to neutralize the biological activity by the ligand of the IFNAR1/2-Fc heterodimer was confirmed.

Specifically, the group added IFNs (IFN-α 1 (pbl assay science_cat #11125-1), IFN-α 2a (pbl assay science_cat #11100-1), IFN-α 2b (pbl assay science_cat #11105-1), IFN-α 5 (pbl assay science_cat #11135-1), IFN-α 8 (pbl assay science_cat #11115-1), IFN-α 10 (pbl assay science_cat #11120-1), IFN-β 1a (pbl assay science_cat #11415-1), IFN-ω (pbl assay science_cat #11395) -One) at a concentration of 1 nM and the group that each interferon was treated with a type 1 interferon Fc fusion receptor protein at a concentration of 10 nm in cells of $3 \times 10^3$ cells were reacted in a cell incubator at 37° C. and 5% $CO_2$ for 72 hours. Then, after adding the Ex-cytox reagent according to the manufacturer's protocol, and after an additional 2 hours of reaction, it was measured at 450 nm with a Microplate reader (Genios Pro, Tecan), and $IC_{50}$ values were compared and analyzed using nonlinear regression analysis (GraphPad Prism version 7.0 software, san diego, Ca, USA).

As a result, as shown in FIG. 5, it was confirmed that the cell viability was significantly superior as compared with the cell viability treated only with interferon, when IFN-α 1, IFN-α 2a, IFN-α 2b, IFN-α 5, IFN-α 8, IFN-α 10, IFN-β 1a, IFN-ω was treated with an IFNAR1/2-Fc heterodimer (using 4GS*3 as a linker) that blocks both the binding of IFNAR1 and IFNAR2.

Through these results, it was found that the regulation of excessive interferon signals for cells is possible by the dimer-type polypeptide to which the monomer (monomer) comprising the interferon receptor fragment or antibody Fc fragment of the present invention is bound, and through this, it was confirmed that it would show excellent pharmacological effects on patients with type 1 interferon-mediated diseases such as systemic lupus erythematosus, Sjogren's syndrome, systemic sclerosis, myositis and rheumatoid arthritis in which interferon-inducible genes expressed in response to excessive interferon signals are high.

Example 6: Confirmation of Chemical Signal Inhibition Ability by Ligand of IFNAR1/2-Fc Heterodimer All experiments were performed to confirm changes in STAT1 and its phosphorylated pSTAT1 protein by Type I IFNs using Western blot in Daudi cells, in which the expression of each receptor is high.

Specifically, in a 6-well plate (SPL_cat #30006), the group added IFNs (IFN-α 1 (pbl assay science_cat #11125-1), IFN-α 2a (pbl assay science_cat #11100-1), IFN-α 2b (pbl assay science_cat #11105-1), IFN-α 5 (phi assay science_cat #11135-1), IFN-α 8 (01 assay science_cat #11115-1), IFN-α 10 (phi assay science_cat #11120-1), IFN-β 1a (phi assay science_cat #11415-1), IFN-ω (phi assay science_ cat #11395-) 1), IFN-ε (R&D systems_cat #9667-ME) at a concentration of 1 nM and the group that each interferon was treated with IFNAR1/2-Fc heterodimer protein at a concentration of 10 nM in the cells of $2 \times 10^6$ cells were reacted in a cell incubator at 37° C. and 5% $CO_2$ for 72 hours. Thereafter, cells were collected from the plate, total protein was extracted and determined with BCA protein assay kit (Thermo scientific_cat #23227). Total protein was separated on a 10% gel by sodium-dodecylsulfate-polyacrylamide gel electrophoresis (SDS-PAGE) and transcribed onto a PVDF membrane (BIO RAD_cat #1620177). The membrane was blocked with 5% skim milk, 3% bovine serum albumin, 10 mmol/L Tris-HCL (pH 8.0), 150 mmol/L NaCl, and 0.05% Tween-20 for 1 hour at room temperature. The blocked membrane was treated with STAT1 antibody (cell signaling_cat #06-501), pSTAT1 antibody (cell signaling_cat #58D6), and beta actin antibody (santa cruz_cat #sc 47778) as primary antibodies (1:3000 dilution) overnight at 4° C. Thereafter, a secondary HRP-conjugated antibody, goat anti rabbit antibody (Invitrogen_cat #31460) and goat anti mouse antibody (invitrogen_cat #G21040), was treated at room temperature for 1 hour. After treating the membrane with ECL solution (BIO RAD_cat #1705061), it was visualized on a film (Agfa healthcare_cat #EA8EC) using a developer and fixer from poohung.

As a result, as shown in FIGS. 6a and 6b, it was confirmed that phosphorylation of the pSTAT1 protein was significantly reduced as compared with the high phosphorylation of pSTAT1 protein when only interferon was treated, when the IFNAR1/2-Fc heterodimer (4GS*3) protein, which blocks both the binding of IFNAR1 and IFNAR2, was treated with interferon (IFN-α 1, IFN-α 2a, IFN-α 2b, IFN-α 5, IFN-α 8, IFN-α 10, IFN-β 1a, IFN-ω, IFN-ε). This indicates that the IFNAR1/2-Fc heterodimer protein binds to type 1 interferon and exhibits neutralizing ability, indicating that interferon-related signaling in the cell is inhibited.

INDUSTRIAL APPLICABILITY

The type 1 interferon neutralizing Fc-fusion protein of the present invention has excellent industrial applicability as while blocking the binding of type 1 interferon to the interferon receptor, has excellent initiation and biological activity inhibition of signaling mechanisms, so it can be very usefully used in the development of therapeutic agents for preventing or treating type 1 interferon-mediated diseases.

What is claimed is:

1. A dimeric polypeptide in which a monomer comprising an extracellular fragment of interferon receptor 1 (IFNAR1) and an antibody Fc fragment is bound to a monomer comprising an extracellular fragment of interferon receptor 2 (IFNAR2) and an antibody Fc fragment, wherein the antibody Fc fragment comprises the amino acid sequence of SEQ ID NO: 12 or SEQ ID NO: 14.

2. The dimeric polypeptide according to claim 1, wherein the dimeric polypeptide neutralizes type 1 interferon.

3. The dimeric polypeptide according to claim 1, wherein the extracellular fragment of the interferon receptor 1 comprises the amino acid sequence of SEQ ID NO: 4.

4. The dimeric polypeptide according to claim 1, wherein the extracellular fragment of the interferon receptor 2 comprises the amino acid sequence of SEQ ID NO: 6.

5. A polynucleotide encoding the dimeric polypeptide of claim 1.

6. A vector comprising the polynucleotide of claim 5.

7. A host cell transformed with the vector of claim 6.

8. A method for producing the dimeric polypeptide of claim 1 comprising:

(a) providing a host cell transformed with a vector comprising a polynucleotide encoding the dimeric polypeptide of claim 1;

(b) culturing the provided cells; and (c) preparing the dimeric polypeptide by recovering the dimeric polypeptide from the cells or culture medium.

9. A composition comprising the dimeric polypeptide of claim 1 as an active ingredient.

10. A method of treating a type 1 interferon-mediated disease or disorder, comprising administering to a subject in need thereof an effective amount of a composition comprising the dimeric polypeptide of claim 1 as an active ingredient.

11. The method according to claim 10, wherein the type 1 interferon-mediated disease or disorder is selected from the group consisting of systemic lupus erythematosus, Sjogren's syndrome, systemic sclerosis, insulin-dependent diabetes mellitus (IDDM), inflammatory bowel disease (IBD) (including Crohn's disease, ulcerative colitis and celiac disease), multiple sclerosis (MS), psoriasis, autoimmune thyroiditis, rheumatoid arthritis, inflammatory Myositis, glomerulonephritis HIV infection, AIDS, transplant rejection and graft-versus-host reaction (GVHD).

12. The dimeric polypeptide according to claim 1, wherein the extracellular fragment of interferon receptor 1 (IFNAR1) in the monomer is linked to the antibody Fc fragment by a linker.

13. The dimeric polypeptide according to claim 1, wherein the extracellular fragment of interferon receptor 2 (IFNAR2) in the monomer is linked to the antibody Fc fragment by a linker.

* * * * *